(12) United States Patent
Efcavitch et al.

(10) Patent No.: US 12,152,265 B2
(45) Date of Patent: *Nov. 26, 2024

(54) REUSABLE INITIATORS FOR SYNTHESIZING NUCLEIC ACIDS

(71) Applicant: Molecular Assemblies, Inc., San Diego, CA (US)

(72) Inventors: J. William Efcavitch, San Carlos, CA (US); Kim F. Albizati, San Diego, CA (US); Natasha Paul, San Diego, CA (US); Sanjay Agarwalla, San Diego, CA (US)

(73) Assignee: Molecular Assemblies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,970

(22) Filed: Jul. 11, 2022

(65) Prior Publication Data

US 2023/0227880 A1    Jul. 20, 2023

Related U.S. Application Data

(63) Continuation of application No. 16/841,214, filed on Apr. 6, 2020, now Pat. No. 11,384,377, which is a continuation-in-part of application No. 16/261,229, filed on Jan. 29, 2019, now Pat. No. 11,331,643, which is a continuation-in-part of application No. 14/829,269, filed on Aug. 18, 2015, now Pat. No. 10,683,536, which is a continuation-in-part of application No. 14/459,014, filed on Aug. 13, 2014, now Pat. No. 9,279,149, which is a continuation-in-part of application No. 14/056,687, filed on Oct. 17, 2013, now Pat. No. 8,808,989.

(60) Provisional application No. 62/069,067, filed on Oct. 27, 2014, provisional application No. 62/038,604, filed on Aug. 18, 2014, provisional application No. 61/891,162, filed on Oct. 15, 2013, provisional application No. 61/807,327, filed on Apr. 2, 2013.

(51) Int. Cl.
   C12P 19/34    (2006.01)

(52) U.S. Cl.
   CPC .................... C12P 19/34 (2013.01)

(58) Field of Classification Search
   CPC ..... C12P 19/34; C12Q 1/6869; C12Q 1/6811; C12Q 1/6806; C12Q 1/6837
   See application file for complete search history.

(56) References Cited

U.S. PATENT DOCUMENTS

| | | |
|---|---|---|
| 5,763,594 A | 6/1998 | Hiatt et al. |
| 5,808,045 A | 9/1998 | Hiatt et al. |
| 5,872,244 A | 2/1999 | Hiatt et al. |
| 5,990,300 A | 11/1999 | Hiatt et al. |
| 6,214,987 B1 | 4/2001 | Hiatt et al. |
| 6,232,465 B1 | 5/2001 | Hiatt et al. |
| 6,458,127 B1 | 10/2002 | Truckai et al. |
| 6,664,079 B2 | 12/2003 | Ju et al. |
| 7,208,172 B2 | 4/2007 | Birdsall et al. |
| 7,279,563 B2 | 10/2007 | Kwiatkowski |
| 7,414,116 B2 | 8/2008 | Milton et al. |
| 7,494,797 B2 | 2/2009 | Mueller et al. |
| 8,071,755 B2 | 12/2011 | Efcavitch et al. |
| 8,133,669 B2 | 3/2012 | Lebedev et al. |
| 8,152,839 B2 | 4/2012 | Buiser et al. |
| 8,460,910 B2 | 6/2013 | Smith et al. |
| 8,623,628 B2 | 1/2014 | Ost et al. |
| 8,808,989 B1 | 8/2014 | Efcavitch et al. |
| 9,771,613 B2 * | 9/2017 | Efcavitch ............. C12Q 1/6844 |
| 10,041,110 B2 | 8/2018 | Efcavitch et al. |
| 11,384,377 B2 * | 7/2022 | Efcavitch ............. C12Y 301/00 |
| 2004/0005614 A1 | 1/2004 | Kurn et al. |
| 2004/0043396 A1 | 3/2004 | Mueller et al. |
| 2004/0161749 A1 | 8/2004 | Hall et al. |
| 2005/0214759 A1 | 9/2005 | Wlassof et al. |
| 2005/0260609 A1 | 11/2005 | Lapidus |
| 2006/0127443 A1 | 6/2006 | Helmus |
| 2007/0036905 A1 | 2/2007 | Kramer |
| 2009/0186771 A1 | 7/2009 | Siddiqi et al. |
| 2009/0264300 A1 | 10/2009 | Franch et al. |
| 2010/0304368 A1 | 12/2010 | Cherkasov et al. |
| 2011/0081647 A1 | 4/2011 | Siddiqi et al. |
| 2011/0124529 A1 | 5/2011 | Brennan |
| 2011/0201002 A1 * | 8/2011 | Gelfand ................. A61P 31/00 435/6.1 |
| 2012/0040340 A1 | 2/2012 | Efcavitch et al. |

(Continued)

FOREIGN PATENT DOCUMENTS

| | | |
|---|---|---|
| EP | 1 350 842 A2 | 10/2003 |
| JP | S63-304989 A | 12/1988 |

(Continued)

OTHER PUBLICATIONS

Lee et al., A Microfluidic Oligonucleotide Synthesizer. Nucleic Acids Res 2010;38:2514-2521.

LeProust et al., Synthesis of high-quality libraries of long (150mer) oligonucleotides by a novel depurination controlled process. Nucleic Acids Res 2010;38(8):2522-2540.

Li et al., Single-step procedure for labeling DNA strand breaks with fluorescein- or BODIPY-conjugated deoxynucleotides: detection of apoptosis and bromodeoxyuridine incorporation. Cytometry 1995;20(2):172-180.

(Continued)

*Primary Examiner* — Jezia Riley

(74) *Attorney, Agent, or Firm* — Withers Bergman LLP; Thomas C. Meyers

(57) ABSTRACT

The invention provides improved methods for synthesizing polynucleotides, such as DNA and RNA, using renewable initiators coupled to a solid support. Using the methods of the invention, specific sequences of polynucleotides can be synthesized de novo, base by base, in an aqueous environment, without the use of a nucleic acid template.

20 Claims, 26 Drawing Sheets

Specification includes a Sequence Listing.

(56) References Cited

U.S. PATENT DOCUMENTS

| | | | |
|---|---|---|---|
| 2013/0189743 | A1 | 7/2013 | Balasubramanian et al. |
| 2013/0244888 | A1* | 9/2013 | Zhao .................. C12Q 1/6869 |
| | | | 435/6.12 |
| 2014/0363851 | A1 | 12/2014 | Efcavitch et al. |
| 2016/0046974 | A1 | 2/2016 | Efcavitch et al. |
| 2016/0060621 | A1 | 3/2016 | Agresti et al. |
| 2018/0023108 | A1 | 1/2018 | Chen et al. |
| 2018/0312820 | A1 | 11/2018 | Pomerantz et al. |
| 2019/0275492 | A1 | 9/2019 | Efcavitch et al. |

FOREIGN PATENT DOCUMENTS

| | | | |
|---|---|---|---|
| JP | 2003304889 | A | 10/2003 |
| JP | 2011224016 | A | 11/2011 |
| WO | 92/10587 | A1 | 6/1992 |
| WO | 94/14972 | A1 | 7/1994 |
| WO | 2002072791 | A2 | 9/2002 |
| WO | 2005/005667 | A2 | 1/2005 |
| WO | 2005/024010 | A1 | 3/2005 |
| WO | 2005/026184 | A2 | 3/2005 |
| WO | 2005/080605 | A2 | 9/2005 |
| WO | 2006/007207 | A2 | 1/2006 |
| WO | 2007/022493 | A2 | 2/2007 |
| WO | 2007/062160 | A2 | 5/2007 |
| WO | 2007/147110 | A2 | 12/2007 |
| WO | 2008/046602 | A2 | 4/2008 |
| WO | 2008/046609 | A2 | 4/2008 |
| WO | 2008/144315 | A1 | 11/2008 |
| WO | 2008/144544 | A1 | 11/2008 |
| WO | 2009/124254 | A1 | 10/2009 |
| WO | 2013013820 | A1 | 1/2013 |
| WO | 2013040257 | A1 | 3/2013 |
| WO | 2014162307 | A2 | 10/2014 |
| WO | 2016128732 | A1 | 8/2016 |

OTHER PUBLICATIONS

Life Technologies [Internet]. Carlsbad: Life Technologies Inc.; c 2013. Oligo Minimum Yield Guarantee; [cited Dec. 1, 2013]. Available from: http://www.lifetechnologies.com/us/en/home/products-and-services/product-types/primers-oligos-nucleotides/invitrogen-custom-dna-oligos/oligo-ordering-details/oligo-minimum-yield-guarantee.html.
Litosh et al., Improved nucleotide selectivity and termination of 3 ?- OH unblocked reversible terminators by molecular tuning of 2-nitrobenzyl alkylated HOMedU triphosphates. Nucleic Acid Res 2011;39:e39.
Matteucci et al., Studies on Nucleotide Chemistry IV. Synthesis of Deoxyoligonucleotides on a Polymer Support. J. Amer. Chem. Soc. 1981;103:3185-3191.
Matzas et al., Next Generation Gene Synthesis by targeted retrieval of bead-immobilized, sequence verified DNA clones from a high throughput pyrosequencing device. Nat Biotechnol. 2010;28(12):1291-1294.
McBride et al., Amidine protecting groups for oligonucleotide synthesis, J. Am. Chem. Soc., 1986, 108, 2040-2048.
Meng et al., Design and synthesis of a photocleavable fluorescent nucleotide 3'-O-allyl-dGTP-PC-Bodipy-FL-510 as a reversible terminator for DNA sequencing by synthesis. J Org Chem. Apr. 14, 2006;71(8):3248-3252.
Metzker et al., Termination of DNA synthesis by novel 3'-modified-deoxyribonucleoside 5'-triphosphates. Nucleic Acids Res 1994;22:4259-4267.
Minhaz, A theoretical model for template-free synthesis of long DNA sequence. Syst Synth Biol. 2009;2:67-73.
Motea et al., Terminal deoxynucleotidyl transferase: The story of a misguided DNA polymerase. Biochimica et Biophysica Acta 2010; 1804:1151-1156.
Muller et al., Enzymatic synthesis of double-stranded DNA containing radioactively labeled O6-ethylguanine as the only modified base. Carcinogenesis 1981;2(4):321-327.

Nitta et al., Synthesis of a photoresponsive alpha-dideoxyuridine triphosphate derivative. Nucleic Acids Symp Ser (Oxf). 2008;(52):293-294.
Romain et al., Conferring a template-dependent polymerase activity to terminal deoxynucleotidyltransferase by mutations in the Loop1 region. Nucleic Acids Res. 2009;37(14):4642-4656.
Ruparel et al., "Design and synthesis of a 3' O-ally photocleavable fluorescent nucleotide as a reversible terminator for DNA sequencing by synthesis," Proceedings of the National Academy of Sciences of the United States of America, Apr. 13, 2005, vol. 102, Iss. 17, pp. 5932-5937, entire document.
Schott et al., Single-step elongation of oligodeoxynucleotides using terminal deoxynucleotidyl transferase. Eur J Biochem 1984;143:613-620.
Sessler et al., Molecular recognition via base-pairing, Chem. Soc. Rev., 2007, 36, 314-325.
Siegel et al., Computational design of an enzyme catalyst for a stereoselective bimolecular Diels-Alder reaction. Science. Jul. 16, 2010;329(5989):309-313.
Sleight et al., In-Fusion BioBrick assembly and re-engineering. Nucleic Acids Res. May 2010;38(8):2624-2636.
Sugiyama et al., Preparation of sensitive and specific oligonucleotide probes tailed using terminal transferase and dITP. Biotechniques. Mar. 2000;28(3):486-490.
Sørensen et al., Enzymatic Ligation of Large Biomolecules to DNA. ACS Nano 2013;7(9):8098-8104.
Tjong et al., Amplified on-chip fluorescence detection of DNA hybridization by surface-initiated enzymatic polymerization. Anal Chem 2011;83:5153-5159.
Wu et al., Improvement of a potential anthrax therapeutic by computational protein design. J Biol Chem. Sep. 16, 2011;286(37):32586-32592.
Yang et al., Mutational Analysis of Residues in the Nucleotide Binding Domain of Human Terminal Deoxynucleotidyl Transferase. J. Mol. Biol. Apr. 22, 1994; 269(16):11859-11868.
Zahid et al., DNA nanotechnology: a future perspective. Nanoscales Res Lett. 2013;8:119-132.
Zhou et al., A magnetic bead-based protein kinase assay with dual detection techniques. Anal. Biochem. 2011;408:5-11.
Alexandrova et al., New triphosphate conjugates bearing reporter groups: labeling of DNA fragments for microarray analysis. Bioconjug Chem. May-Jun. 2007;18(3):886-93.
Auriol et al., Acetoxy-acetylaminofluorene-modified dGTP can be used to label oligonucleotides or DNA enzymatically. Mol Cell Probes Apr. 1997;11(2):113-21.
Barone et al., Novel nucleoside triphosphate analogs for the enzymatic labeling of nucleic acids. Nucleoside, Nucleotides and Nucleic Acids 2001;20(4-7):1141-5.
Beaucage et al., Studies on Nucleotide Chemistry V. Deoxynucleoside Phosphoramidites—A New Class of Key Intermediates for Deoxypolynucleotide Synthesis. Tetrahedron Lett. 1981;22:1859-62.
Bentley et al., Accurate whole human genome sequencing using reversible terminator chemistry.Nature 2008;456:53-59.
Bi et al., Design and synthesis of a chemically cleavable fluorescent nucleotide, 3'-O-allyl-dGTP-allyl-bodipy-FL-510, as a reversible terminator for DNA sequencing by synthesis. J Am Chem Soc. Mar. 1, 2006;128(8):2542-2543.
Bollum FJ. Terminal Deoxynucleotidyl Transferase. In: Boyer PD, editor. The Enzymes. vol. 10. New York: Academic Press; 1974. p. 148.
Boule et al., High-Level Expression of Murine Terminal Deoxynucleotidyl Transferase in *Escherichia coli* at Low Temparature and Overexpressing argU tRNA. Mol Biotechnology 1998;10:199-208.
Bowers et al., 2009, Virtual Terminator nucleotides for next generation DNA sequencing, Nat Methods 6:593-595 (and whole document).
Büssow et al., A human cDNA library for high-throughput protein expression screening. Genomics. Apr. 1, 2000;65(1):1-8.
Carlson R, The changing economics of DNA synthesis. Nature Biotechnol. 2009;27:1091-4.

(56) References Cited

OTHER PUBLICATIONS

Carr et al., Protein-mediated error correction for de novo DNA Synthesis. Nucleic Acids Research 2004;vol. 32(20):e162.
Caruthers MH. Gene Synthesis Machines: DNA chemistry and its Uses. Science 1985;230(4723):281-5.
Chang et al., Molecular Biology of terminal Transferase. CRC Crit Rev Biochem. 1986;21(1):27-52.
Chen et al., Reconstructed evolutionary adaptive paths give polymerases accepting reversible terminators for sequencing and SNP detection. Proc Natl Acad Sci U S A. Feb. 2, 2010;107(5):1948-53.
Chow et al., Enzymatic fabrication of DNA nanostructures: Extension of a self-assembled oligonucleotide monolayer on gold arrays. J Am Chem Soc 2005;127:14122-3.
Chow et al., Surface-initiated enzymatic polymerization of DNA. Langmuir 2007; 23:11712-11717.
Damiani et al., Sequence analysis of heteropolymeric DNA synthesized in vitro by the enzyme terminal deoxynucleotidyl transferase and cloned in *Escherichia coli*. Nucleic Acids Res 1982;10(20):6401-6410.
Deibel et al., Fluorimetric assay for terminal deoxynucleotidyl transferase activity. Anal Biochem 1985;144(2):336-346.
Delarue et al., structures of a template-independent DNA polymerase: murine terminal deoxynucleotidyltransferase. EMBO J. 2002;21(3):427-39.
Efcavitch. Automated System for the Optimized Chemical Synthesis of Oligodeoxyribonucleotides. In: Schlesinger DH, editor. Macromolecular Sequencing and Synthesis. New York: Alan R Liss, Inc.; 1988. p. 221-234.
Li et al., "Exocyclic Carbons Adjacent to the N6 of Adenine are Targets for Oxidation by the *Escherichia coli* Adaptive Response Protein AlkB," J. Am. Chem. Soc. 134, 2012, 8896-8901.
Ngo et al., "Computational Complexity, Protein Structure Prediction, and the Levinthal Paradox," The Protein Folding Problem and Teritory Structure Prediction, Birkhauser, Boston, MA, 1994, pp. 433 and 492-495.
Quignard et al., "Consequences of methylation on the amino group of adenine," Eur. J. Biochem, 152, 1985, 99-105.
Figeys et al., Labeling of double-stranded DNA by ROX-dideoxycytosine triphosphate using terminal deoxynucleotidyl transferase and separation by capillary electrophoresis. Anal Chem 1994;66(23):4382-4383.
Flickinger et al., Differential incorporation of biotinylated nucleotides by terminal deoxynucleotidyl transferase. Nucleic Acids Res 1992;20(9):2382.
Gordon et al., Computational design of an ?-gliadin peptidase. J Am Chem Soc. Dec. 19, 2012;134(50):20513-20520.
Gouge et al., Structures of Intermediates along the Catalytic Cycle of Terminal Deoxynucleotidyltransferase: Dynamical Aspects of the Two-Metal Ion Mechanism. J Mol Biol. Nov. 15, 2013;425(22):4334-52.
Guo et al., Four-color DNA sequencing with 3'-Omodifiednucleotide reversible terminators and chemically cleavable fluorescent dideoxynucleotides. Proc. Natl. Acad. Sci. USA 2008;105:9145-9150.
Haynes et al., A Chemically Synthesized Peptoid-Based Drag-Tag Enhances Free-Solution DNA Sequencing by Capillary Electrophoresis. Biopolymers. 2011, vol. 96, No. 5, pp. 702-707.
Hoard et al., Heteropolydeoxynucleotides synthesized with terminal deoxyribonucleotidyl transferase. J of Biol Chem 1969;244(19):5363-5373.

Hogg et al., "Promiscuous DNA synthesis by human DNA polymerase Ø," Nov. 30, 2011, vol. 40, Iss. 6, pp. 2611-2622, entire document.
Horakova et al., Tail-labelling of DNA probes using modified deoxynucleotide triphosphates and terminal deoxynucleotidyl transferase. Application in electrochemical DNA hybridization and protein-DNA binding assays. Org Biomol Chem 2011;9(5):1366-1371.
Hutter et al., Labeled nucleoside triphosphates with reversibly terminating aminoalkoxyl groups. Nucleosides Nucleotides Nucleic Acids. Nov. 2010;29(11):879-895.
Ikeda et al., Specifc 3'-terminal modification of DNA with a novel nucleoside analogue that allows a covalent linkage of a nuclear localization signal and enhancement of DNA stability. ChemBioChem 2005;6:297-303.
International Search Report and The Written Opinion of the International Searching Authority for International Application No. PCT/US2015/045729 dated Dec. 14, 2015 (16 Pages).
International Search Report and Written Opinion for PCT/US2014/033811, mailed Sep. 30, 2014 (12 Pages).
International Search Report and Written Opinion if the International Seach Authority for PCT/US2018/023356, mailed Mar. 20, 2018, 12 pages.
International Search Report and Written Opinion issued in International Application No. PCT/US2020/015640, date of mailing: May 25, 2020, 12 pages.
International Search Report and Written Opinion mailed on Jan. 21, 2015, for International Patent Application No. PCT/IB2014/061673, filed May 23, 2014 (16 pages).
International Search Report and Written Opinion of the International Search Authority Mailed Feb. 8, 2016 for International Application No. PCT/US2015/045730 (17 Pages).
Ju et al., Four-color DNA sequencing by synthesis using cleavable fluorescent nucleotide reversible terminators. Proc Natl Acad Sci U S A. Dec. 26, 2006;103(52):19635-19640.
Kasahara et al., Effect of 3'-end capping of aptamer with various 2',4'-bridged nucleotides: Enzymatic post-modification toward a practical use of polyclonal aptamers. Bioorg Med Chem Lett. Mar. 1, 2010;20(5):1626-1629.
Kent et al., "DNA polymerase specializes in incorporating synthetic expanded-size (xDNA) nucleotides," Nucleic Acids Research, Sep. 2, 2016, vol. 44, No. 19, pp. 9381-9392, entire document.
Kent et al., "Polymerase Ø is a robust terminal transferase that oscillates between three different mechanisms during end-joining," Jun. 17, 2016, eLIFE, vol. 5, Article e13740, pp. 1/25, entire documents.
Kosuri et al., Scalable gene synthesis by selective amplification of DNA pools from high-fidelity microchips. Nat Biotechnol. Dec. 2010;28(12):1295-1299.
Kosuri S, Church GM. Large-scale de novo DNA synthesis: technologies and applications. Nat Methods. May 2014;11(5):499-507.
Kuan et al., Generation of active bovine Terminal Deoxynucleotidyl Transferase (TdT) in *E. coli*. Biochem. Insights. 2010;3:41-46.
Lashkari et al., An automated multiplex oligonucleotide synthesizer: development of high-throughput, low-cost DNA synthesis. Proc Natl Acad Sci USA. 1995 ;92(17):7912-7915.
Leconte et al., Directed evolution of DNA polymerases for next generation sequencing. Angew Chem Int Ed Engl. 2010;49(34):5921-5924.

* cited by examiner n = 2 or 3
X = O, NH, CH$_2$, S n = 1 - 4
X = O, S, NH, CH$_2$

X = O, S, NH, CH$_2$ n = 1 - 4
X = O, S, NH, CH$_2$ n = 1 - 4
X = O, S, NH, CH$_2$ n = 1 - 4
X = O, S, NH, CH$_2$

REUSABLE INITIATORS FOR SYNTHESIZING NUCLEIC ACIDS

RELATED APPLICATIONS

This application is a Continuation of U.S. Non-Provisional patent application Ser. No. 16/841,214, filed Apr. 6, 2020, which is a Continuation-in-Part of U.S. Non-Provisional patent application Ser. No. 16/261,229, filed Jan. 29, 2019 and issued as U.S. Pat. No. 11,331,643, which is a Continuation-in-Part of U.S. Non-Provisional patent application Ser. No. 14/829,269, filed Aug. 18, 2015 and issued as U.S. Pat. No. 10,683,536, which is a continuation-in-part of U.S. Non-provisional patent application Ser. No. 14/459,014, filed Aug. 13, 2014 and issued as U.S. Pat. No. 9,279,149, which is a continuation-in-part of U.S. Non-provisional patent application Ser. No. 14/056,687, filed Oct. 17, 2013, now issued as U.S. Pat. No. 8,808,989, which claims the benefit of and priority to U.S. Provisional Patent Application Ser. No. 61/891,162, filed Oct. 15, 2014 and U.S. Provisional Patent Application Ser. No. 61/807,327, filed Apr. 2, 2013. U.S. application Ser. No. 14/829,269 additionally claims priority to U.S. Provisional Patent Application Ser. No. 62/069,067, filed Oct. 27, 2014 and U.S. Provisional Patent Application Ser. No. 62/079,604, filed Aug. 18, 2014. The contents of each of the above applications are incorporated by reference herein in their entireties.

FIELD OF THE INVENTION

The invention relates to methods and apparatus for synthesizing polynucleotides with a desired sequence and without the need for a template.

SEQUENCE LISTING

This application contains a sequence listing which has been submitted in eXtensible Markup Language (XML) format via the Patent Center and is hereby incorporated by reference in its entirety. The XML-formatted sequence listing, created on Feb. 17, 2023, is named MOLA-001-12US-Seqs.xml and is 16.6 kilobytes in size.

BACKGROUND

Most de novo nucleic acid sequencing is performed using well-established solid-phase phosphoramidite-techniques. The phosphoramidite technique involves the sequential deprotection and synthesis of sequences built from phosphoramidite reagents corresponding to natural (or non-natural) nucleic acid bases. Phosphoramidite nucleic acid synthesis is length-limited, however, in that nucleic acids greater than 200 base pairs (bp) in length experience high rates of breakage and side reactions. Additionally, phosphoramidite synthesis produces toxic by-products, and the disposal of this waste limits the availability of nucleic acid synthesizers, and increases the costs of contract oligonucleotide production. (It is estimated that the annual demand for oligonucleotide synthesis is responsible for greater than 300,000 gallons of hazardous chemical waste, including acetonitrile, trichloroacetic acid, toluene, tetrahydrofuran, and pyridine. See LeProust et al., Nucleic Acids Res., vol. 38(8), p. 2522-2540, (2010), incorporated by reference herein in its entirety). Thus, there is a need for more efficient and cost-effective methods for oligonucleotide synthesis.

SUMMARY

The invention provides improved methods for nucleic acid synthesis. Methods of the invention provide faster and longer de novo synthesis of polynucleotides. As such, the invention dramatically reduces the overall cost of custom nucleic acid synthesis. Methods of the invention are directed to template-independent synthesis of polynucleotides by using a nucleotidyl transferase enzyme to incorporate nucleotide analogs coupled to an inhibitor by a cleavable linker. Because of the inhibitor, synthesis pauses with the addition of each new base, whereupon the linker is cleaved, separating the inhibitor and leaving a polynucleotide that is essentially identical to a naturally occurring nucleotide (i.e., is recognized by the enzyme as a substrate for further nucleotide incorporation).

In particular, the invention provides a renewable substrate for template-independent nucleic acid synthesis. De novo synthesis begins with a nucleic acid initiator that is bound to a solid support. In the presence of a suitable enzyme, e.g., a polymerase, e.g., a terminal deoxynucleotidyl transferase (TdT), nucleotide analogs are added to the nucleic acid initiator in order to create an oligonucleotide. It is preferable that the nucleotide analogs include removable terminating groups that cause the enzymatic addition to stop after the addition of one nucleotide. A removable terminating group can be linked to the base portion of the nucleic acid and/or to the 3' hydroxyl of the nucleic acid. Deblocking of the terminating group and/or the 3' blocking group, creates a new active site that is a substrate for the enzyme. With subsequent addition of a new nucleotide or nucleotide analog, the oligonucleotide is extended.

In some instances, the nucleic acid initiator comprises a 3' moiety that is a substrate for the enzyme. A releasing agent is used to decouple the 3' moiety, thereby releasing the oligonucleotide. The 3' moiety, the nucleic acid initiator, and the solid support are reusable after the release of the nascent oligonucleotide.

The invention additionally includes an apparatus that utilizes methods of the invention for the production of custom polynucleotides. An apparatus of the invention includes one or more bioreactors providing aqueous conditions and a plurality of sources of nucleotide analogs. The bioreactor may be e.g., a reservoir, a flow cell, or a multi-well plate. The bioreactor may include a solid support having a nucleic acid initiator and a cleavable 3' moiety. Starting from the solid support, the polynucleotides are grown in the reactor by adding successive nucleotides via the natural activity of a nucleotidyl transferase, e.g., a terminal deoxynucleotidyl transferase (TdT) or any other enzyme that elongates DNA or RNA strands without template direction. Upon cleavage of the linker, a natural polynucleotide is released from the solid support. Once the sequence is complete, the support is cleaved away, or the 3' moiety is contacted with a releasing agent, leaving a polynucleotide essentially equivalent to that found in nature. In some embodiments, the apparatus is designed to recycle nucleotide analog solutions by recovering the solutions after nucleotide addition and reusing solutions for subsequence nucleotide addition. Thus, less waste is produced, and the overall cost per base is reduced as compared to state-of-the-art methods. In certain embodiments, a bioreactor may include a microfluidic device and/or use inkjet printing technology.

Terminating groups may include, for example, charged moieties or steric inhibitors. In general, large macromolecule that prevent nucleotidyl transferase enzymes from achieving a functional conformation are useful used to inhibit oligonucleotide synthesis. Such macromolecules include polymers, polypeptides, polypeptoids, and nanoparticles. The macromolecules should be large enough to physically block access to the active site of the nucleotidyl transferase, not so large as to negatively alter the reaction kinetics. The macromolecules are linked to nucleotide analogs using any of a variety of linkers, as described below.

In embodiments using a 3'-O-blocked nucleotide analog, the 3'-O-blocking groups are typically small and easily removed, thus allowing use with engineered enzymes having modified active sites. For example, the 3'-O-blocking groups may comprise azidomethyl, amino, or allyl groups.

In some embodiments, oligonucleotide synthesis may include introduction of a 3' exonuclease to the one or more synthesized oligonucleotides after each nucleotide analog addition, but before cleaving the terminating group. The terminating group blocks the 3' exonuclease from acting on any oligonucleotide that to which a nucleotide analog has been added, while oligonucleotides that have not successfully added an analog containing a terminator are removed by the 3' exonuclease. In this manner, the invention allows for in-process quality control and may eliminate the need for post-synthesis purification.

Other aspects of the invention are apparent to the skilled artisan upon consideration of the following figures and detailed description.

BRIEF DESCRIPTION OF THE DRAWINGS

FIG. 111B shows cleavage of the cleavable terminator from a rUTP analog of FIG. 11A to achieve a rUTP and a cyclic leaving molecule;

DETAILED DESCRIPTION

Figure 1A:
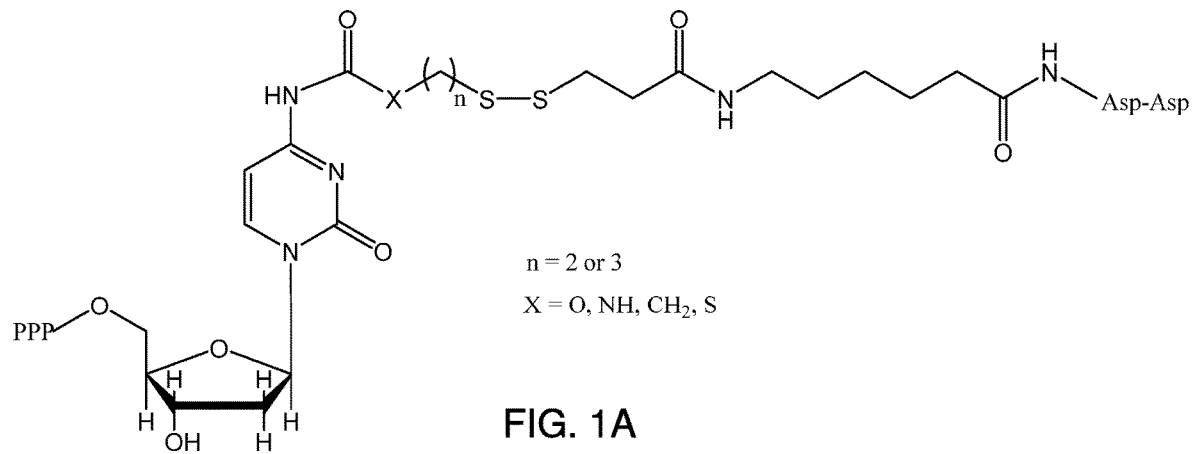
FIG. 1A shows a genus of deoxycytidine triphosphate (dCTP) analogs having a cleavable terminator linked at the N-4 position.

The invention provides improved methods for synthesizing polynucleotides, such as DNA and RNA, using enzymes and nucleic acid analogs. Using the disclosed methods, specific sequences of polynucleotides can be synthesized de novo, base by base, in an aqueous environment, and without the use of a nucleic acid template.

Nucleotide analogs may have an unmodified 3' hydroxyl, or may have a 3'-O-blocking group or may have a blocker releasably attached to a phosphate. In any case, the blocking group is designed to not leave behind substantial additional molecules, i.e., designed to leave behind "scarless" nucleotides that are recognized as "natural" nucleotides by the enzyme. Thus, at the conclusion of the synthesis, upon removal of the last blocking group, the synthesized polynucleotide is chemically and structurally equivalent to the naturally-occurring polynucleotide with the same sequence. The synthetic polynucleotide can, thus, be incorporated into living systems without concern that the synthesized polynucleotide will interfere with biochemical pathways or metabolism.

The process and analogs of the invention are used for the non-template mediated enzymatic synthesis of oligo- and oligodeoxynucleotides especially of long oligonucleotides (<5000 nt). Products can be single stranded or partially double stranded depending upon the initiator used. The synthesis of long oligonucleotides requires high efficiency incorporation and high efficiency of reversible terminator removal. The initiator bound to the solid support consists of a short, single strand DNA sequence that is either a short piece of the user defined sequence or a universal initiator from which the user defined single strand product is removed.

In one aspect, the disclosed methods employ commercially-available nucleotidyl transferase enzymes, such as terminal deoxynucleotidyl transferase (TdT), to synthesize polynucleotides from nucleotide analogs in a step-by-step fashion. The nucleotide analogs are of the form:

NTP-linker-inhibitor wherein NTP is a nucleotide triphosphate (i.e., a dNTP or an rNTP), the linker is a cleavable linker between the pyridine or pyrimidine of the base, and the inhibitor is a group that prevents the enzyme from incorporating subsequent nucleotides. At each step, a new nucleotide analog is incorporated into the growing polynucleotide chain, whereupon the enzyme is blocked from adding an additional nucleotide by the inhibitor group. Once the enzyme has stopped, the excess nucleotide analogs are removed from the growing chain, the inhibitor can be cleaved from the NTP, and new nucleotide analogs can be introduced in order to add the next nucleotide to the chain. By repeating the steps sequentially, it is possible to quickly construct nucleotide sequences of a desired length and sequence.

Advantages of using nucleotidyl transferases for polynucleotide synthesis include: 1) 3'-extension activity using single strand (ss) initiating primers in a template-independent polymerization, 2) the ability to extend primers in a highly efficient manner resulting in the addition of thousands of nucleotides, and 3) the acceptance of a wide variety of modified and substituted NTPs as efficient substrates.

In addition, the invention can make use of an initiator sequence that is a substrate for nucleotidyl transferase. The initiator is attached to a solid support and serves as a recognition site for the enzyme. The initiator is preferably a universal initiator for the enzyme, such as a homopolymer sequence, and is recyclable on the solid support, the formed oligonucleotide being cleavable from the initiator.

Methods of the invention are well-suited to a variety of applications that currently use synthetic nucleic acids, e.g., phosphoramidite-synthesized DNA oligonucleotides. For example, polynucleotides synthesized using the methods of the invention are used as primers for nucleic acid amplification, hybridization probes for detection of specific markers, and for incorporation into plasmids for genetic engineering. However, because the disclosed methods produce longer synthetic strings of nucleotides, at a faster rate, and in an aqueous environment, the disclosed methods also lend themselves to high-throughput applications, such as screening for expression of genetic variation in cellular assays, as well as synthetic biology. Furthermore, the methods of the invention will provide the functionality needed for next-generation applications, such as using DNA as synthetic read/write memory, or creating macroscopic materials synthesized completely (or partially) from DNA.

The invention and systems described herein provide for synthesis of polynucleotides, including deoxyribonucleic acids (DNA) and ribonucleic acids (RNA). While synthetic pathways for "natural" nucleotides, such as DNA and RNA, are described in the context of the common nucleic acid bases, e.g., adenine (A), guanine (G), cytosine (C), thymine (T), and uracil(U), it is to be understood that the methods of the invention can be applied to so-called "non-natural" nucleotides, including nucleotides incorporating universal bases such as 3-nitropyrrole 2'-deoxynucloside and 5-nitroindole 2'-deoxynucleoside, alpha phosphorothiolate, phosphorothioate nucleotide triphosphates, or purine or pyrimidine conjugates that have other desirable properties, such as fluorescence. Other examples of purine and pyrimidine bases include pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. In some instances, it may be useful to produce nucleotide sequences having unreactive, but approximately equivalent bases, i.e., bases that do not react with other proteins, i.e., transcriptases, thus allowing the influence of sequence information to be decoupled from the structural effects of the bases.

Analogs

The invention provides nucleotide analogs having the formula NTP-linker-inhibitor for synthesis of polynucleotides in an aqueous environment. With respect to the analogs of the form NTP-linker-inhibitor, NTP can be any nucleotide triphosphate, such as adenosine triphosphate (ATP), guanosine triphosphate (GTP), cytidine triphosphate (CTP), thymidine triphosphate (TTP), uridine triphosphate (UTP), nucleotide triphosphates, deoxyadenosine triphosphate (dATP), deoxyguanosine triphosphate (dGTP), deoxycytidine triphosphate (dCTP), deoxythymidine triphosphate (dTTP), or deoxyuridine triphosphate (dUTP).

The linker can be any molecular moiety that links the inhibitor to the NTP and can be cleaved. For example, the linkers can be cleaved by adjusting the pH of the surrounding environment. The linkers may also be cleaved by an enzyme that is activated at a given temperature, but inactivated at another temperature. In some embodiments, the linkers include disulfide bonds.

Linkers may, for example, include photocleavable, nucleophilic, or electrophilic cleavage sites. Photocleavable linkers, wherein cleavage is activated by a particular wavelength of light, may include benzoin, nitroveratryl, phenacyl, pivaloyl, sisyl, 2-hydroxy-cinamyl, coumarin-4-yl-methyl, or 2-nitrobenzyl based linkers.

Figure 15:
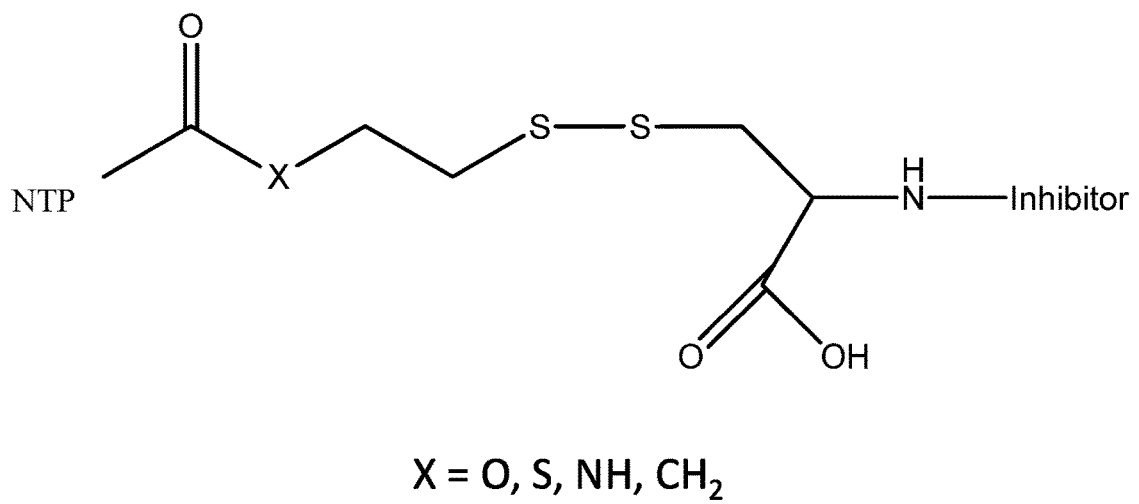
FIG. 15 shows an exemplary nucleotide analog with a cleavable linker comprising a cysteine residue.

Examples of nucleophilic cleavage sites include fluoride ion cleavable silicon-oxygen bonds or esters which may be cleaved in a basic solution. Electrophilically-cleaved linkers may include acid induced cleavage sites which may comprise trityl, tert-butyloxycarbonyl groups, acetal groups, and p-alkoxybenzyl esters and amides. In certain aspects, a cleavable linker may include a cysteine residue as shown in FIG. 15.

The linker can be attached, for example, at the N4 of cytosine, the N3 or O4 of thymine, the N2 or N3 of guanine, and the N6 of adenine, or the N3 or O4 of uracil because attachment at a carbon results in the presence of a residual scar after removal of the polymerase-inhibiting group. The linker is typically on the order of at least about 10 Angstroms long, e.g., at least about 20 Angstroms long, e.g., at least about 25 Angstroms long, thus allowing the inhibitor to be far enough from the pyridine or pyrimidine to allow the enzyme to bind the NTP to the polynucleotide chain via the attached sugar backbone. In some embodiments, the cleavable linkers are self-cyclizing in that they form a ring molecule that is particularly non-reactive toward the growing nucleotide chain.

In certain aspects, a cleavable linker may include a variable number of methylene bridges on the NTP or the inhibitor side of a disulfide bond, including, for example, 1, 2, 3, or 4 methylene bridges as shown in FIGS. 14 and 16A-C. These methylene bridges may be used to increase the space between the NTP and the inhibitor. As noted above, the length of the cleavable linker may be selected in order to prevent the inhibitor from interfering with coupling of the NTP to the synthesized polynucleotide. In some embodiments of the invention, the distance of the charged group to the NTP plays an important role in the effectiveness of inhibiting a subsequent nucleotide incorporation.

For example, in some embodiments using a charged moiety as an inhibitor, the charged moiety may be from about 5 to about 60 bonds away from the NTP. In some other embodiments, the charged moiety of the inhibitor may be from about 10 to about 40 bonds away from the NTP. In some other embodiments, the charged moiety of the inhibitor can be from about 10 to about 35 bonds away from the NTP. In some other embodiments, the charged moiety of the inhibitor may be from about 10 to about 30 bonds away from the NTP. In some other embodiments, the charged moiety of the inhibitor is from about 10 to about 20 bonds away from the NTP. The number of bonds between the charged moiety and the NTP may be increased by including additional methylene bridges.

Figure 16A:
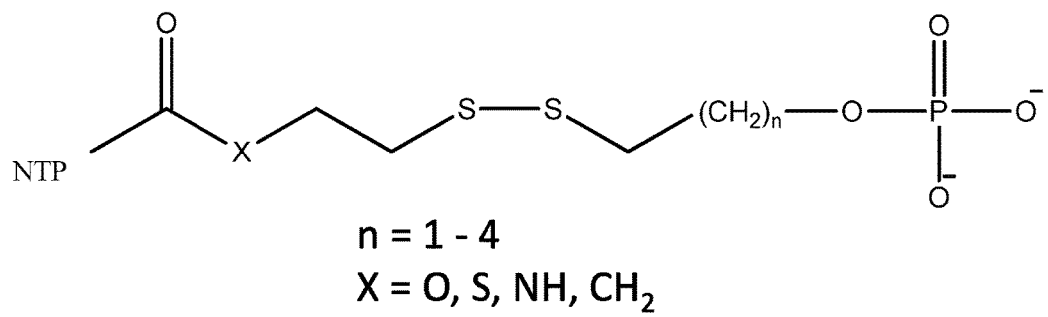
FIG. 16A shows an exemplary nucleotide analog with an anionic inhibitor comprising a single phosphate group.
Figure 16B:
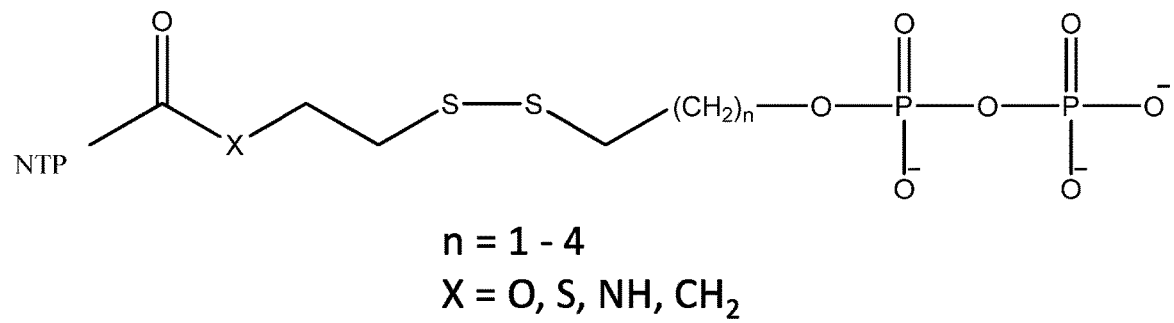
FIG. 16B shows an exemplary nucleotide analog with an anionic inhibitor comprising two phosphate groups.
Figure 16C:
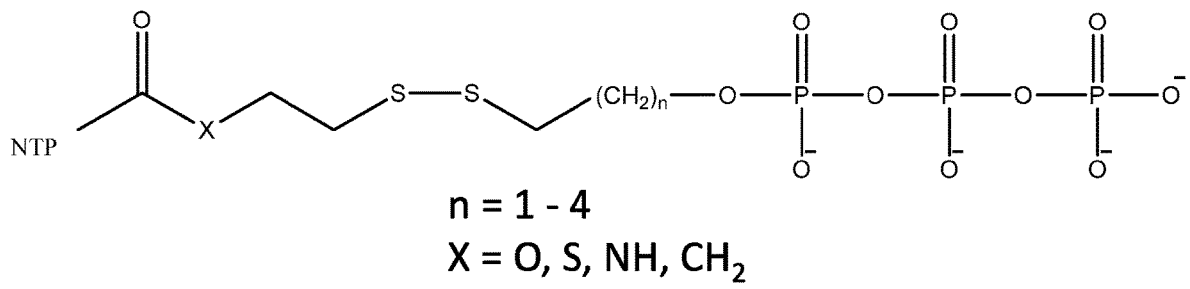
FIG. 16C shows an exemplary nucleotide analog with an anionic inhibitor comprising three phosphate groups.

The nucleotide analogs can include any moiety linked to the NTP that inhibits the coupling of subsequent nucleotides by the enzyme. The inhibitory group can be a charged group, such as a charged amino acid, or the inhibitory group can be a group that becomes charged depending upon the ambient conditions. In some embodiments, the inhibitor may include a moiety that is negatively charged or capable of becoming a negatively charged. For example, an inhibitor may include a chain of phosphate groups (e.g., 1, 2, or 3, phosphates) as shown in FIGS. 16A-C, wherein additional phosphates increase the overall anionic charge of the inhibitor. In other embodiments, the inhibitor group is positively charged or capable of becoming positively charged. In some other embodiments, the inhibitor is an amino acid or an amino acid analog. The inhibitor may be a peptide of 2 to 20 units of amino acids or analogs, a peptide of 2 to 10 units of amino acids or analogs, a peptide of 3 to 7 units of amino acids or analogs, a peptide of 3 to 5 units of amino acids or analogs. In some embodiments, the inhibitor includes a group selected from the group consisting of Glu, Asp, Arg, His, and Lys, and a combination thereof (e.g., Arg, Arg-Arg, Asp, Asp-Asp, Asp, Glu, Glu-Glu, Asp-Glu-Asp, Asp-Asp-Glu or AspAspAspAsp, etc.). Peptides or groups may be combinations of the same or different amino acids or analogs. In certain embodiments, a peptide inhibitor may be acetylated to discourage errant bonding of free amino groups. The inhibitory group may also include a group that reacts with residues in the active site of the enzyme thus interfering with the coupling of subsequent nucleotides by the enzyme. The inhibitor may have a charged group selected from the group consisting of —COO, —NO$_2$, —PO$_4$, —PO$_3$, —SO$_2$, or —NR$_3$ where each R may be H or an alkyl group. In other embodiments, the inhibitor moiety does not comprise a —PO$_4$ group.

In certain aspects, a terminator or inhibitor may include a steric inhibitor group. Such a steric inhibitor group may allow for the NTP-linker-inhibitor (i.e., nucleotide analog) to be incorporated onto the unblocked 3' OH of an oligonucleotide, said incorporation being catalyzed by nucleotidyl transferase. The steric inhibitor group may physically block the incorporation of nucleotides or additional nucleotide analogs onto the unblocked 3' OH of the incorporated nucleotide analog. Steric inhibitors may also block 3' endo-nucleases from acting on a nucleotide analog and, accordingly, on oligonucleotides to which an un-cleaved nucleotide analog has been incorporated.

Steric inhibitors can include, for example, chemical polymers, nanoparticles, poly-N-substituted glycines (peptoids), or proteins. A steric inhibitor of the invention may be a variety of sizes including, e.g., greater than 20 Å, greater than 30 Å, greater than 40 Å, greater than 50 Å, greater than 60 Å, greater than 70 Å, greater than 80 Å, greater than 90 Å, greater than 100 Å, greater than 110 Å, greater than 120 Å, greater than 130 Å, greater than 140 Å, or greater than 150 Å. In preferred embodiments, a steric inhibitor may be monodisperse or substantially monodisperse. Steric inhibitors may be water soluble and conformationally-constrained (i.e., of a rigid or semi-rigid form). In certain aspects, a steric inhibitor will physically block access to the active site of the relevant nucleotidyl transferase enzyme because of the size or the conformation of the inhibitor. In preferred embodiments, the steric inhibitor may comprise a non-natural bio-inspired polymer such as a polypeptoid or a non-natural polypeptide.

Figure 18:
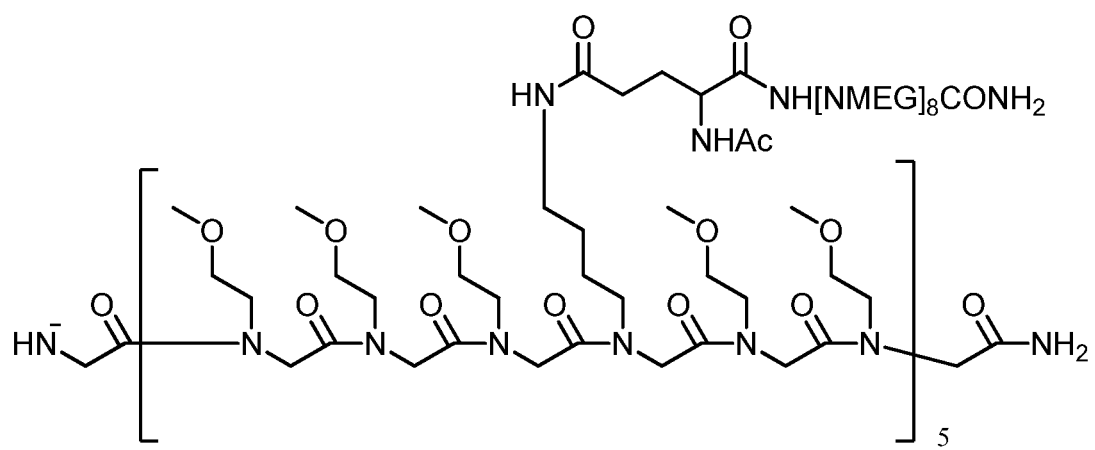
FIG. 18 shows an exemplary polypeptoid inhibitor suitable for use in the invention.

In certain aspects, a self-assembling polypeptoid sequence may be used as a steric inhibitor. Peptoid monomers are often based on an N-substituted glycine backbone. Because the backbone is devoid of hydrogen bond donors, polypeptoids are readily processed while still being able to form secondary structures such as helices. They also provide the beneficial properties of allowing polarities and side chains similar to peptides, while being generally chemically and thermally stable. Self-assembling polypeptoid steric inhibitors according to the invention may self-assemble single peptoid helices to form microspheres in the micrometer range of diameters including, 0.3 μm, 0.4 μm, 0.5 μm, 0.6 μm, 0.7 μm, 0.8 μm, 0.9 μm, 1.0 μm, 1.5 μm, 2 μm, 2.5 μm, 3 μm, or 3.5 μm, among others. In certain aspects, steric inhibitors may include peptoids with C-α-branched side chains, N-Aryl side chains, N-1-naphthylethyl side chains, or other formations capable of forming stable helical structures. An example of a peptoid steric inhibitor is shown in FIG. 18. FIG. 18 illustrates a branched poly-N-methoxyethyl glycine which may be used as a steric inhibitor according to the invention. In certain embodiments, a steric inhibitor may include a reactive group that is easily joined to a linker group, e.g., a cleavable linking group as described herein.

In other embodiments, a steric inhibitor may comprise a polymer, such as a biocompatible polymer. The polymer may comprise blocks of different polymers, such that the blocks form a desired macroscopic structure, e.g., a sphere when exposed to an aqueous environment. For example, the copolymer may comprise blocks of hydrophilic and hydrophobic blocks so that the polymer self-assembles into a micellar structure upon addition to water. In some embodiments, the hydrophobic blocks may be selected from polycaprolactones (PCL), polydimethylsiloxanes (PDMS), polymethylmethacrylate (PMMA), or polylactides (PLA). The hydrophilic blocks may include polyethylene glycol (PEG) or other polyalcohol.

In other embodiments, the inhibitor may comprise a nanoparticle of sufficient size to block the activity of a nucleotidyl transferase. Such nanoparticles may comprise, e.g., gold, silver, silicon, cerium oxide, iron oxide, titanium dioxide, silicon nitride, silicon boride, or silica, e.g., mesoporous silica. In other embodiments, the nanoparticles may comprise highly-ordered molecular structures, such as fullerenes, e.g., buckyballs and nanotubes, comprising carbon, or semiconductors.

Steric inhibitors may have no charge or may be positively or negatively charged to provide compatibility with the nucleotide to which it is linked and with the nucleotidyl transferase enzyme so that the inhibitor does not interfere with the incorporation reaction on the 5' end of the NTP analog. Steric inhibitors may incorporate a variety of amino acid residues in order to provide a desired conformation, charge, or attachment site.

Figure 1B:
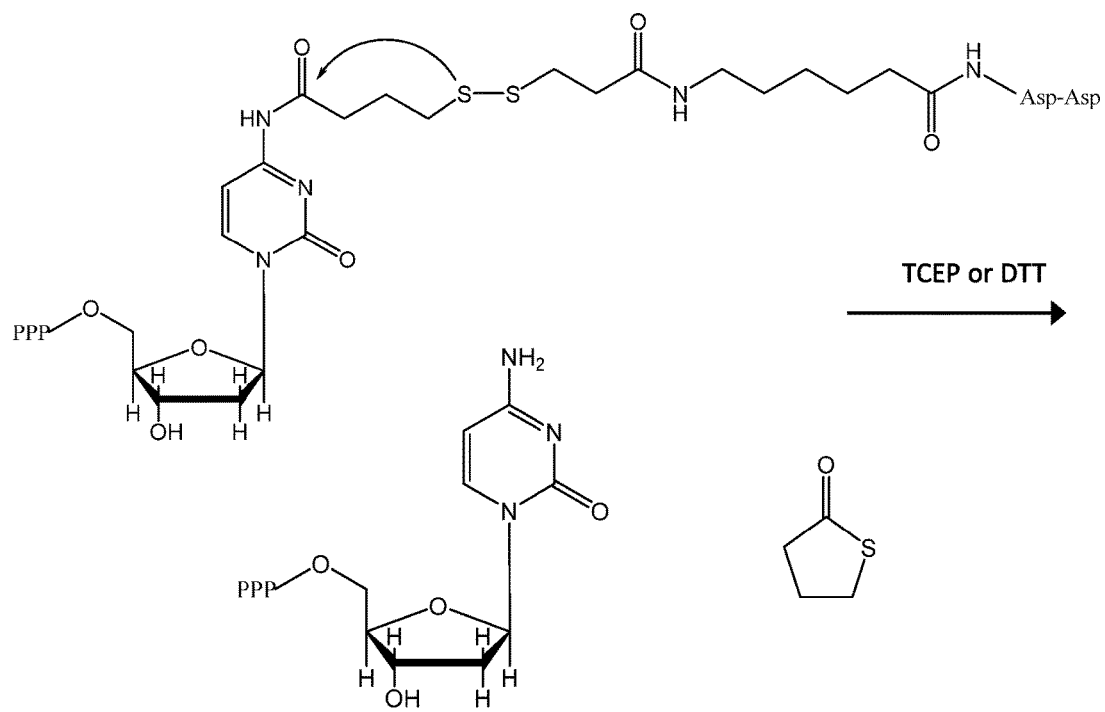
FIG. 1B shows cleavage of the cleavable terminator from a dCTP analog of FIG. 1A to achieve a "natural" dCTP and a cyclic leaving molecule.

An example of a nucleotide analog of the type NTP-linker-inhibitor is shown in FIG. 1A. The analog in FIG. 1A includes an inhibitory (-Asp-Asp-) group linked to the $N^4$ position of dCTP through a disulfide (—S—S—) bond while providing an unblocked, unmodified 3'-OH on the sugar ring. The linker is constructed such that all linker atoms (including the 2nd incorporation-inhibiting moiety) can be removed, thereby allowing the nascent DNA strand to revert to natural nucleotides. As shown in FIG. 1B, an aqueous reducing agent, such as tris(2-carboxyethyl) phosphine (TCEP) or dithiothreitol (DTT), can be used to cleave the —S—S— bond, resulting in the loss of the inhibitor function (deblocking). As shown in FIG. 1B, a self-cyclizing linker can be incorporated, resulting in a cyclic oxidized tetrahydrothiophene leaving group that is easily removed from the reagent solution at the conclusion of nucleotide synthesis.

Exemplary schemes for synthesizing dCTP analogs of FIG. 1A are shown below in Schemes 1A and 1B:

Scheme 1A

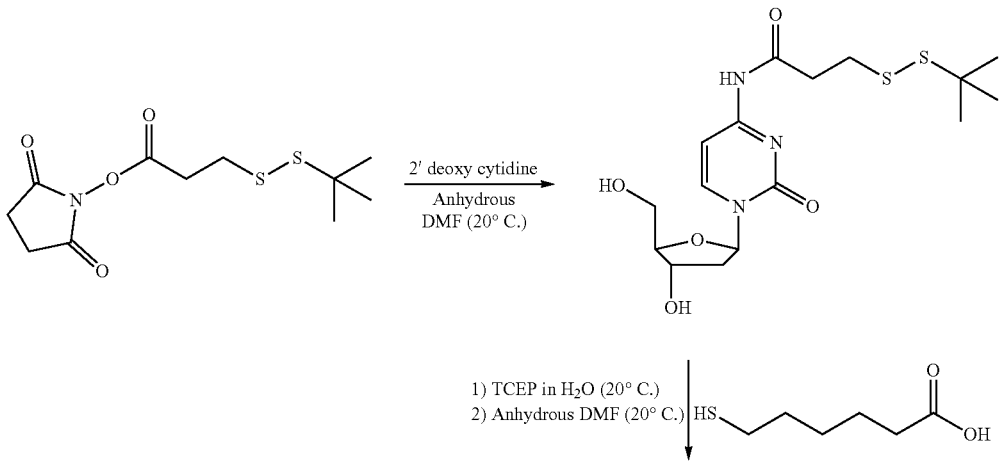

-continued
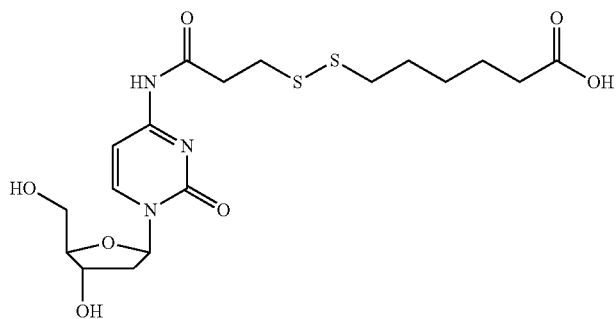
1) POCl₃ (20° C.)
2) PO(OCH₃)₃ (-15° C.-0° C.) | POCl₃/Pyrophosphate
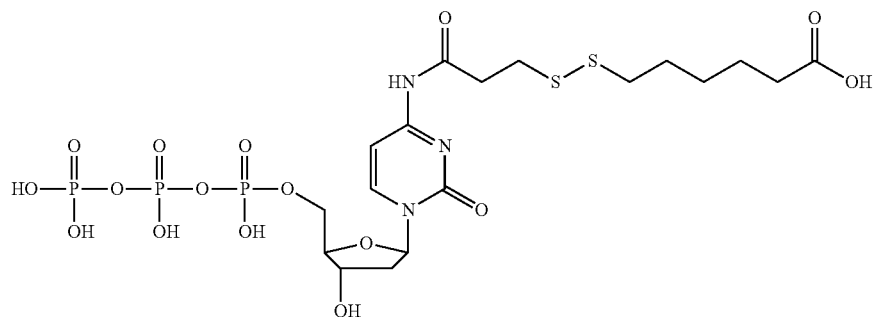
1) NHS/DCC
2) Asp-Asp
   Anhydrous DMF (20° C.)
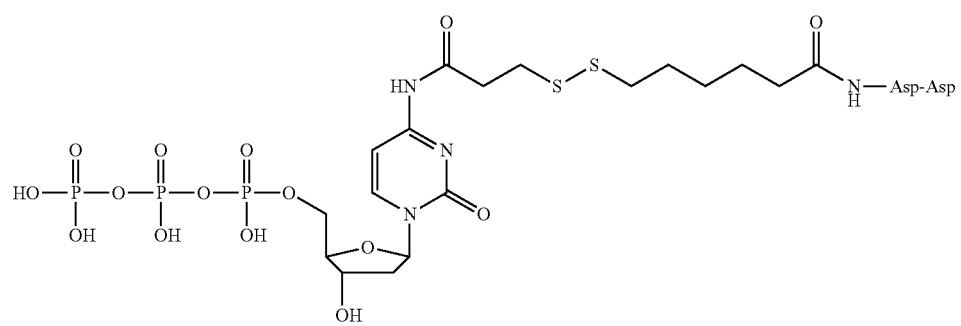

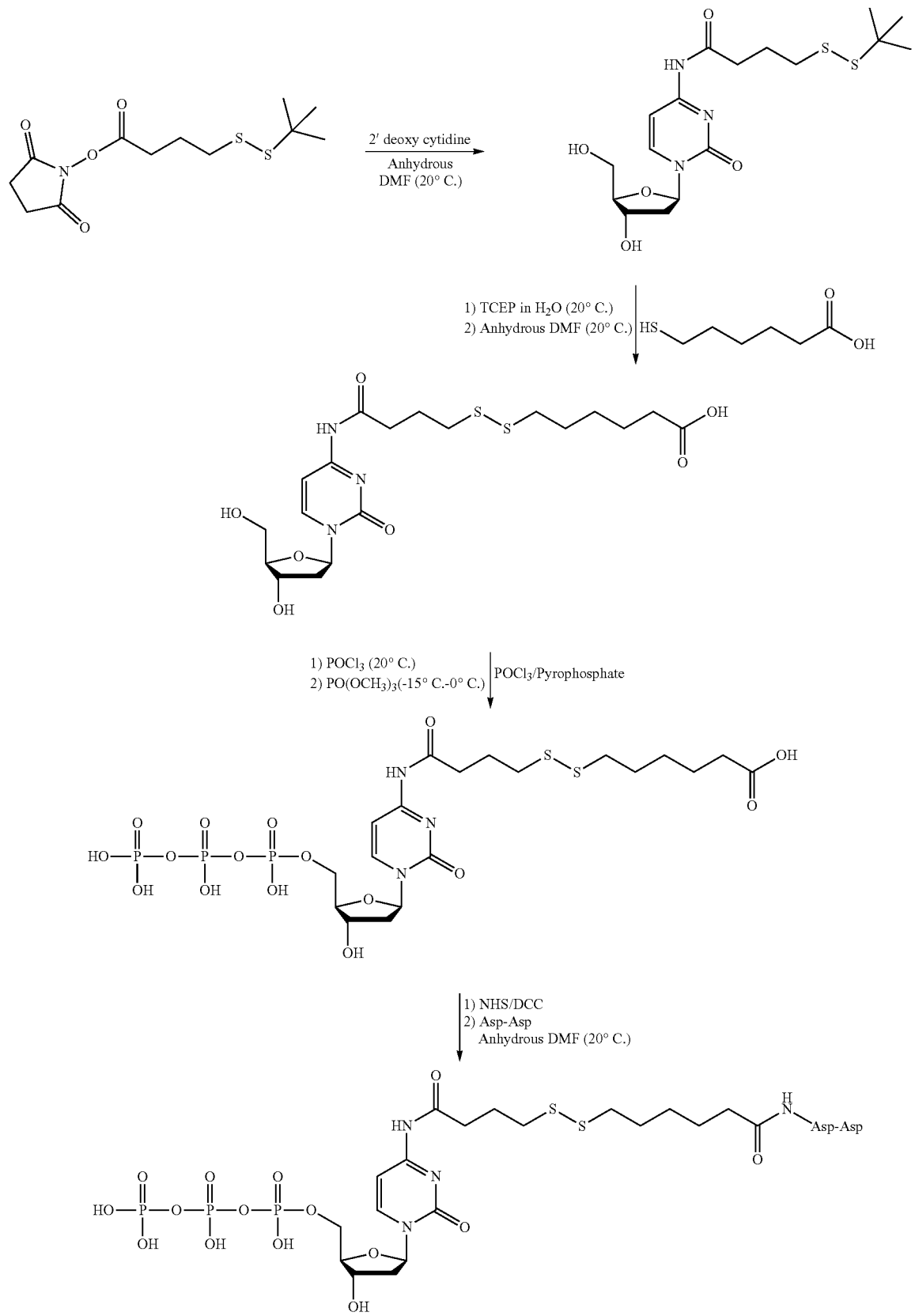
Scheme 1B

Figure 2A:
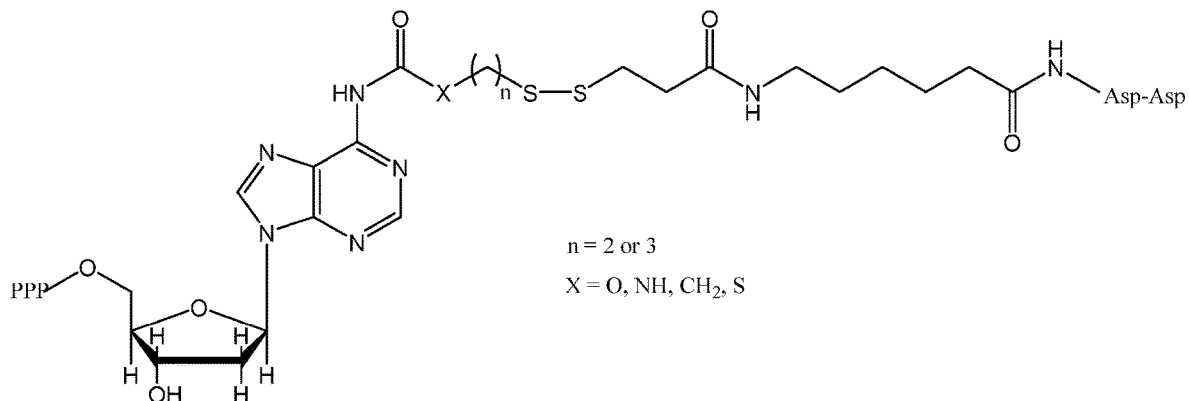
FIG. 2A shows a genus of deoxyadenosine triphosphate (dATP) analogs having a cleavable terminator linked at the N-6 position.
Figure 2B:
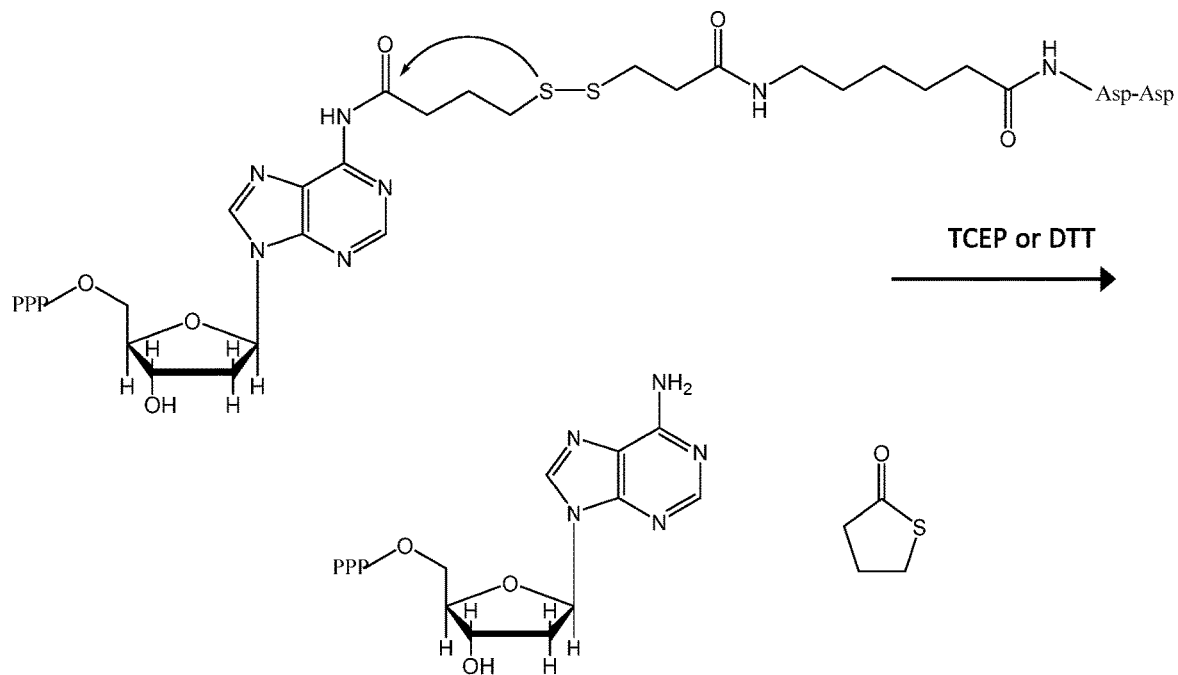
FIG. 2B shows cleavage of the cleavable terminator from a dATP analog of FIG. 2A to achieve a "natural" dATP and a cyclic leaving molecule.
Figure 3A:
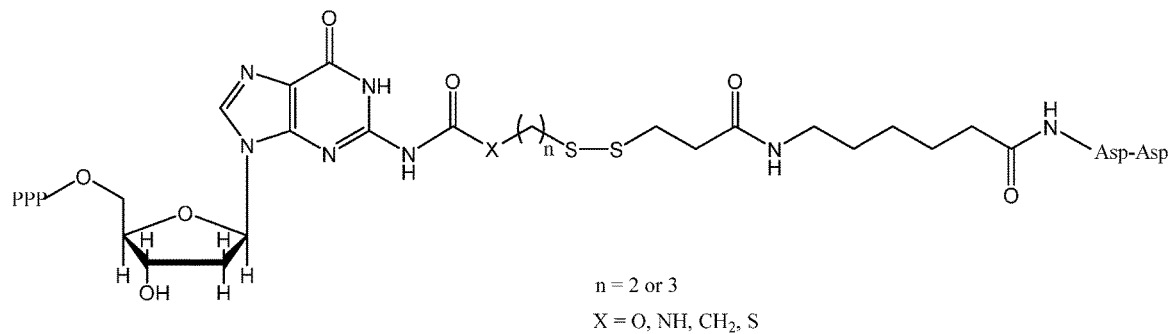
FIG. 3A shows a genus of deoxyguanosine triphosphate (dGTP) analogs having a cleavable terminator linked at the N-2 position.
Figure 3B:
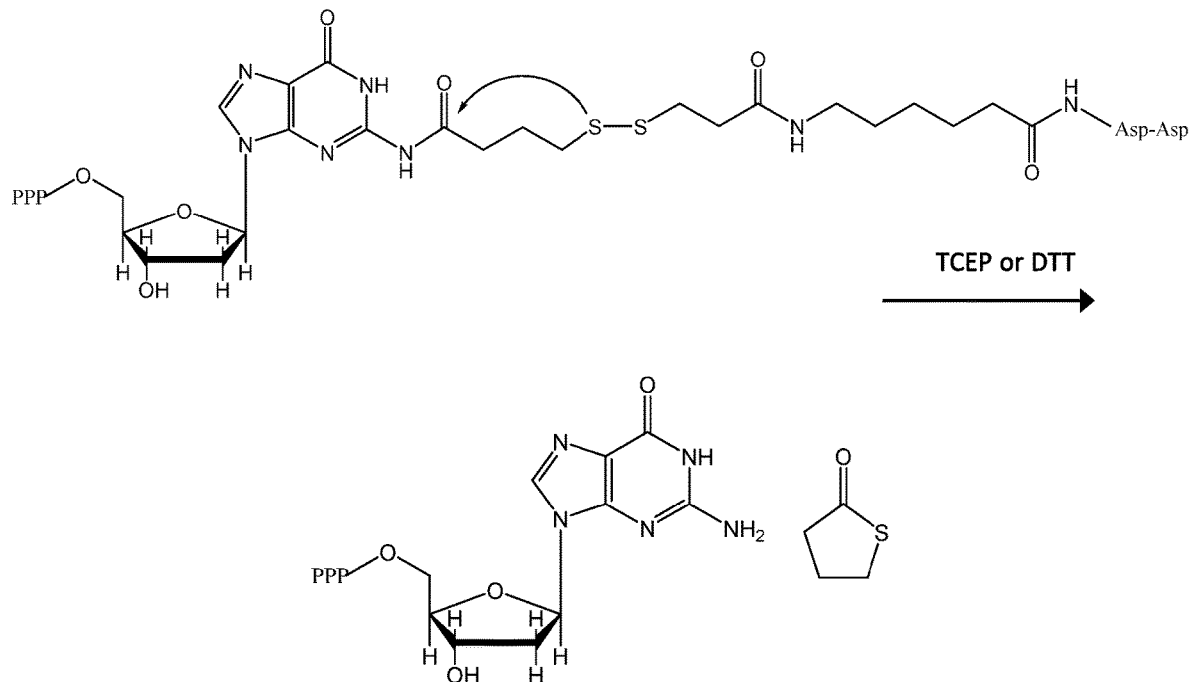
FIG. 3B shows cleavage of the cleavable terminator from a dGTP analog of FIG. 3A to achieve a "natural" dGTP and a cyclic leaving molecule.
Figure 4A:
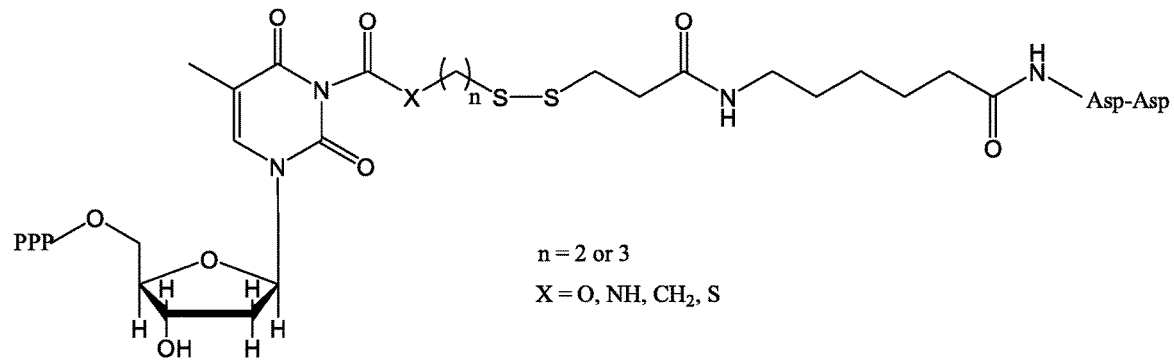
FIG. 4A shows a genus of deoxythymidine triphosphate (dTTP) analogs having a cleavable terminator linked at the N-3 position.
Figure 4B:
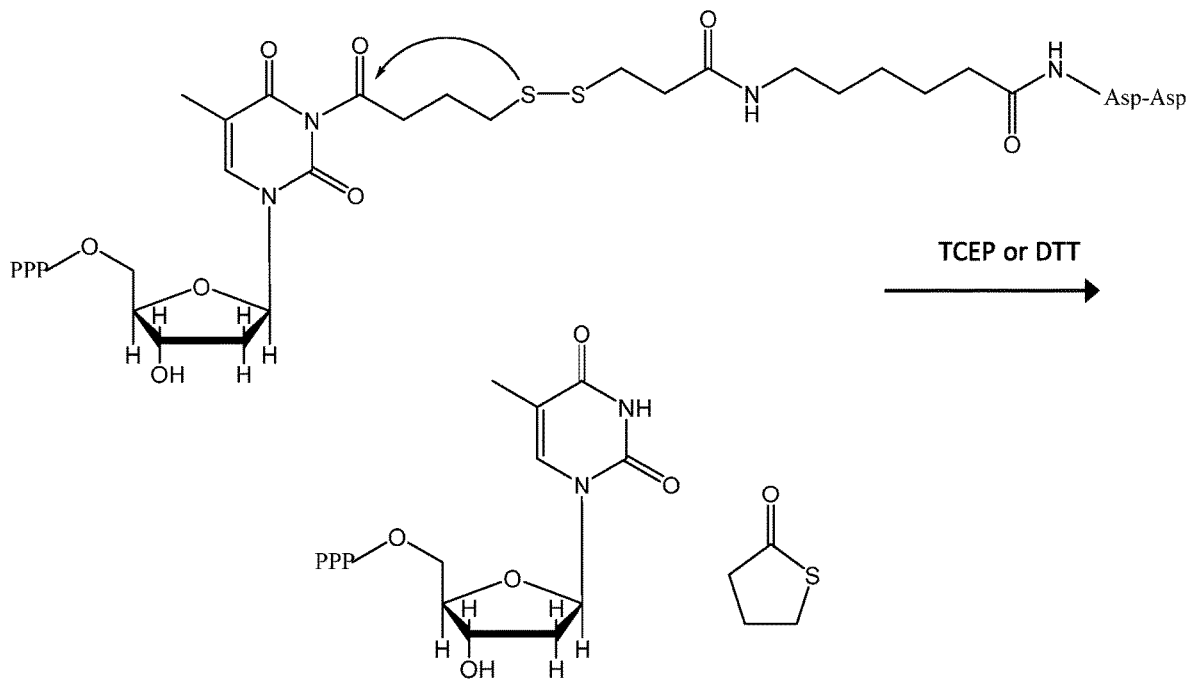
FIG. 4B shows cleavage of the cleavable terminator from a dTTP analog of FIG. 4A to achieve a "natural" dTTP and a cyclic leaving molecule.
Figure 5A:
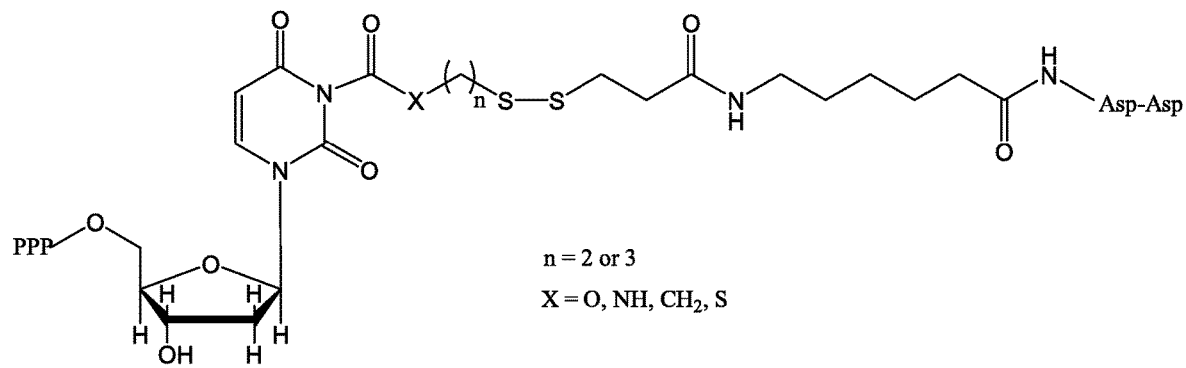
FIG. 5A shows a genus of deoxyuridine triphosphate (dUTP) analogs having a cleavable terminator linked at the N-3 position.
Figure 5B:
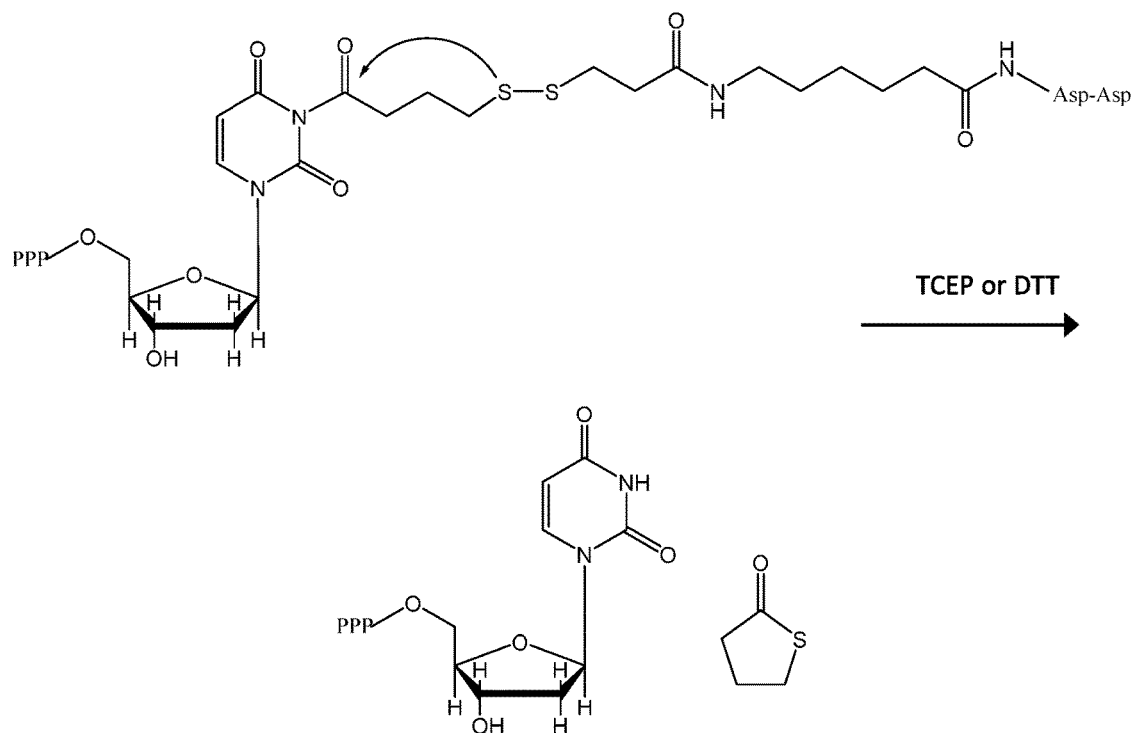
FIG. 5B shows cleavage of the cleavable terminator from a dUTP analog of FIG. 5A to achieve a dUTP and a cyclic leaving molecule.

In a fashion analogous to Schemes 1A and 1B, nucleotide analogs of the type NTP-linker-inhibitor can also be formed by attaching the linker-inhibitor moiety to the N6 of adenine (FIG. 2), the N2 of guanine (FIG. 3), the N3 of thymine (FIG. 4), or the N3 of uracil (FIG. 5), thereby providing analogs of the "naturally-occurring" dNTPs, as well as a deoxyuracil nucleotide (dUTP). While it is unlikely that there will be wide use of a dUTP, the synthesis is straightforward based upon the chemistry.

The invention is not limited to the linking chemistry of Schemes 1A and 1B, however, as carbamate, amide, or other self-eliminating linkages could also be employed. For example, nucleotides can also be prepared with Staudinger linkers, as shown in Scheme 2:

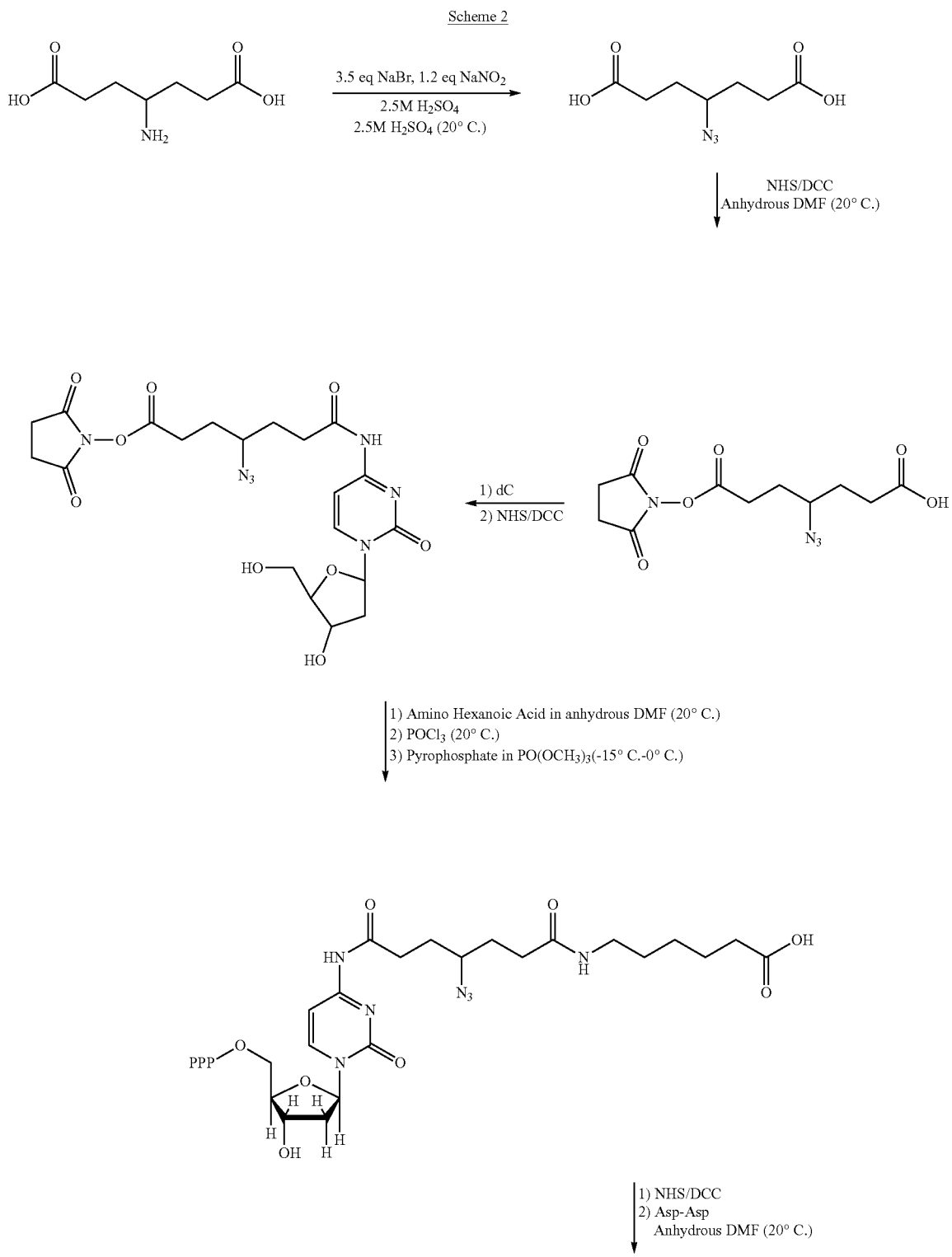

-continued

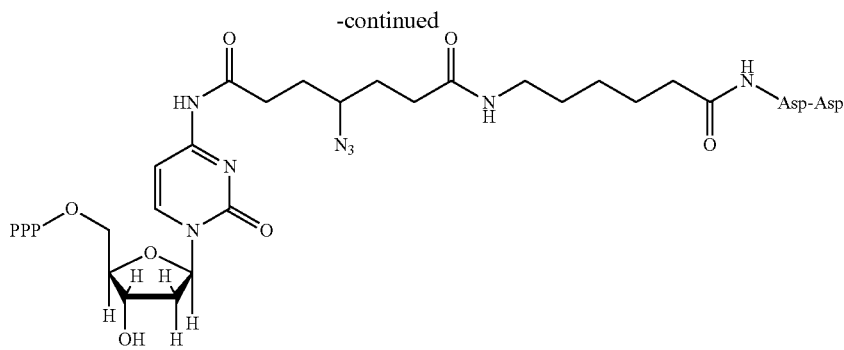

Figure 6:
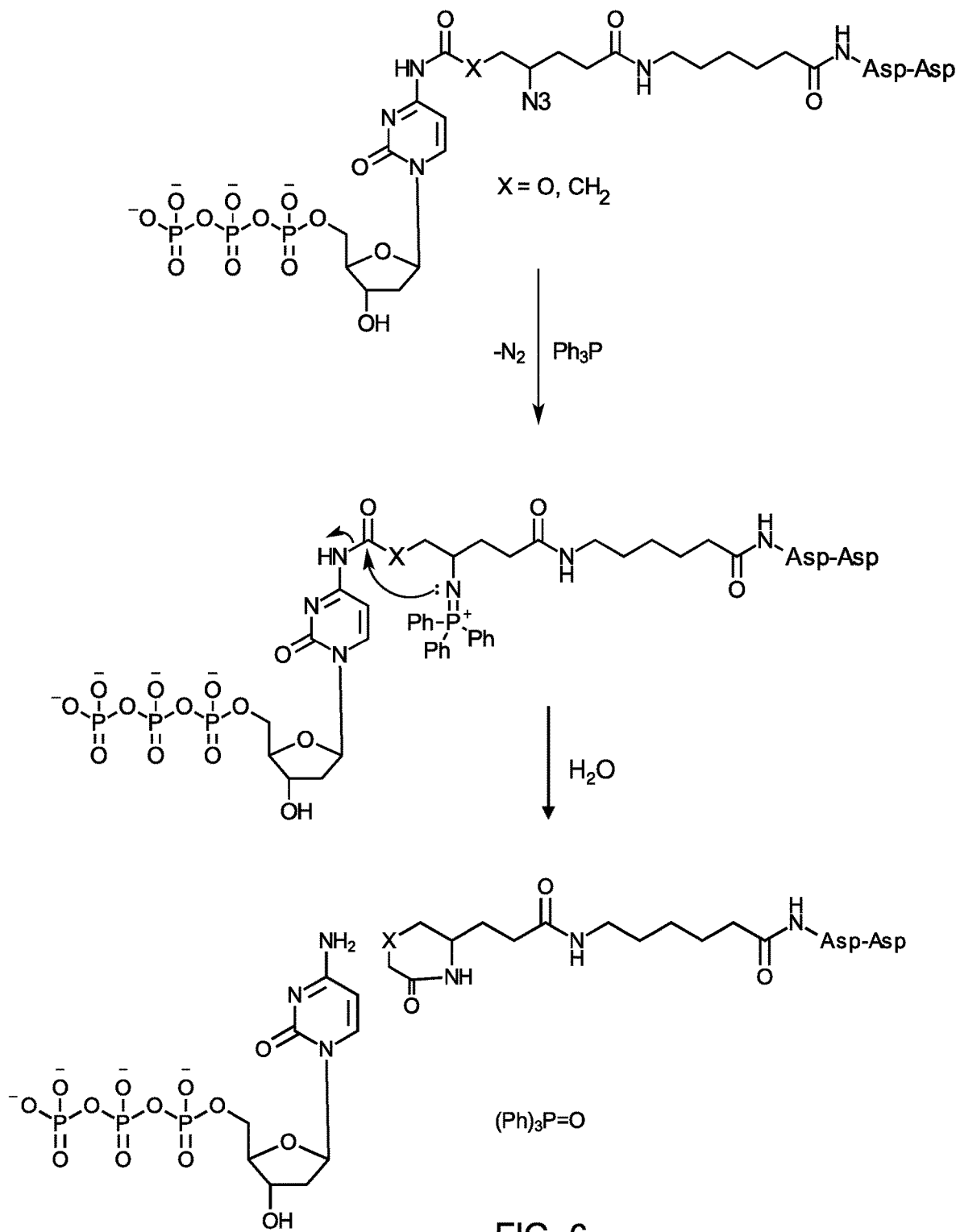
FIG. 6 shows an exemplary deoxycytidine triphosphate (dCTP) analog having a Staudinger linker connecting a blocking Asp-Asp molecule to the N-4 position of the deoxycytidine and subsequent cleavage of the Staudinger linker under aqueous conditions to achieve a dCTP and a leaving group.
Figure 7A:
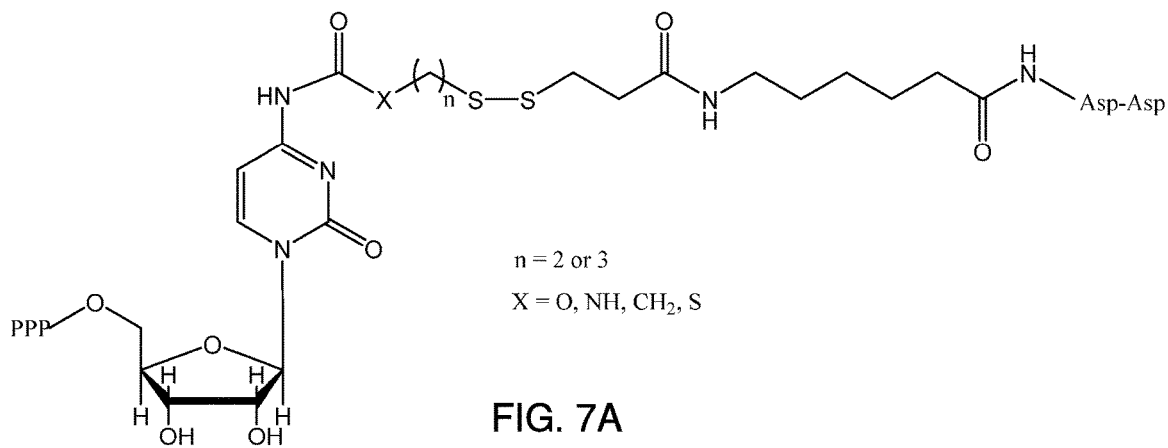
FIG. 7A shows a genus of cytidine triphosphate (rCTP) analogs having a cleavable terminator linked at the N-4 position.
Figure 7B:
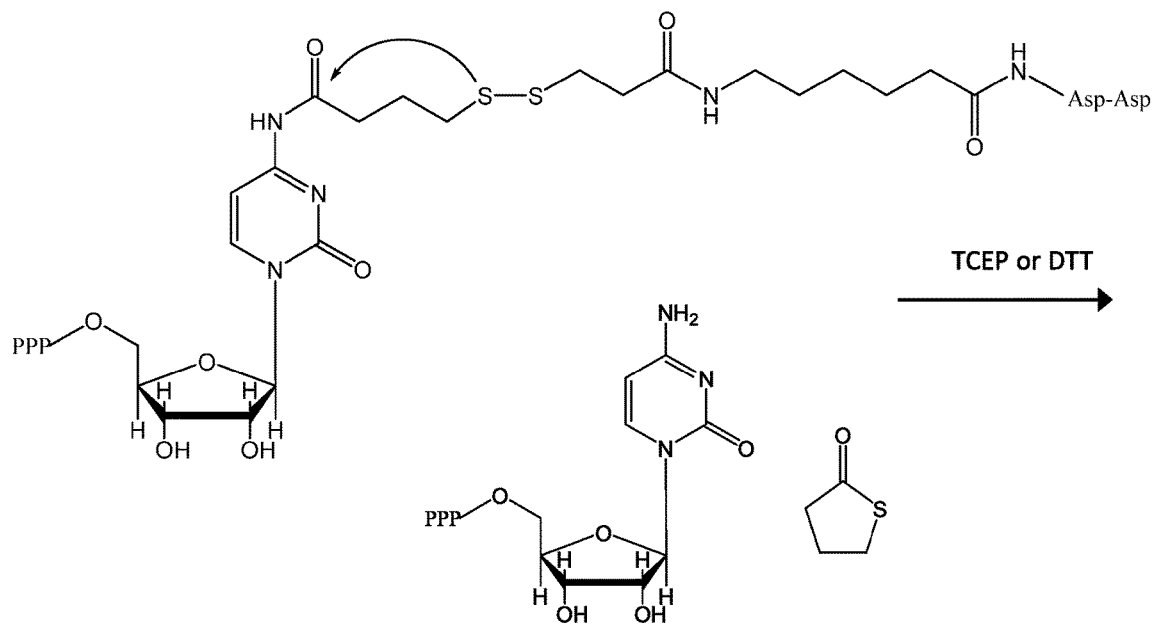
FIG. 7B shows cleavage of the cleavable terminator from a rCTP analog of FIG. 7A to achieve a "natural" rCTP and a cyclic leaving molecule.
Figure 8A:
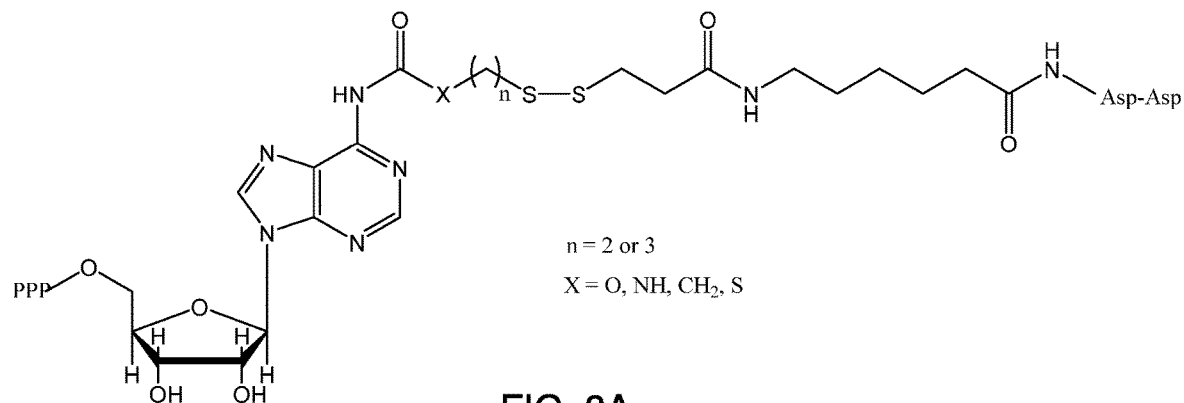
FIG. 8A shows a genus of adenosine triphosphate (rATP) analogs having a cleavable terminator linked at the N-6 position.
Figure 8B:
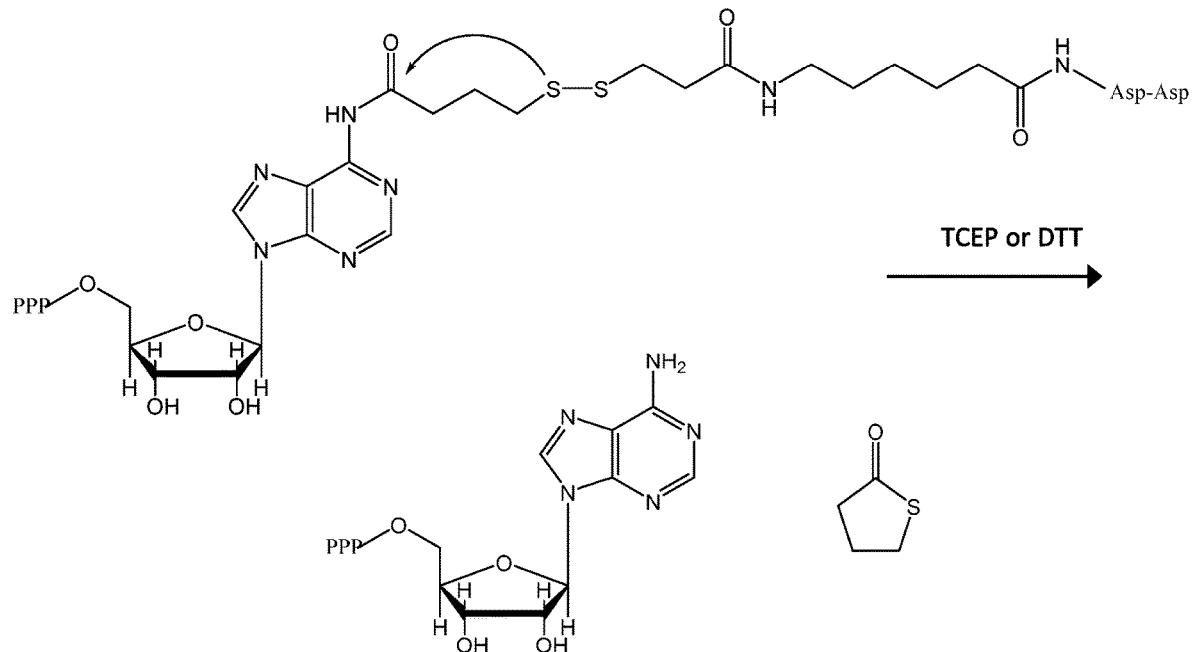
FIG. 8B shows cleavage of the cleavable terminator from an rATP analog of FIG. 8A to achieve a "natural" rATP and a cyclic leaving molecule.
Figure 9A:
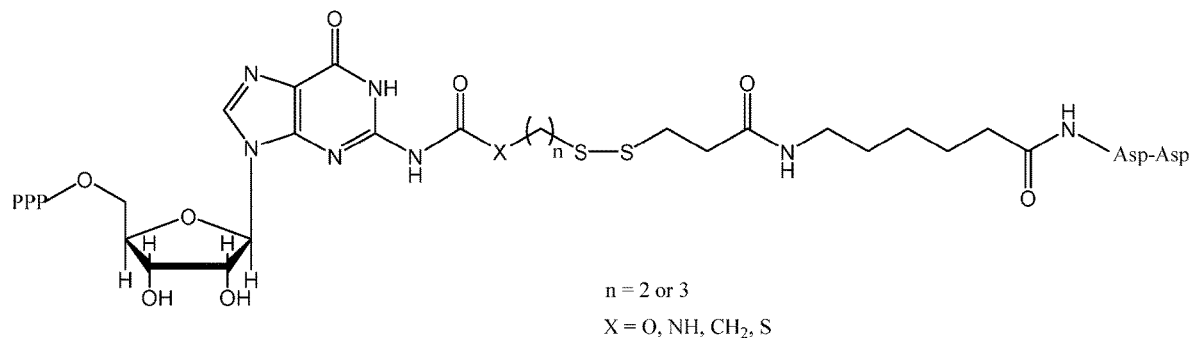
FIG. 9A shows n genus of guanosine triphosphate (rGTP) analogs having a cleavable terminator linked at the N-2 position.
Figure 9B:
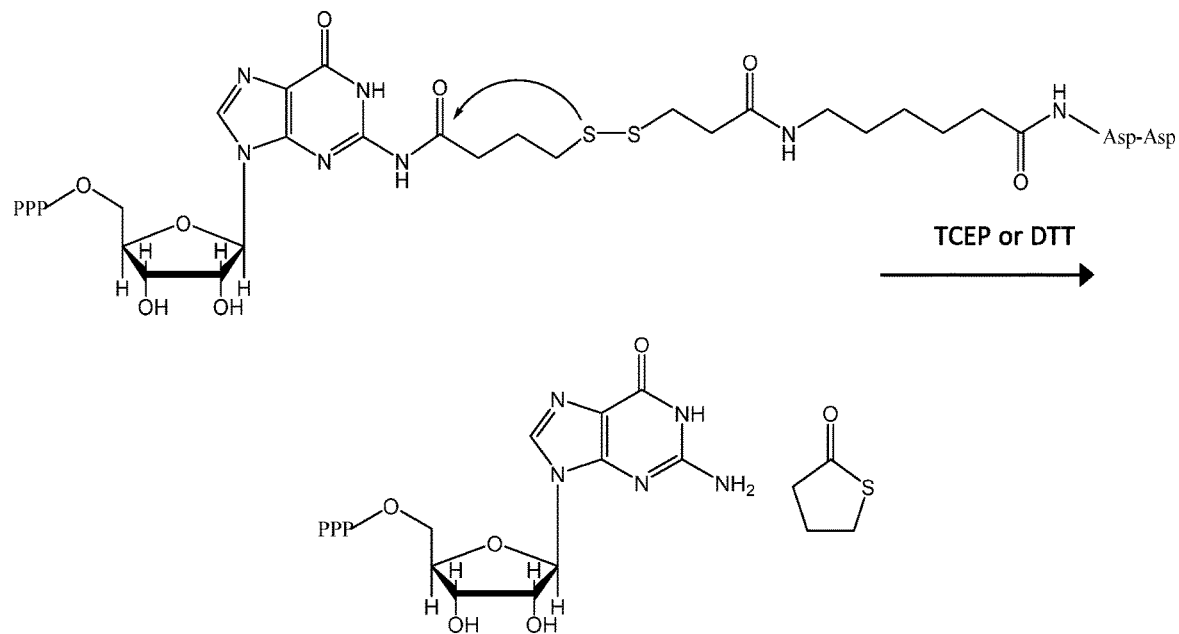
FIG. 9B shows cleavage of the cleavable terminator from a rGTP analog of FIG. 9A to achieve a "natural" rGTP and a cyclic leaving molecule.
Figure 10A:
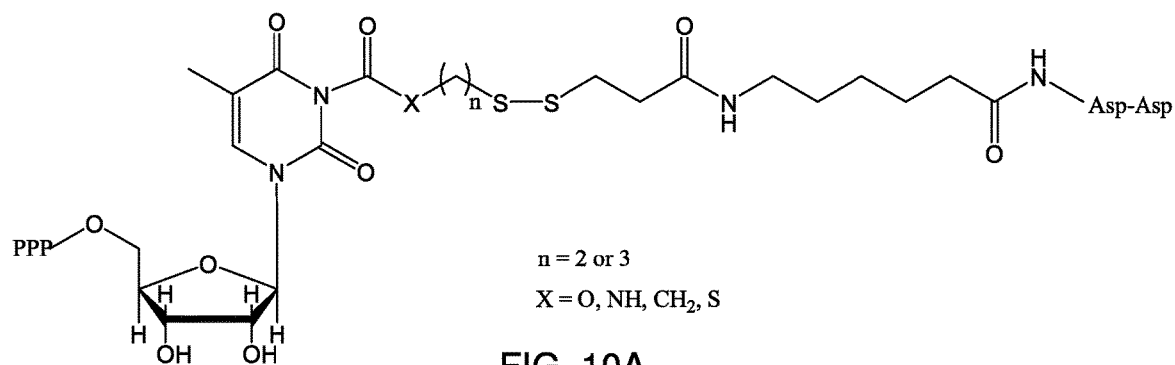
FIG. 10A shows a genus of thymidine triphosphate (rTTP) analogs having a cleavable terminator linked at the N-3 position.
Figure 10B:
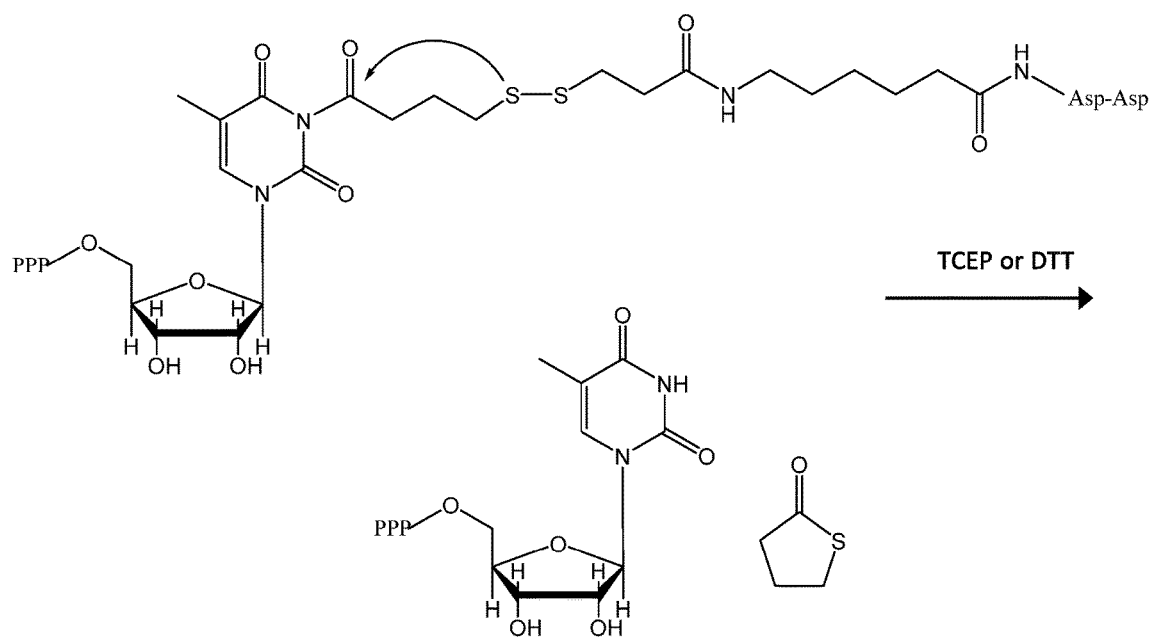
FIG. 10 shows cleavage of the cleavable terminator from a rTTP analog of FIG. 10A to achieve a "natural" rTTP and a cyclic leaving molecule.
Figure 11A:
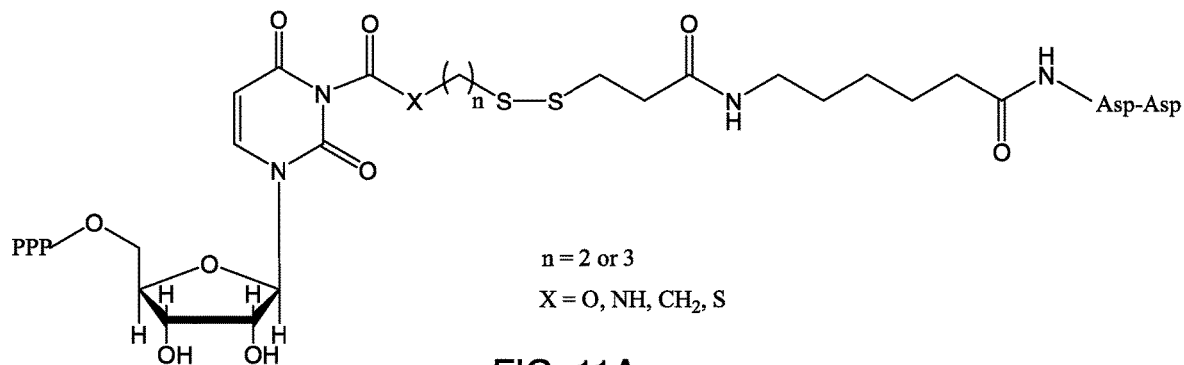
FIG. 11A shows a genus of uridine triphosphate (rUTP) analogs having a cleavable terminator linked at the N-3 position.
Figure 11B:
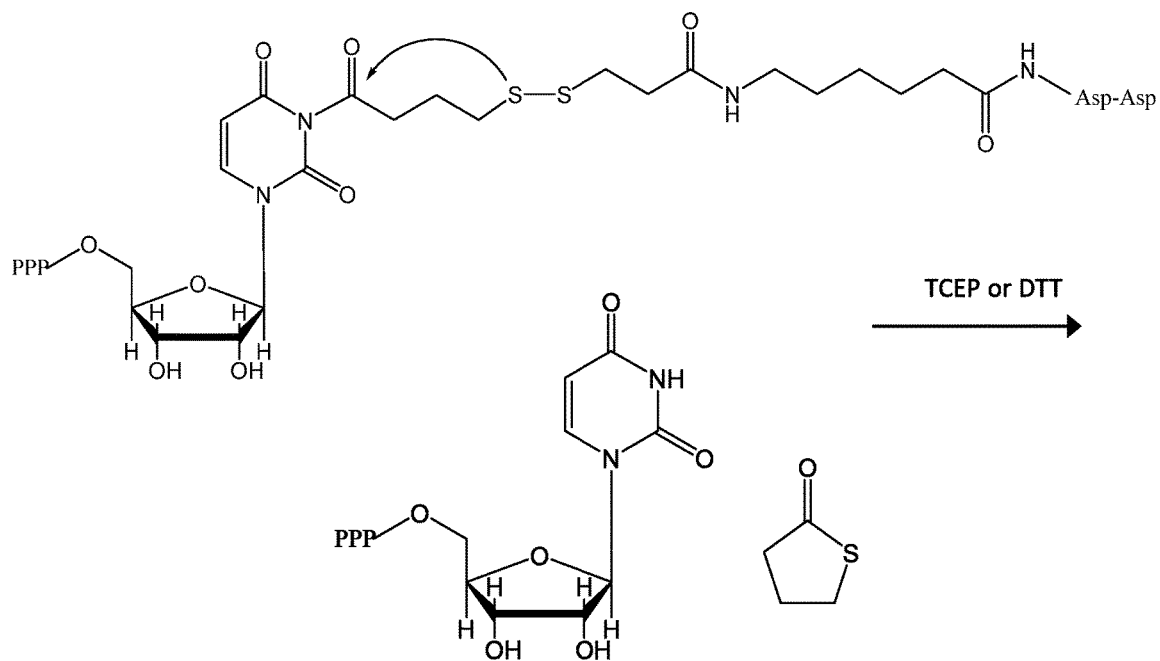

A deoxycytidine triphosphate (dCTP) analog created with a Staudinger linker (Scheme 2) to an Asp-Asp blocking group is shown in FIG. 6. As shown in FIG. 6, the Staudinger dCTP analog undergoes cleavage under aqueous conditions with the addition of azide and triphenylphosphine. The Staudinger analog shown in FIG. 6 is also suitable for nucleotide extension using nucleotidyl transferases, such as TdT, as described above and exemplified in FIGS. 1-5. While not shown explicitly in the FIGS., one of skill in the art can use Scheme 2 in conjunction with the suitable reactant to produce other nucleotide analogs having Staudinger linkers as needed for complete de novo nucleotide synthesis. In a fashion analogous to FIG. 6, nucleotide analogs of Scheme 2 can be formed by attaching the Staudinger moiety to the N6 of adenine, the N2 of guanine, the N3 of thymine, or the N3 of uracil, thereby providing analogs of the "naturally-occurring" dNTPs, as well as a deoxyuracil nucleotide (dUTP).

Figure 12:
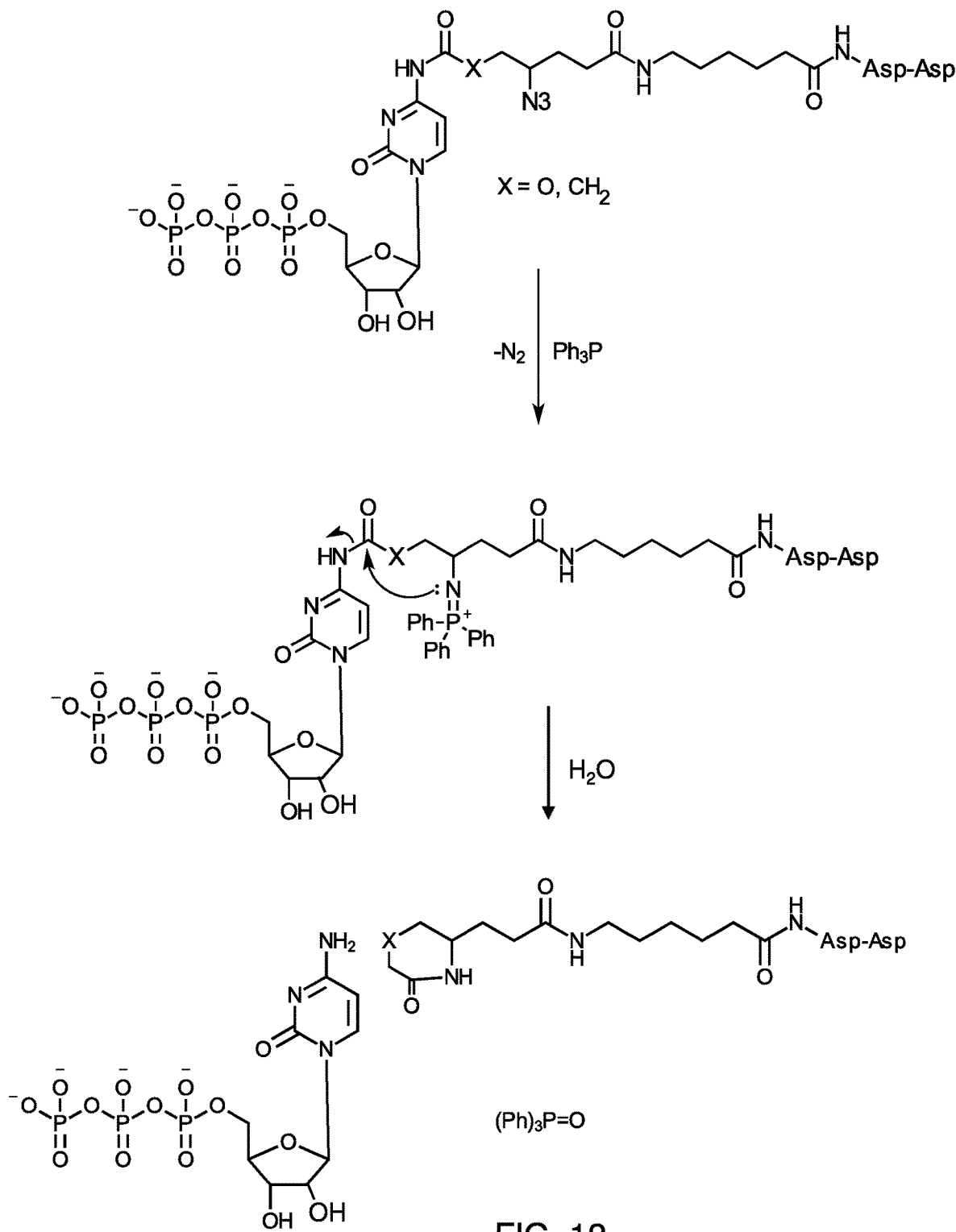
FIG. 12 shows an exemplary cytidine triphosphate (rCTP) analog having a Staudinger linker connecting a blocking Asp-Asp molecule to the N-4 position of the cytidine and subsequent cleavage of the Staudinger linker under aqueous conditions to achieve a rCTP and a leaving group.

The methodologies of Scheme 1A can be used to produce corresponding ribonucleotide analogs, e.g., as shown in FIGS. 7-10, by starting with the appropriate ribonucleotide reactants. Ribonucleotide analogs comprising the Staudinger linker can also be created using Scheme 2 in order to form the needed ribonucleotide analogs, including, e.g., CTP analogs, as shown in FIG. 12. Furthermore, all of the ribonucleotide analogs, i.e., C, A, T, G, U, can be formed using a reaction similar to Scheme 2.

Figure 20:
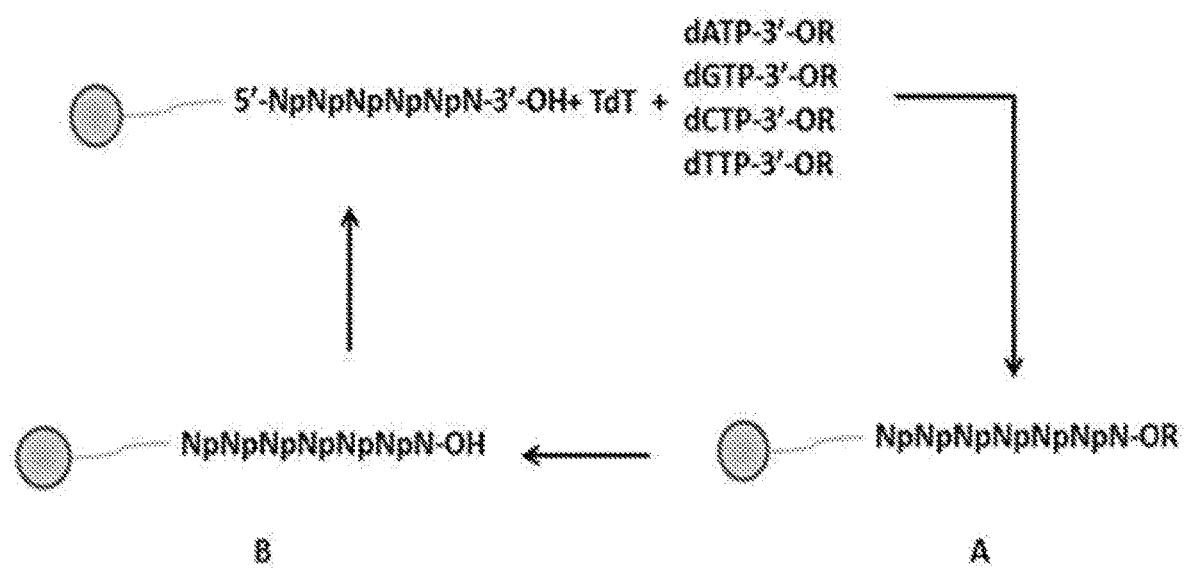
FIG. 20 illustrates synthesis of a de novo oligonucleotide using nucleotide triphosphate analogs having a 3'-O-blocking group.

In other embodiments, a 3-O-blocked nucleotide analog can be used along with a modified enzyme capable of incorporating 3-O-blocked nucleotide analogs into an oligonucleotide. Such modified enzymes will allow 3-O-blocked dNTP analogs to be used in a step-by-step method to extend an initiating nucleic acid into a user defined sequence (see FIG. 20). Furthermore, after each nucleotide extension step, the reactants can be recovered and recycled from the solid support back to the original reagent reservoir. Once that step is complete, the 3-O-blocking group will be removed, allowing the cycle to start anew. At the conclusion of n cycles of extension-recover-deblock-wash, the full length, single strand polydeoxynucleotide will be cleaved from the solid support and isolated for subsequent use. A variety of 3-O-blocked deoxynucleotides, may be used, but the choice of specific 3-O-blocking groups is dictated by: 1) the smallest possible bulk to maximize substrate utilization by TdT and 2) removal of the blocking group with the mildest and preferably aqueous conditions in the shortest period of time.

A variety of 3'-O-modified dNTPs and NTPs may be used with the disclosed proteins for de novo synthesis. In some embodiments, the preferred removable 3'-O-blocking group is a 3'-O-amino, a 3'-O-allyl or a 3'-O-azidomethyl. In other embodiments, the removable 3'-O-blocking moiety is selected from the group consisting of O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl (see U.S. Pat. No. 8,133,669). In other embodiments the removable blocking moiety is selected from the group consisting of esters, ethers, carbonitriles, phosphates, carbonates, carbamates, hydroxylamine, borates, nitrates, sugars, phosphoramide, phosphoramidates, phenylsulfenates, sulfates, sulfones and amino acids (see Metzker M L et al. Nuc Acids Res. 1994; 22(20):4259-67, U.S. Pat. Nos. 6,232, 465; 7,414,116; and 7,279,563, all of which are incorporated by reference in their entireties).

Figure 21:
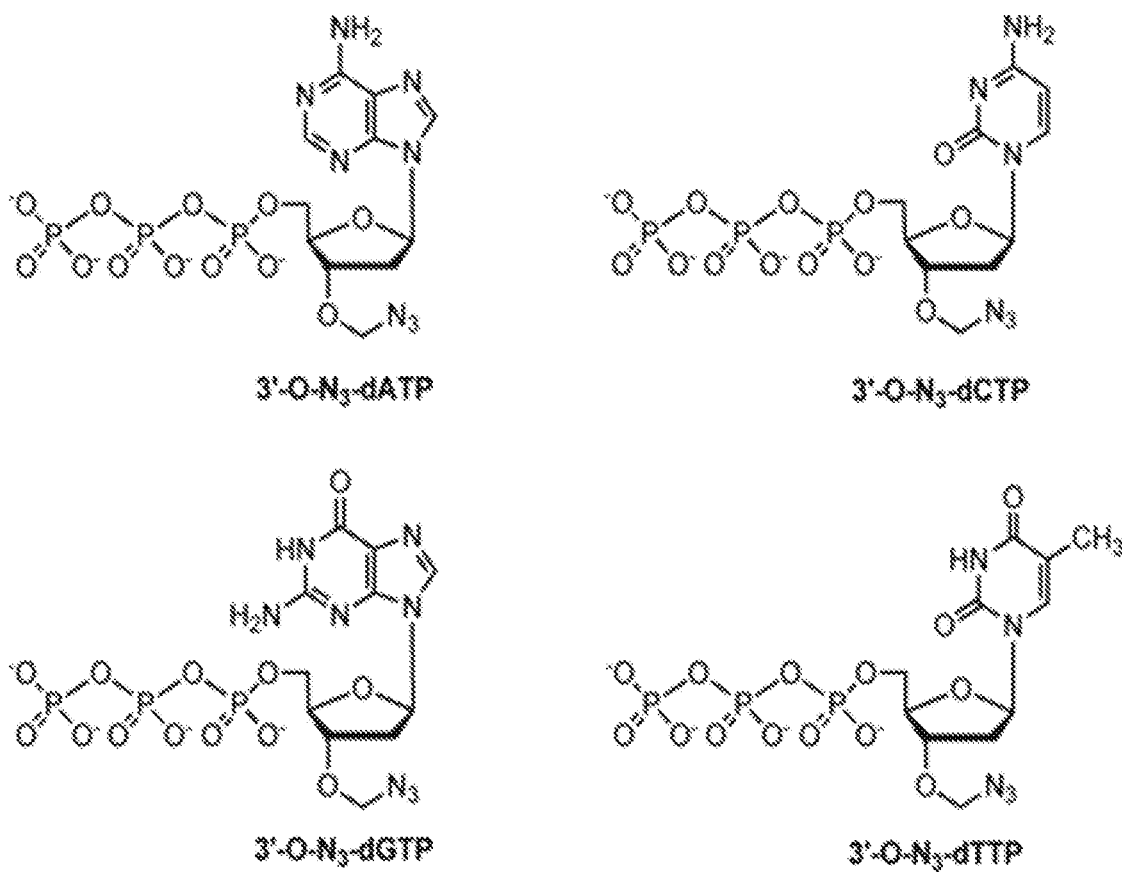
FIG. 21 shows four exemplary 3'-O-blocked nucleotide analogs that can be used for the synthesis of de novo oligonucleotides in conjunction with a suitable template-independent polymerase.

FIG. 21 shows four exemplary 3'-O-blocked dNTP analogs, namely 3'-O-azidomethyl-dATP, 3'-O-azidomethyl-dCTP, 3'-O-azidomethyl-dGTP, and 3'-O-azidomethyl-dTTP. The 3'-O-blocked dNTP analogs can be purchased from specialty suppliers, such as Azco Biotech, Oceanside, CA. Corresponding 3'-O-blocked ribonucleotides can also be obtained commercially, thus enabling the creation of custom RNA oligonucleotides.

In various embodiments, nucleotide analogs of the invention may have the following structure:

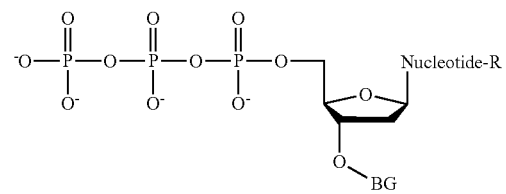

BG represents a 3'-O-blocking group such as the ones discussed above. In certain embodiments, the 3'-O-blocking group may be 3'-$ONO_2$, 3'-$OCH_2CH_2CN$, 3'-$OCH_2N_3$, 3'-$OPO_3$, 3'-$OCH_2SSCH_3$, and 3'-ONHC(O)H. The Nucleotide-R group may be any of the nucleotide groups discussed above including various linkers and blocking groups or other modifications. In certain embodiments, R may be an H, an amide, a carbamate, or a urea. Any of those R groups may be further linked a methyl, ethyl, propyl, isopropyl, isobutyl, pivaloyl, cyclohexyl, cyclopropyl, phenyl, naphthyl, anthracenyl, phenanthrenyl, pyrenyl, chrysenyl, pyridinyl, pyrimidinyl, pyrazinyl, indolyl, quinolinyl, isoquinolinyl, furanyl, thiophenyl, morpholinyl, piperidinyl, dioxanyl, tetrahydrofuranyl, or biotin.

The complete nucleotide-R group may comprise deoxyadenosine, deoxycytidine, deoxythymidine, deoxyguanosine, an N6-modified deoxyadenosine, an N4-modified deoxycytidine, an N1-modified deoxythymidine, an O6-modified deoxyguanosine, an N1-modified deoxyguanosine, or an N2-modified deoxyguanosine.

In various embodiments, the nucleotide analog may be only an N4-modified deoxycytidine or an O6, N1, or N2-modified deoxyguanosine, each further comprising of a 3'-O-blocking group.

In some embodiments, the nucleotide analog may be only an N4-modified deoxycytidine or a, N1-modified deoxythymidine, each further comprising a 3'-O-blocking group.

In some embodiments, the nucleotide analog may be only an N4-modified deoxycytidine or an N6-modified deoxyadenosine, each further comprised of a 3'-O-blocking group.

In some embodiments, the nucleotide analog may be only an O6, N1, or N2-modified deoxyguanosine, and an N6-modified deoxyadenosine or an N1-modified deoxythymidine, each further comprised of a 3'-O-blocking group.

Enzymes

The methods of the invention employ nucleotidyl transferases to assemble the nucleotide analogs into polynucleotides. Nucleotidyl transferases include several families of related transferase and polymerase enzymes. Some nucleotidyl transferases polymerize deoxyribonucleotides more efficiently than ribonucleotides, some nucleotidyl transferases polymerize ribonucleotides more efficiently than deoxyribonucleotides, and some nucleotidyl transferases polymerize ribonucleotides and deoxyribonucleotides at approximately the same rate.

Of particular import to the invention, transferases having polymerase activity, such as terminal deoxynucleotidyl transferase (TdT), are capable of catalyzing the addition of deoxyribonucleotides to the 3' end of a nucleotide chain, thereby increasing chain length in DNA nucleotides. TdT will only catalyze the addition of 1-2 ribonucleotides to the growing end of a DNA strand which could be useful in the construction of site specific DNA-RNA chimeric polynucleotides. In particular, calf thymus TdT, sourced from engineered *E. coli*, is suitable for use with the invention and available from commercial sources such as Thermo Scientific (Pittsburgh, PA). The amino acid sequence corresponding to calf TdT is listed in Table 1 as SEQ ID NO. 1.

TABLE 1

Amino Acid Sequence of Bovine TdT

```
SEQ ID NO. 1:
MAQQRQHQRL PMDPLCTASS GPRKKRPRQV GASMASPPHD
IKFQNLVLFI LEKKMGTTRR NFLMELARRK GFRVENELSD SVTHIVAENN
SGSEVLEWLQ VQNIRASSQL ELLDVSWLIE SMGAGKPVEI TGKHQLVVRT
DYSATPNPGF QKTPPLAVKK ISQYACQRKT TLNNYNHIFT DAFEILAENS
EFKENEVSYV TFMRAASVLK SLPFTIISMK DTEGIPCLGD KVKCIIEEII EDGESSEVKA
VLNDERYQSF KLFTSVFGVG LKTSEKWFRM GFRSLSKIMS DKTLKFTKMQ
KAGFLYYEDL VSCVTRAEAE AVGVLVKEAV WAFLPDAFVT MTGGFRRGKK
IGHDVDFLIT SPGSAEDEEQ LLPKVINLWE KKGLLLYYDL VESTFEKFKL
PSRQVDTLDH FQKCFLILKL HHQRVDSSKS NQQEGKTWKA IRVDLVMCPY
ENRAFALLGW TGSRQFERDI RRYATHERKM MLDNHALYDK TKRVFLKAES
EEEIFAHLGL DYIEPWERNA
```

The nucleotide sequence corresponding to calf TdT is listed in Table 2 as SEQ ID NO. 2.

TABLE 2

Nucleic Acid Sequence of Bovine TdT

```
SEQ ID NO. 2:
ctcttctgga gataccactt gatggcacag cagaggcagc atcagcgtct tcccatggat ccgctgtgca
cagcctcctc aggccctcgg aagaagagac ccaggcaggt gggtgcctca atggcctccc ctcctcatga catcaagttt
caaaatttgg tcctcttcat tttggagaag aaaatgggaa ccaccgcag aaacttcctc atggagctgg ctcgaaggaa
aggtttcagg gttgaaaatg agctcagtga ttctgtcacc cacattgtag cagaaaacaa ctctggttca gaggttctcg
agtggcttca ggtacagaac ataagagcca gctcgcagct agaactcctt gatgtctcct ggctgatcga aagtatggga
gcaggaaaac cagtggagat tacaggaaaa caccagcttg ttgtgagaac agactattca gctaccccaa acccaggctt
ccagaagact ccaccacttg ctgtaaaaaa gatctcccag tacgcgtgtc aaagaaaaac cactttgaac aactataacc
acatattcac ggatgccttt gagatactgg ctgaaaattc tgagtttaaa gaaaatgaag tctcttatgt gacatttatg agagcagctt
ctgtacttaa atctctgcca ttcacaatca tcagtatgaa ggatacagaa ggaattccct gcctggggga caggtgaag
tgtatcatag aggaaattat tgaagatgga gaaagttctg aagttaaagc tgtgttaaat gatgaacgat atcagtcctt caaactcttt
acttctgttt ttggagtggg actgaagaca tctgagaaat ggttcaggat ggggttcaga tctctgagta aaataatgtc
agacaaaacc ctgaaattca caaaaatgca gaaagcagga tttctctatt atgaagacct tgtcagctgc gtgaccaggg
ccgaagcaga ggcggttggc gtgctggtta aagaggctgt gtgggcattt ctgccggatg cctttgtcac catgacagga
ggattccgca ggggtaagaa gattgggcat gatgtagatt ttttaattac cagcccagga tcagcagagg atgaagagca
acttttgcct aaagtgataa acttatggga aaaaaggga ttactttat attatgacct tgtggagtca acatttgaaa agttcaagtt
gccaagcagg caggtggata cttagatca ttttcaaaaa tgctttctga ttttaaaatt gcaccatcag agagtagaca gtagcaagtc
caaccagcag gaaggaaaga cctggaaggc catccgtgtg gacctggtta tgtgcccta cgagaaccgt gcctttgccc
tgctaggctg gactggctcc cggcagtttg agagagacat ccggcgctat gccacacacg agcggaagat gatgctggat
aaccacgctt tatatgacaa gaccaagagg gtatttctca aagcggaaag tgaagaagaa atctttgcac atctgggatt
ggactacatt gaacatggg aaagaaatgc ttaggagaaa gctgtcaact tttttcttt ctgttcttt tttcaggtta gacaaattat
gcttcatatt ataatgaaag atgccttagt caagtttggg attctttaca ttttaccaag atgtagattg cttctagaaa taagtagttt
tggaaacgtg atcaggcacc ccctgggtta tgctctggca agccatttgc aggactgatg tgtagaactc gcaatgcatt
ttccataaa acagtgttgg aattggtggc tcatttccag ggaagttcat caaagcccac tttgcccaca gtgtagctga aatactgtat
acttgccaat aaaaatagga aac
```

While commercially-available TdT is suitable for use with the methods of the invention, modified TdT, e.g., having an amino acid sequence at least 95% in common with SEQ ID NO. 1, e.g., having an amino acid sequence at least 98% in common with SEQ ID NO. 1, e.g., having an amino acid sequence at least 99% in common with SEQ ID NO. 1, may be used with the methods of the invention. An organism that expresses a suitable nucleotidyl transferase may comprise a nucleic acid sequence at least 95% in common with SEQ ID NO. 2, e.g., at least 98% in common with SEQ ID NO. 2, e.g., at least 99% in common with SEQ ID NO. 2. In some instances, a modified TdT will result in more efficient generation of polynucleotides, or allow better control of chain length. Other modifications to the TdT may change the release characteristics of the enzyme, thereby reducing the need for aqueous reducing agents such as TCEP or DTT.

For the synthesis of RNA polynucleotides, a nucleotidyl transferase like *E. coli* poly(A) polymerase can be used to catalyze the addition of ribonucleotides to the 3' end of a ribonucleotide initiator. In other embodiments, *E. coli* poly (U) polymerase may be more suitable for use with the methods of the invention. Both *E. coli* poly(A) polymerase and *E. coli* poly(U) polymerase are available from New England Biolabs (Ipswich, MA). These enzymes may be used with 3'unblocked reversible terminator ribonucleotide triphosphates (rNTPs) to synthesize RNA. In certain embodiments, RNA may be synthesized using 3'blocked, 2'blocked, or 2'-3'blocked rNTPs and poly(U) polymerase or poly(A) polymerase. The amino acid and nucleotide sequences for *E. coli* Poly(A) polymerase and *E. coli* Poly(U) polymerase are reproduced below. Modified *E. coli* Poly(A) polymerase or *E. coli* Poly(U) polymerase may be suitable for use with the methods of the invention. For example, an enzyme, having an amino acid sequence at least 95% in common with SEQ ID NO. 3, e.g., having an amino acid sequence at least 98% in common with SEQ ID NO. 3, e.g., having an amino acid sequence at least 99% in common with SEQ ID NO. 3, may be used with the methods of the invention. An organism that expresses a suitable enzyme may comprise a nucleic acid sequence at least 95% in common with SEQ ID NO. 4, e.g., at least 98% in common with SEQ ID NO. 4, e.g., at least 99% in common with SEQ ID NO. 4. Alternatively, an enzyme having an amino acid sequence at least 95% in common with SEQ ID NO. 5, e.g., having an amino acid sequence at least 98% in common with SEQ ID NO. 5, e.g., having an amino acid sequence at least 99% in common with SEQ ID NO. 5, may be used with the methods of the invention. An organism that expresses a suitable enzyme may comprise a nucleic acid sequence at least 95% in common with SEQ ID NO. 6, e.g., at least 98% in common with SEQ ID NO. 6, e.g., at least 99% in common with SEQ ID NO. 6.

TABLE 3

Amino Acid Sequence of *E. coli* Poly(A) polymerase

```
SEQ ID NO. 3:
MFTRVANFCR KVLSREESEA EQAVARPQVT VIPREQHAIS
RKDISENALK VMYRLNKAGY EAWLVGGGVR DLLLGKKPKD FDVTTNATPE
QVRKLFRNCR LVGRRFRLAH VMFGPEIIEV ATFRGHHEGN VSDRTTSQRG
QNGMLLRDNI FGSIEEDAQR RDFTINSLYY SVADFTVRDY VGGMKDLKDG
VIRLIGNPET RYREDPVRML RAVRFAAKLG MRISPETAEP IPRLATLLND IPPARLFEES
LKLLQAGYGY ETYKLLCEYH LFQPLFPTIT RYFTENGDSP MERIIEQVLK
NTDTRIHNDM RVNPAFLFAA MFWYPLLETA QKIAQESGLT YHDAFALAMN
DVLDEACRSL AIPKRLTTLT RDIWQLQLRM SRRQGKRAWK LLEHPKFRAA
YDLLALRAEV ERNAELQRLV KWWGEFQVSA PPDQKGMLNE LDEEPSPRRR
TRRPRKRAPR REGTA
```

The nucleotide sequence corresponding to *E. coli* poly(A) polymerase is listed in Table 4 as SEQ ID NO. 4.

TABLE 4

Nucleotide Sequence of *E. coli* Poly(A) polymerase

```
SEQ ID NO. 4:
atttttaccc gagtcgctaa tttttgccgc aaggtgctaa gccgcgagga aagcgaggct gaacaggcag
tcgcccgtcc acaggtgacg gtgatcccgc gtgagcagca tgctatttcc cgcaaagata tcagtgaaaa tgccctgaag
gtaatgtaca ggctcaataa agcgggatac gaagcctggc tggttggcgg cggcgtgcgc gacctgttac ttggcaaaaa
gccgaaagat tttgacgtaa ccactaacgc cacgcctgag caggtgcgca aactgttccg taactgccgc ctggtgggtc
gccgtttccg tctggctcat gtaatgtttg gcccggagat tatcgaagtt gcgaccttcc gtggacacca cgaaggtaac
gtcagcgacc gcacgacctc ccaacgcggg caaaacggca tgttgctgcg cgacaacatt ttcggctcca tcgaagaaga
cgcccagcgc cgcgatttca ctatcaacag cctgtattac agcgtagcgg attttaccgt ccgtgattac gttggcggca
tgaaggatct gaaggacggc gttatccgtc tgattggtaa cccggaaacg cgctaccgtg aagatccggt acgtatgctg
cgcgcggtac gttttgccgc caaattgggt atgcgcatca gcccggaaac cgcagaaccg atccctcgcc tcgctaccct
gctgaacgat atcccaccgg cacgcctgtt tgaagaatcg cttaaactgc tacaagcggg ctacggttac gaaacctata
agctgttgtg tgaatatcat ctgttccagc cgctgttccc gaccattacc cgctacttca cggaaaatgg cgacagcccg
atggagcgga tcattgaaca ggtgctgaag aataccgata cgcgtatcca taacgatatg cgcgtgaacc cggcgttcct
gtttgccgcc atgttctggt acccactgct ggagacggca cagaagatcg cccaggaaag cggcctgacc tatcacgacg
ctttcgcgct ggcgatgaac gacgtgctgg acgaagcctg ccgttcactg gcaatcccga aacgtctgac gacattaacc
cgcgatatct ggcagttgca gttgcgtatg tcccgtcgtc agggtaaacg cgcatggaaa ctgctggagc atcctaagtt
ccgtgcggct tatgacctgt tggccttgcg agctgaagtt gagcgtaacg ctgaactgca gcgtctggtg aaatggtggg
gtgagttcca ggtttccgcg ccaccagacc aaaaagggat gctcaacgag ctggatgaag aaccgtcacc gcgtcgtcgt
actcgtcgtc cacgcaaacg cgcaccacgt cgtgagggta ccgcatga
```

TABLE 5

Amino Acid Sequence of E. coli Poly(U) polymerase

SEQ ID NO. 5:
GSHMSYQKVP NSHKEFTKFC YEVYNEIKIS DKEFKEKRAA
LDTLRLCLKR ISPDAELVAF GSLESGLALK NSDMDLCVLM DSRVQSDTIA
LQFYEELIAE GFEGKFLQRA RIPIIKLTSD TKNGFGASFQ CDIGFNNRLA IHNTLLLSSY
TKLDARLKPM VLLVKHWAKR KQINSPYFGT LSSYGYVLMV LYYLIHVIKP
PVFPNLLLSP LKQEKIVDGF DVGFDDKLED IPPSQNYSSL GSLLHGFFRF
YAYKFEPREK VVTFRRPDGY LTKQEKGWTS ATEHTGSADQ IIKDRYILAI
EDPFEISHNV GRTVSSSGLY RIRGEFMAAS RLLNSRSYPI PYDSLFEEA

The nucleotide sequence corresponding to E. coli poly(U) polymerase is listed in Table 6 as SEQ ID NO. 6.

TABLE 6

Nucleotide Sequence of E. coli Poly(A) polymerase

SEQ ID NO. 6:
ggcagccata tgagctatca gaaagtgccg aacagccata aagaatttac caaattttgc tatgaagtgt
ataacgaaat taaaattagc gataaagaat ttaaagaaaa acgcgcggcg ctggataccc tgcgcctgtg cctgaaacgc
attagcccgg atgcggaact ggtggcgttt ggcagcctgg aaagcggcct ggcgctgaaa aacagcgata tggatctgtg
cgtgctgatg gatagccgcg tgcagagcga taccattgcg ctgcagtttt atgaagaact gattgcggaa ggctttgaag
gcaaatttct gcagcgcgcg cgcattccga ttattaaact gaccagcgat accaaaaacg gctttggcgc gagctttcag
tgcgatattg gctttaacaa ccgcctggcg attcataaca ccctgctgct gagcagctat accaaactgg atgcgcgcct
gaaaccgatg gtgctgctgg tgaaacattg ggcgaaacgc aaacagatta acagcccgta ttttggcacc ctgagcagct
atggctatgt gctgatggtg ctgtattatc tgattcatgt gattaaaccg ccggtgtttc cgaacctgct gctgagcccg ctgaaacagg
aaaaaattgt ggatggcttt gatgtgggct ttgatgataa actggaagat attccgccga gccagaacta tagcagcctg
ggcagcctgc tgcatggcct ttttcgcttt tatgcgtata aatttgaacc gcgcgaaaaa gtggtgacct ttcgccgccc ggatggctat
ctgaccaaac aggaaaaagg ctggaccagc gcgaccgaac ataccggcag cgcggatcag attattaaag atcgctatat
tctggcgatt gaagatccgt ttgaaattag ccataacgtg ggccgcaccg tgagcagcag cggcctgtat cgcattcgcg
gcgaatttat ggcggcgagc cgcctgctga acagccgcag ctatccgatt ccgtatgata gcctgtttga agaagcg As discussed above, the inhibitor coupled to the nucleotide analog will cause the transferase, e.g., TdT, to not release from the polynucleotide or prevent other analogs from being incorporated into the growing chain. A charged moiety results in better inhibition, however, research suggests that the specific chemical nature of the inhibitor is not particularly important. For example, both phosphates and acidic peptides can be used to inhibit enzymatic activity. See, e.g., Bowers et al., *Nature Methods*, vol. 6, (2009) p. 593-95, and U.S. Pat. No. 8,071,755, both of which are incorporated herein by reference in their entireties. In some embodiments, the inhibitor will include single amino acids or dipeptides, like -(Asp)$_2$, however the size and charge on the moiety can be adjusted, as needed, based upon experimentally determined rates of first nucleotide incorporation and second nucleotide incorporation. That is, other embodiments may use more or different charged amino acids or other biocompatible charged molecule.

Other methods of nucleotide synthesis may be used to build de novo oligonucleotides in a template independent fashion using nucleotidyl transferases or modified nucleotidyl transferases. In one embodiment, the polymerase/transferase enzymes can be modified so that they cease nucleotide addition when they encounter a modification to the phosphate of a 3'-unmodified dNTP analog. This scheme would require a deblocking reagent/reaction that modifies the phosphate end of the nucleotide analog, which frees up the nascent strand for subsequent nucleotide incorporation. Preferred embodiments of this approach would use nucleotide analogs modified only at the phosphates (alpha, beta or gamma) although modifications of the purine/pyrimidine base of the nucleotide are allowed.

Figure 19:
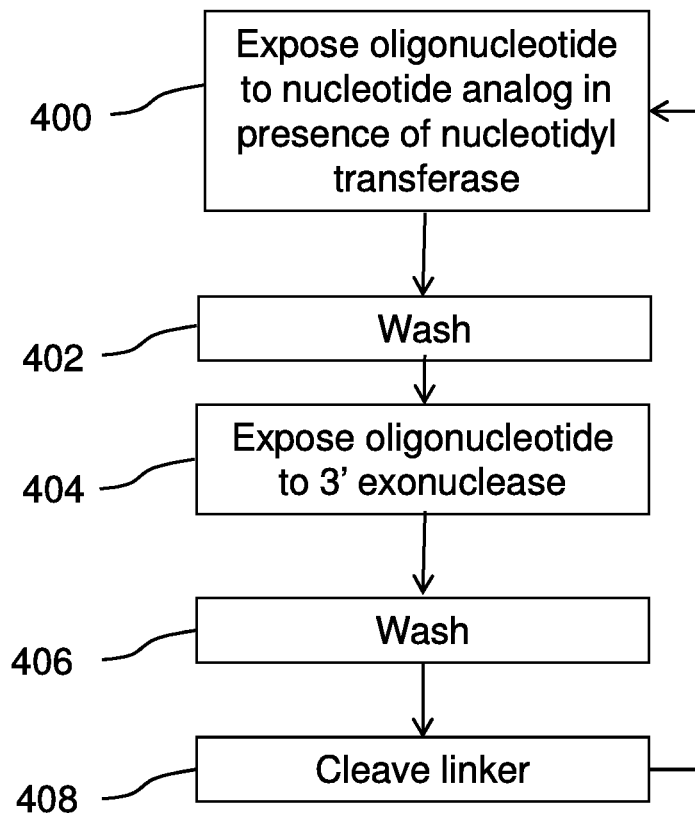
FIG. 19 shows a flow-chart describing the use of a 3' exonuclease to digest oligonucleotides that are not properly terminated between oligonucleotide synthesis cycles.

In some embodiments, it may be advantageous to use a 3' exonuclease to remove oligonucleotides that have not been properly terminated with an inhibitor prior to subsequent nucleotide analog addition. In particular, the inhibitor of the nucleotide analog can be chosen to inhibit the activity of nucleotidyl transferase and 3' exonucleases, such that only properly terminated oligonucleotides would be built up. Using this quality control technique, the purity of the resulting oligonucleotide sequences would be improved. In some embodiments, use of such quality control measures can negate the need for post-synthesis purification. This technique is represented schematically in FIG. 19, where a 3' exonuclease is introduced after a wash step to remove excess nucleotide analogs and prior to linker cleavage. Such a cleaning step, as shown in FIG. 19, will reduce the number of oligonucleotides that are of an undesired length and/or sequence.

Another embodiment for using non-template dependent polymerase/transferase enzymes would be to using protein engineering or protein evolution to modify the enzyme to remain tightly bound and inactive to the nascent strand after each single nucleotide incorporation, thus preventing any subsequent incorporation until such time as the polymerase/transferase is released from the strand by use of a releasing reagent/condition. Such modifications would be selected to allow the use of natural unmodified dNTPs instead of reversible terminator dNTPs. Releasing reagents could be high salt buffers, denaturants, etc. Releasing conditions could be high temperature, agitation, etc. For instance, mutations to the Loop1 and SD1 regions of TdT have been shown to dramatically alter the activity from a template-independent activity to more of a template dependent activity. Specific mutations of interest include but are not limited to Δ$_3$384/391/392, del loop1 (386→398), L398A, D339A, F401A, and Q402K403C404→E402R403S404. Other means of accomplishing the goal of a post-incorporation tight binding (i.e., single turnover) TdT enzyme could include mutations to the residues responsible for binding the three phosphates of the initiator strand including but not limited to K261, R432, and R454.

Another embodiment for using non-template dependent polymerase/transferase enzymes is to use protein engineering or protein evolution to modify the enzyme to accept 3-blocked reversible terminators with high efficiency. Naturally occurring polymerase/transferase enzymes will not incorporate 3'-blocked reversible terminators due to steric constraints in the active site of the enzyme. Modifying either single or several amino acids in the active site of the enzyme can allow the highly-efficient incorporation of 3'-blocked reversible terminators into a support bound initiator in a process completely analogous to that described above. After incorporation, the 3'-reversible terminator is removed with a deblocking reagent/condition thus generating a completely natural (scarless) single strand molecule ready for subsequent controlled extension reactions. The enzyme contains amino acids close to the 3'-OH of the incoming dNTP which explains the propensity of TdT for incorporating ribonucleotide triphosphates as readily as deoxyribonucleotide triphosphates; amino acids including but not limited to those between 31 and 32 especially R334, Loop1, and those between α13 and α14, especially R454, are likely β1 targets for mutagenesis to accommodate the bulk of 3'-reversible terminator groups and allow their efficient incorporation. In certain embodiments additional amino acid changes may be required to compensate for alterations made in order to accommodate a 3'-reversible terminator. Another embodiment for using template-dependent polymerases is to use the either 3'blocked or 3'unblocked dNTP analogs with a plurality of primer-template pairs attached to a solid support where the template is a nucleic acid analog that supports polymerase mediated primer extension of any of the four bases as specified by the user.

In some embodiments, an engineered TdT is used to achieve stepwise synthesis with 3'-O-blocked nucleotide analogs. It is possible to model the active site of the TdT protein using AutoDock (Molecular Graphics Laboratory, Scripps Research Institute, La Jolla, CA). Based upon this calculation, it is predicted that modified TdTs, having changes at Arg336 and Arg454 may have enzymatic activity against 3'-O-blocked nucleotide analogs. It is thought that Gly452 and Ser453 exist in a cis-peptide bond conformation (see Delarue et al., EMBO J., 2002; 21(3):427-39, incorporated herein by reference in its entirety) and that the guanidinium group of Arg336 assists in the stabilization of this conformation. The stability provided by Arg336 may help explain why substitutions at this position have a negative impact on the reactivity of modified TdT proteins. In some instances, the instability created by modifying position 336 may be overcome by using proline to stabilize cis-peptide bond conformation. However, if Arg336 is substituted, e.g., with alanine or glycine, the entire TGSR motif (positions 451, 452, 435, 454) may also have to be modified to compensate for this change. For example, the TGSR motif may be modified to TPSR or TGPR. In another embodiment, substitutions at Arg454 to accommodate the steric bulk of a 3'-O-blocking group may require additional modifications to the α14 region to compensate for substitutions of glycine or alanine at Arg454. In other embodiments, substitutions for other amino acids in the α11 region may be required to compensate for substitution to Arg336 either instead of, or in addition to, modification of the GSR motif.

While modification to Arg336 and Arg454 may change the binding interactions of 3'-O-modified dNTPs, it may also be necessary to explore substitutions that would result in improved steric interactions of 3'-O-modified dNTPs with TdT. Such steric modifications can also be explored computationally. Residues Gly332, Gly333, Gly452, Thr451 and Ser453 are also potential targets for substitution to allow the extra steric bulk of a 3'-blocking group like 3'-O-azidomethyl or 3'-O-allyl. Residues that are within 1.2 nm of the 3'-OH such as Glu457, Ala510, Asp509, Arg508, Lys199, Ser196 Met192, or Leu161 may also potentially interfere with the substrate utilization of a 3'-O-blocked dNTP and are thus targets for substitution in addition to or in combination with Arg336 and Arg454. In addition to amino acid substitutions at positions 508, 509 and 510, it may be necessary to delete amino acids in order to remove interference with a 3'-O-blocking group. Since those amino acids are located near the C-terminus of the protein, and exist in a relatively unstructured region, they may be deleted singly or altogether, either instead of or in combination with the modifications described above.

Another embodiment for using non-template dependent polymerase/transferase enzymes can use protein engineering or protein evolution to modify the enzyme to optimize the use of each of the four different nucleotides or even different modified nucleotide analogs in an analog specific manner. Nucleotide specific or nucleotide analog specific enzyme variants could be engineered to possess desirable biochemical attributes like reduced $K_m$ or enhanced addition rate which would further reduce the cost of the synthesis of desired polynucleotides.

Solid State Synthesis

Figure 13:
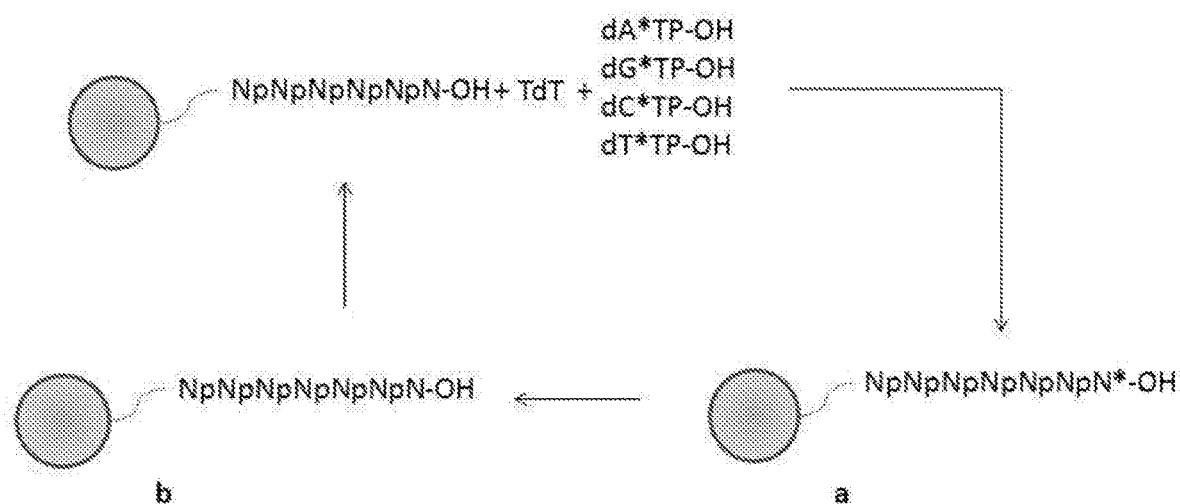
FIG. 13 shows an exemplary terminal deoxynucleotidyl transferase (TdT) mediated polynucleotide synthetic cycle, including: (a) incorporation of a nucleotide triphosphate analog comprising cleavable terminator, dN*TP-OH, and (b) removal of the terminating blocking group (indicated by *), thus enabling the next dN*TP-OH to be incorporated, wherein N=A, G, C, or T.
Figure 14:
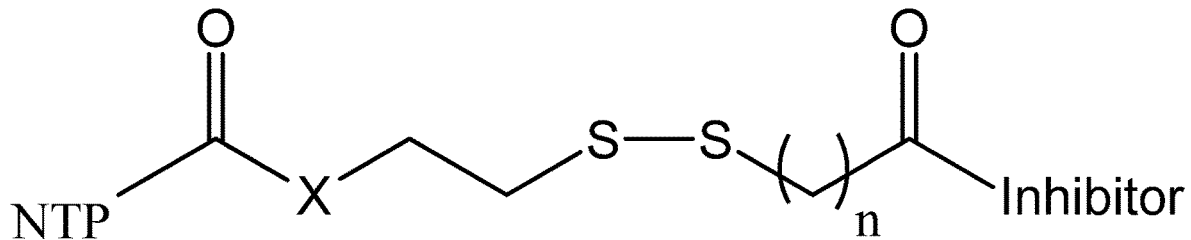
FIG. 14 shows an exemplary nucleotide analog with a cleavable linker comprising a variable number of methylene bridges.

The methods of the invention can be practiced under a variety of reaction conditions, however the orderly construction and recovery of desired polynucleotides will, in most cases, require a solid support on which the polynucleotides can be extended. When used in conjunction with the NTP, linker, and inhibitor analogs discussed above, it is possible to construct specific polynucleotide sequences of DNA, as well as RNA, by using, for example, TdT or poly(A) polymerase in an aqueous environment. As shown in FIG. 13, the TdT can be used to effect the stepwise construction of custom polynucleotides by extending the polynucleotide sequence in a stepwise fashion. As discussed previously, the inhibitor group of each NTP analog causes the enzyme to stop with the addition of a nucleotide. After each nucleotide extension step, the reactants are washed away from the solid support prior to the removal of the inhibitor by cleaving the linker, and then new reactants are added, allowing the cycle to start anew.

In certain embodiments, an additional quality control step may be incorporated in which the oligonucleotide or polynucleotide is exposed to 3' exonuclease after the nucleotidyl transferase-mediated nucleotide analog extension step and before inhibitor cleavage. A 3' exonuclease degrades oligonucleotide or polynucleotide strands with an unblocked 3' OH. An uncleaved inhibitor (e.g., a steric inhibitor) may physically block the 3' exonuclease from degrading a strand to which an uncleaved nucleotide analog has been successfully incorporated. Such a quality control step degrades only the oligonucleotides or polynucleotides that have unsuccessfully incorporated the desired nucleotide analog in the prior addition step, thereby eliminating any errors in the finished synthesized sequence. After 3' exonuclease exposure, the enzyme may be washed away before carrying on with the inhibitor cleavage step.

The 3' exonuclease acts by shortening or completely degrading strands that have not successfully added the desired nucleotide analog. Strands that fail to be enzymatically extended at a given cycle will not have a terminal macromolecule-dNMP conjugate prior to the linker cleavage step. If a 3'-exonuclease is introduced at this stage, the full length strand could be protected from degradation while "failure" strands will be shorted in length or potentially degraded completely to mononucleotide phosphates. The yield of long (>500 bases) synthetic DNA is dependent on highly efficient reactions occurring at each and every cycle; both the enzymatic extension and the deblocking/self-elimination steps must occur at near quantitative yields. The introduction of a 3'-exonuclease after the enzymatic extension step but before the macromolecule terminator cleavage step has a positive impact on the nascent strand purity if the extension efficiency is low (i.e., there are strands that are not extended and therefore possess a natural unmodified terminal nucleotide).

Conversely, a 3'-exonuclease step would have no impact on the quality of the synthesis if the deblocking/elimination step is less than quantitative because those strands would still be protected by the macromolecule terminator and fail to extend during the next extension step. Thus the actual improvement of the quality of the synthesis with the addition of a 3'-exonuclease step can only be experimentally determined and then an assessment made if it is worth the additional cost and cycle time.

Enzymes having 3'-5' exonuclease activity include 3'-exonucleases as discussed above as well as polymerases having 3'-exonuclease. Exemplary enzymes having 3'-5' exonuclease activity include ExoI, Thermolabile ExoI, and ExoT, Exo I, Exo T, Thermolabile Exo I, Exo II, Exo III, Exo IV, Exo V, ExoVII, Exo IX, Exo IX, TREX1, TREX2 RNase T, Pol d, Pol e, Pol g, POL3, POL2, MIP1, WRN, p53, MRE11, hRAD1, RAD1, hRAD9, and Rad9.

At the conclusion of n cycles of extension-remove-deblocking-wash, the finished full-length, single-strand polynucleotide is complete and is cleaved from the solid support and recovered for subsequent use in applications such as DNA sequencing or PCR. Alternatively, the finished, full-length, single-strand polynucleotide can remain attached to the solid support for subsequent use in applications such as hybridization analysis, protein or DNA affinity capture. In other embodiments, partially double-stranded DNA can be used as an initiator, resulting in the synthesis of double-stranded polynucleotides.

In certain embodiments, a nucleotide analog addition cycles may include exposing an oligonucleotide attached to a solid support to a nucleotide analog in the presence of a nucleotidyl transferase enzyme and in the absence of a nucleic acid template under conditions sufficient for incorporation of said analog into said oligonucleotide. The nucleotide analog can include a 3'-O-blocking group that prevents the nucleotidyl transferase from catalyzing addition of either a natural nucleotide or a nucleotide analog into said oligonucleotide until said blocking group is removed. After each nucleotide analog incorporation, the oligonucleotide may be exposed to a second nucleotide analog that does not confer resistance to exonuclease activity. The oligonucleotide may be then exposed to an enzyme having 3'-5' exonuclease activity prior to removal of the 3'-blocking group. Strands where the desired 3'-O blocked nucleotide analog was not incorporated will instead have the second nucleotide analog incorporated or none at all (leaving an unmodified 3'-OH susceptible to exonuclease activity). Accordingly, treatment with an exonuclease prior to removal of 3'-O blocking groups will result in the digestion of error strands in which the desired nucleotide analog was not incorporated. The second nucleotide analog is selected from the group consisting of a 2',3'-dideoxy nucleotide and a 2',3'-dehydro nucleotide.

The exonuclease treatment may occur after each nucleotide analog incorporation cycle or may be reserved and only performed after two or more nucleotide analog incorporations or after incorporation of the final nucleotide analog to complete the desired oligonucleotide sequence (but before removal of the final blocking group). In the case of sequence-terminating second nucleotide analogs, error strands in which a desired 3'-O blocked nucleotide analog was not successfully incorporated will be blocked from further extension by the strand-terminating second nucleotide and, therefore, will have no further 3'-O blocked nucleotide analogs incorporated. Accordingly, even if the exonuclease treatment is reserved for the final incorporation step, any error strands occurring along the way will remain susceptible to exonuclease activity. 11. The method of claim 9, wherein an addition cycle comprises steps a), b), and c), followed by removal of the 3'-blocking group, the method further comprising repeating the addition cycle 2 or more times. In certain embodiments, the final incorporation step may include adding a nucleotide analog with a 3'-O blocking group and a biotin modification.

Figure 22:
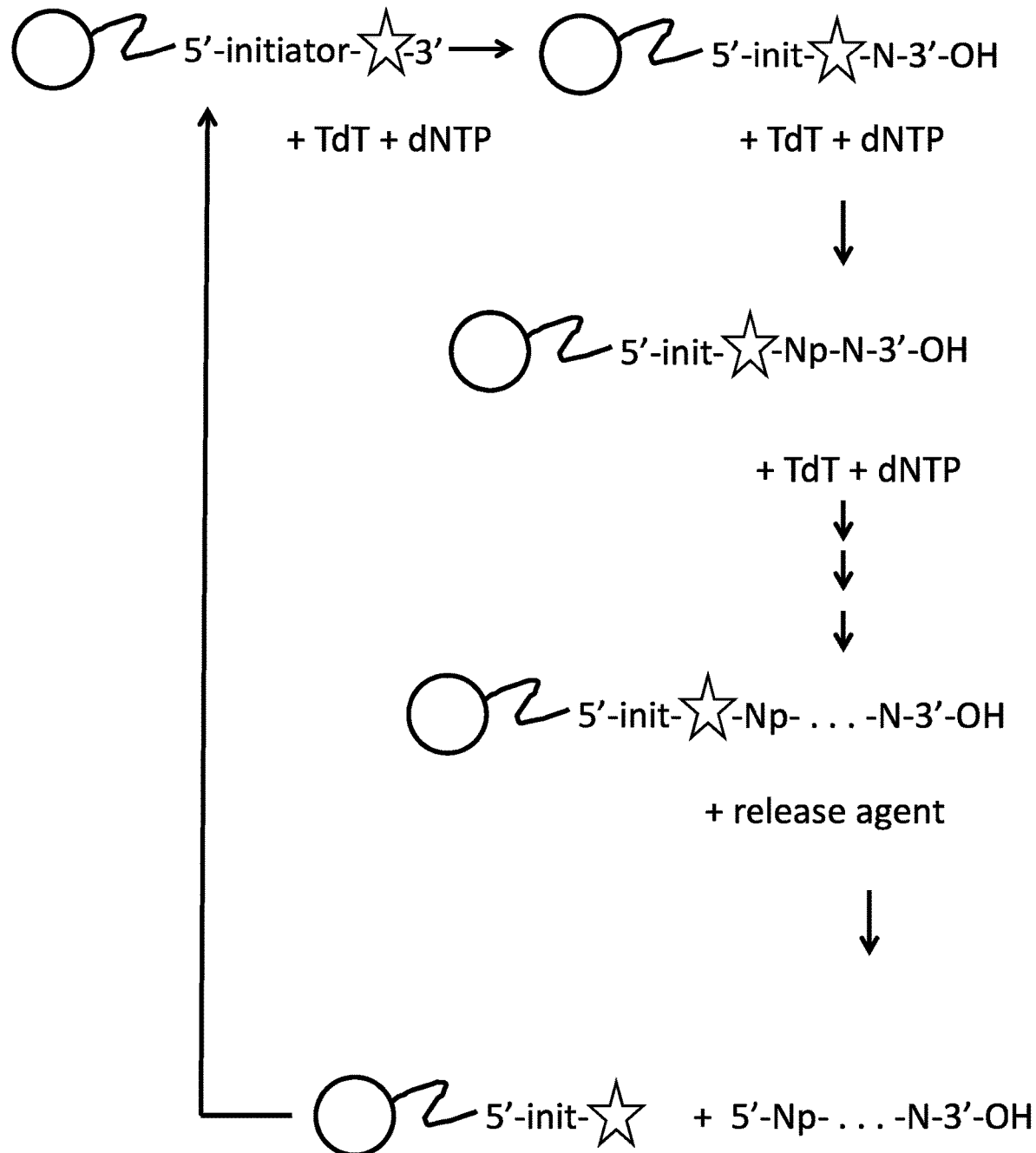
FIG. 22 illustrates the incorporation of a reusable 3' moiety into a nucleic acid coupled to a solid support, growth of a nucleic acid using a modified TdT, and release of the de novo oligonucleotide.

In some embodiments, a nucleic acid initiator will include a 3' moiety that will release the synthesized oligonucleotide when in the presence of a releasing agent. This feature is illustrated, generally, in FIG. 22, where a nucleic acid initiator (5'-initiator-) is shown coupled to a solid state support (open circle) and a releasable 3' moiety (open star). In some embodiments the initiator is a single-stranded oligonucleotide, such as a dimer, trimer, tetramer, pentamer, hexamer, septamer, or octomer. Because the 3' moiety attached to the initiator is a substrate for the enzyme, e.g., a TdT, e.g., a modified TdT, the enzyme can add additional nucleotides or nucleotide analogs in a stepwise fashion. With each addition, the length of the synthesized oligonucleotide increases. Once the oligonucleotide synthesis is complete, a releasing agent can be introduced to cause the 3' moiety to decouple from the nucleic acid initiator. In some embodiments, the 3' moiety is a ribonucleotide, such as an A, C, G, or U ribonucleotide. In other embodiments, the 3' moiety is an abasic deoxyribose. In other embodiments, the 3' moiety is an abasic ribose. In other embodiments, the 3' moiety is a non-nucleoside 5'-monophosphate. The releasing agent may include a basic solution or a metal ion. For example, the releasing agent can be a concentrated $NH_4OH$ solution, having a pH greater than 8, i.e., greater than pH 8.5, i.e., greater than pH 9.0, i.e., greater than pH 9.5. In some embodiments, the releasing agent will be an enzyme, such as a type II restriction nuclease. In some embodiments, the enzyme will uniquely interact with the nucleic acid sequence of the initiator, and lyse the synthesized oligonucleotide from the initiator, leaving behind the initiator.

In an embodiment, the initiator is a nucleic acid hexamer and the 3' moiety is a ribonucleotide, such as adenosine. Once the oligonucleotide synthesis is complete, e.g., using nucleotides comprising a cleavable terminator linked at the N-4 position, or nucleotides having a 3'-O-blocked position, the oligonucleotide can be released by exposing the bound oligonucleotide to an ammonium hydroxide solution of a pH around 8. The basic solution containing the synthesized oligonucleotides can then be separated from the solid substrate comprising the hexamer initiator. The solid substrate is then washed and/or neutralized to prepare the initiator and 3' moiety for fabrication of a new oligonucleotide. In some embodiments, the terminal ribonucleotide is regenerated prior to oligonucleotide synthesis with the use of a phosphatase or the 3' phosphatase activity of T4 polynucleotide kinase.

In some embodiments, the solid support and nucleic acid initiator including the 3' moiety will be reusable, thereby allowing the initiator coupled to the solid support to be used again and again for the rapid synthesis of oligonucleotides. Solid supports suitable for use with the methods of the invention may include glass and silica supports, including beads, slides, pegs, or wells. In some embodiments, the support may be tethered to another structure, such as a polymer well plate or pipette tip. In some embodiments, the solid support may have additional magnetic properties, thus allowing the support to be manipulated or removed from a location using magnets. In other embodiments, the solid support may be a silica coated polymer, thereby allowing the formation of a variety of structural shapes that lend themselves to automated processing.

The selection of substrate material and covalent linkage chemistry between initiator and substrate is limited only by the ability of the construct to withstand the synthesis conditions without loss of initiator. Preferred embodiments utilize substrates and linkers of greater chemical stability than the initiator so that the overall construct stability is that of the attached oligonucleotide and not dependent on the substrate. In some embodiments, initiators may be synthesized in a 5' to 3'-direction from a material presenting surface hydroxyl groups, though in preferred embodiments the initiator is instead grafted to the substrate so that density and initiator quality can be precisely controlled.

The covalent linkage between the initiator and the substrate may be any bond which does not compromise the stability of the construct. Preferred embodiments may utilize couplings between oligonucleotides containing either 5'-amine, 5'-hydroxyl, 5'-phosphate, 5'-sulfhydryl, or 5'-benzaldehyde groups and surfaces or resins containing formyl, chloromethyl, epoxide, amine, thiol, alkene, or terminal C—F bonds on the substrate.

In some embodiments, the initiator may contain elements for sequence-specific cleavage strategies, such as those utilizing restriction enzymes, uracil specific excision reagent (USER), or any variety of sequence-specific nuclease. In other embodiments, these elements may instead be enzymatically synthesized or added to the initiator after it has been coupled to a resin. Such a scenario may be preferred when, for example, the initiator is comprised of entirely thymidine in order to minimize potential side reactions with surface functional groups during the coupling process.

Figure 23:
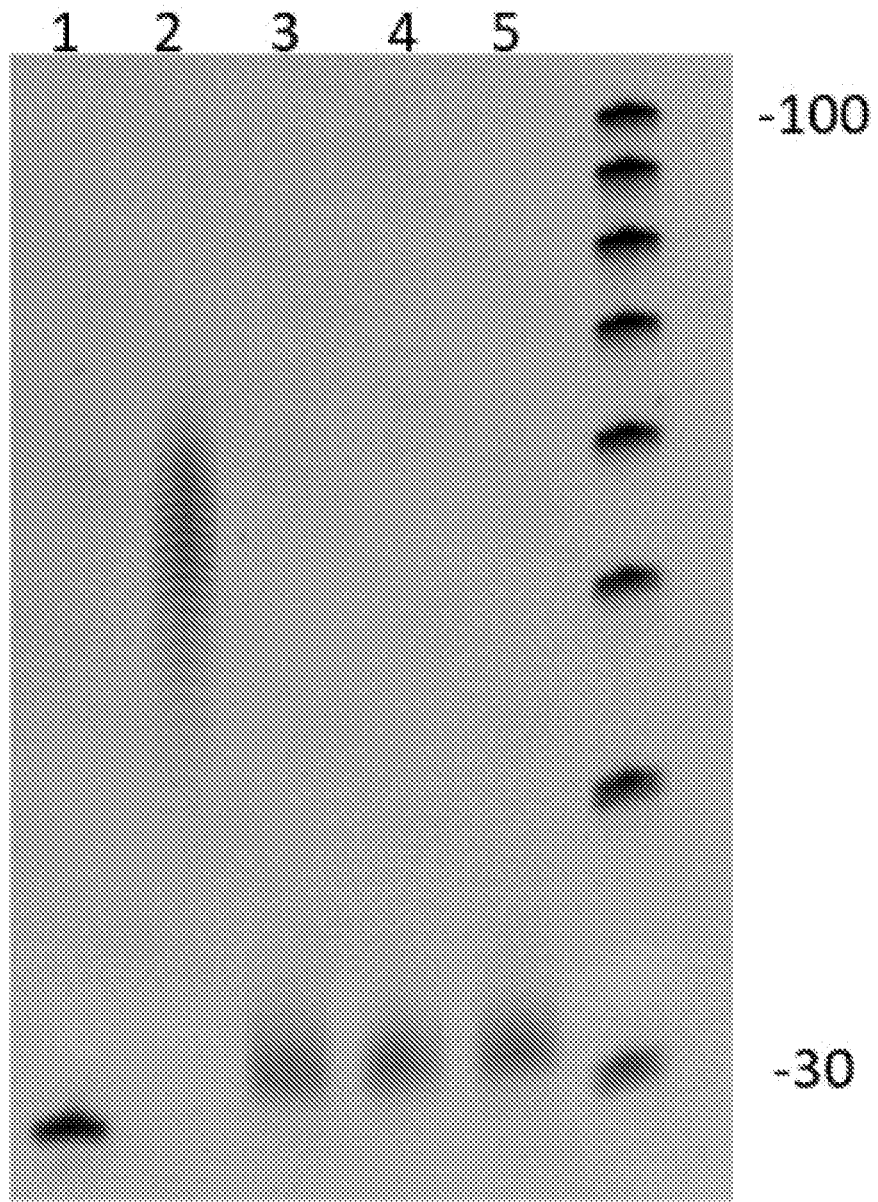
FIG. 23 shows the results of enzymatic installation of a 3'-poly-U tract with TdT, followed by USER digestion of the tract.

FIG. 23 shows a solution-phase example where a short poly-uracil (U) tract is added to the 3'-end of an initiator using TdT. The resultant initiator may then be used for further extension reactions as described to generate the desired sequence. Upon completion of the synthesis, the newly generated sequence may be cleaved at the internal poly-U tract to separate the new sequence from the original initiator. The 30 nucleotide initiator used is of the sequence 5'-TTATTATTATTATTAAAAAAGGCCAAAAAA (SEQ ID NO: 7). The gel shown in FIG. 23 includes the initiator run in lane 1 while the initiator after one or more additions of dUTP (i.e., the poly-uracil tract) was run in lane 2. The generated sequence was then subjected to USER digestion for 10, 30, and 60 minutes and run in lanes 3, 4, and 5 respectively.

Figure 24:
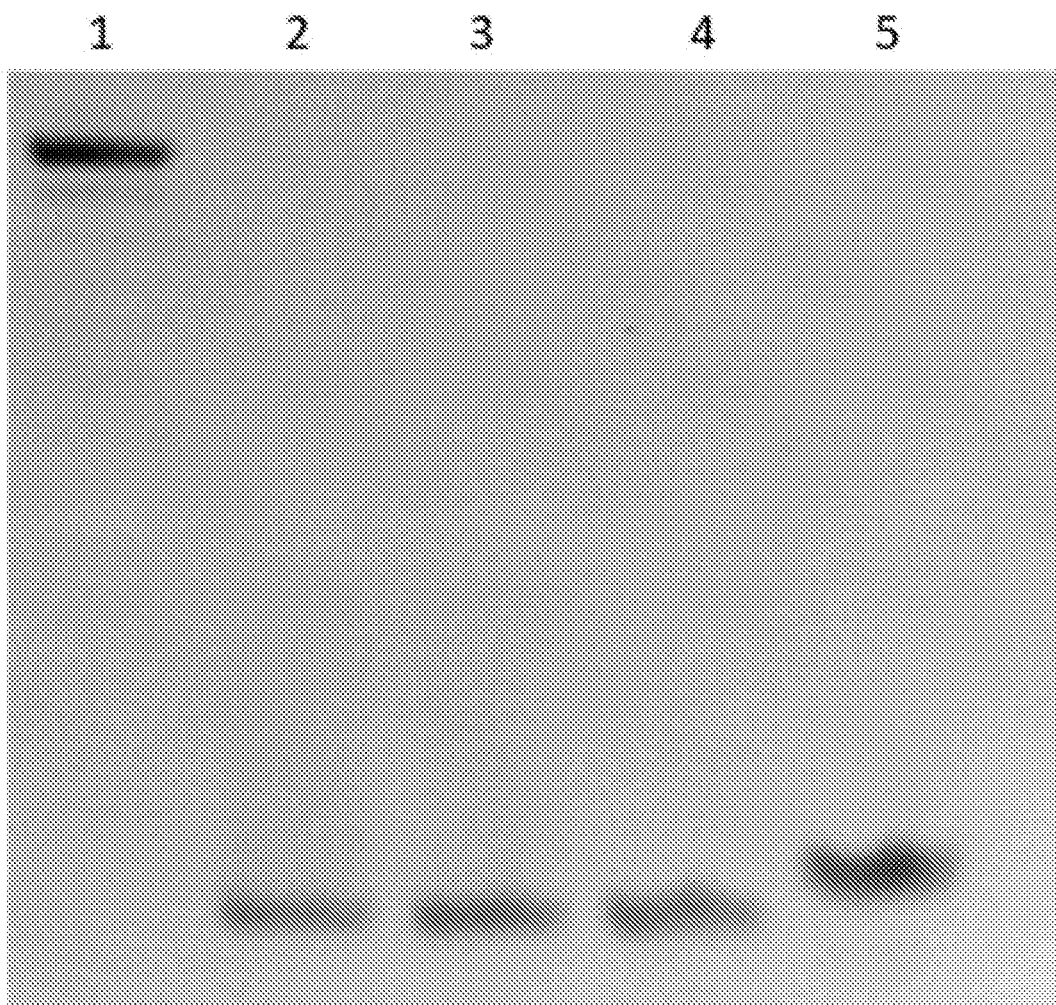
FIG. 24 shows the results of USER digestion of an internal poly-U tract to produce a 5'-monodisperse cleavage product.

FIG. 24 shows that the cleavage of a sequence containing an internal poly-U tract produces a single product of homogenous length bearing a 5'-phosphate. The cleavage process leaves a 3'-phosphate on the resin-bound initiator, which may be removed with treatment with T4 polynucleotide kinase, alkaline phosphatase or other dephosphorylation process (See FIG. 25). The internal poly-U tract sequence cleaved in the example depicted in FIG. 24 was of sequence 5'-TTAATTAATUUUUGTGAGCTTAATGTCCTTATGT (SEQ ID NO: 8) which, after USER digestion, resulted in a product of sequence 5'-phos-GTGAGCTTAATGTCCT-TATGT (SEQ ID NO: 9). The resulting product was run after 0, 10, 30, and 60 minutes of USER digestion in lanes, 1, 2, 3, and 4 as shown in FIG. 24, indicating the successful cleavage and homogenous length of the products. In lane 5, a control oligonucleotide of sequence GTGAGCT-TAATGTCCTTATGT (SEQ ID NO: 10) was run.

Figure 25:
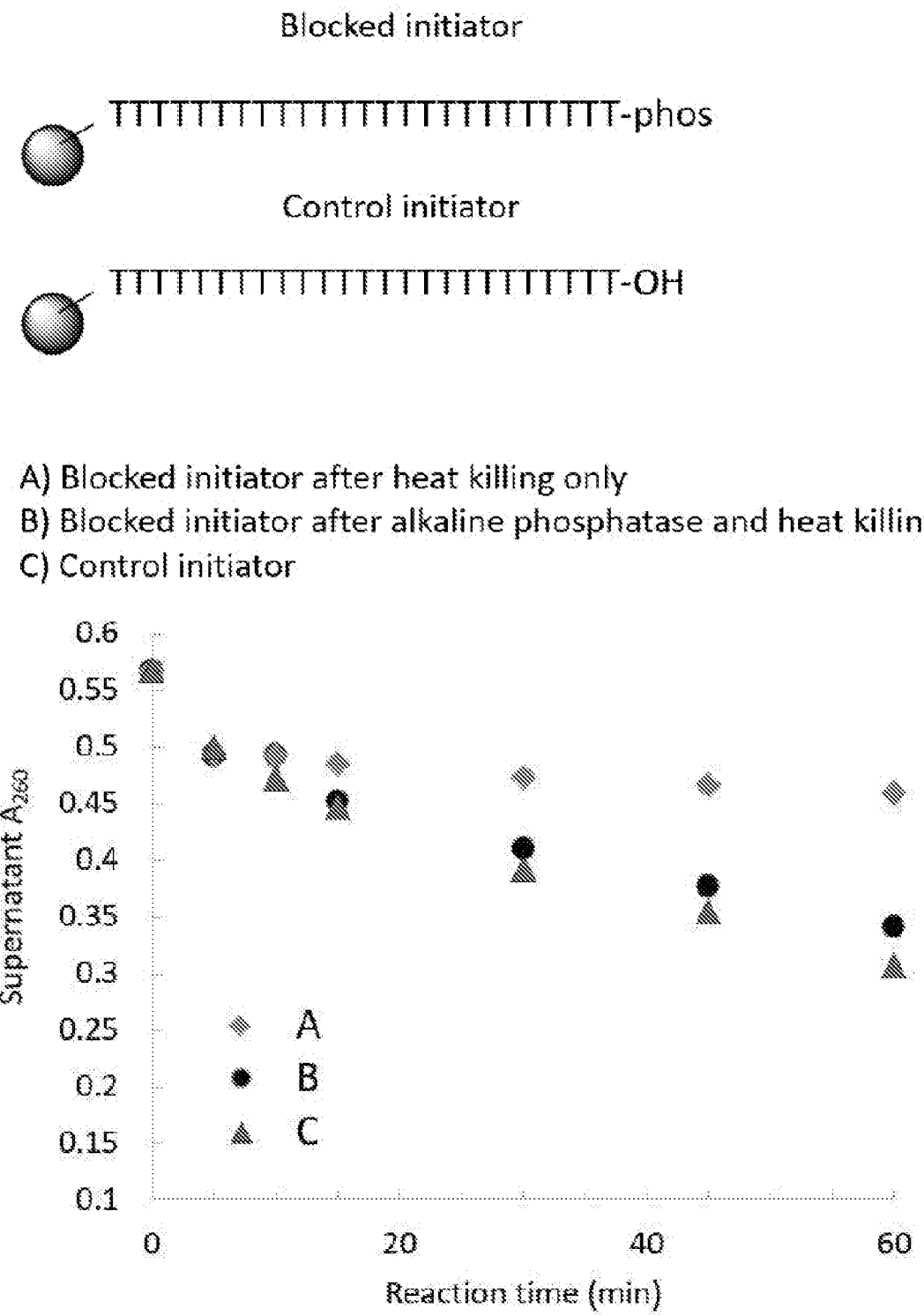
FIG. 25 illustrates solid-phase dephosphorylation and TdT extension results.

FIG. 25 shows an exemplary solid-phase dephosphorylation and TdT extension process. The chart depicts the absorbance of the TdT reaction mixture in a solid-phase extension. As dNTPs are added to the resin-bound initiator, they are depleted from solution, reducing absorbance of the supernatant. Trace A shows the negligible rate of dNTP incorporation onto a resin where the 3'-end of the initiator is blocked with a terminal phosphate. Trace B shows the rate of incorporation after such an initiator is treated with shrimp alkaline phosphatase for 15-minutes. Trace C shows the rate of dNTP incorporation under the same conditions using an unblocked initiator.

Figure 26:
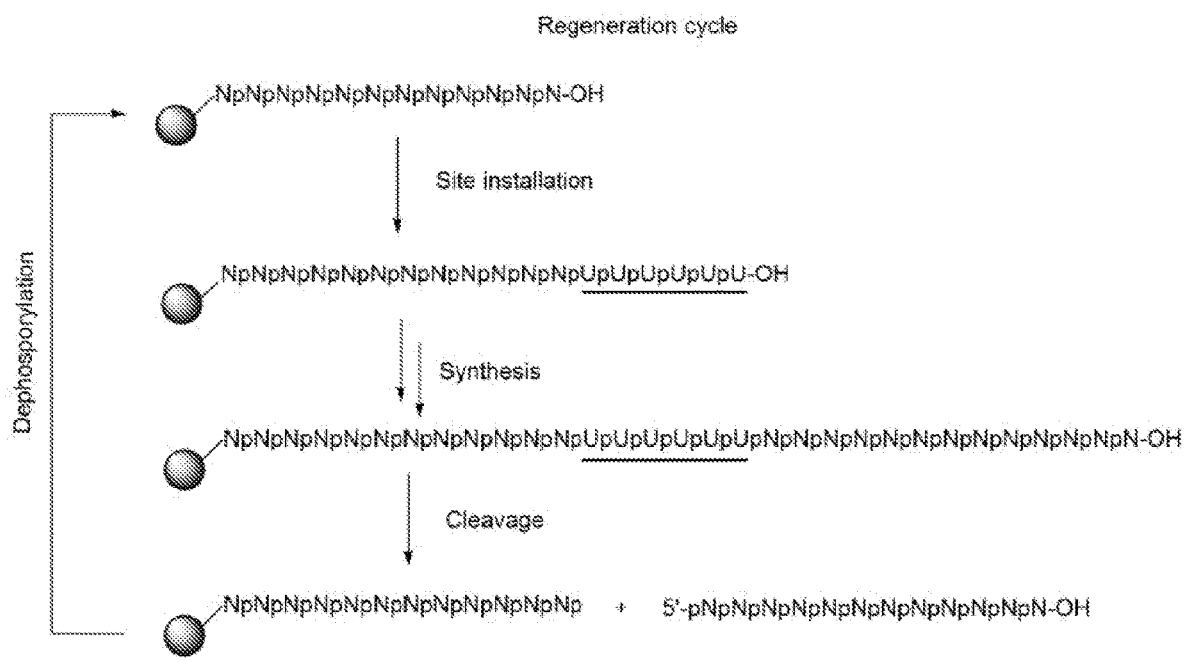
FIG. 26 shows an exemplary resin regeneration cycle.

After cleavage of the synthesized sequence, the resin may then be used in another cycle of cleavage site installation, synthesis, product removal, and regeneration. FIG. 26 provides an overview of an exemplary regeneration cycle.

In other embodiments, the cleavage site installation may be used to homogenize the enzymatic accessibility of the initiator oligonucleotides. Each enzyme used during the enzymatic synthesis cycle has its own steric footprint with potentially distinct optimal loadings and spacing from the surface. This can produce unexpected behavior in regard to the kinetics of stepwise addition and yield from the enzymatic cleavage process. In some embodiments, repeated cycles of cleavage site installation, cleavage, and regeneration may be conducted prior to the oligonucleotide synthesis so that the cleavage enzyme and the template-independent polymerase are accessing the same population of surface oligonucleotides.

Some embodiments may install multiple different cleavage sites throughout a strand during synthesis. Upon digestion, a complex library of the strands located between the cleavage sites may be released from the resin. Such sequences can then be further amplified and used for enzymatic assembly processes by a skilled artisan. This approach may be uniquely suited to parallel synthesis schemes in order to produce greater varieties of sequence fragments with relatively few distinct locations on a surface, or to avoid the synthesis of contiguous strands which risk secondary structure formation during synthesis.

In other embodiments, cleavage site installation may be used immediately after each cycle of enzymatic extension to assist in the removal of unreacted initiator sequences, analogous to the acetylation used in phosphoramidite-based oligonucleotide synthesis. Strands which are unextended during the addition cycle act as substrates for a poly-U tract, while extended initiators bearing a chain terminator do not. At the end of the synthesis cycle, a single USER digestion is conducted so that the oligonucleotides are released from the support, and sequences containing failed additions are simultaneously digested to a shorter length than the full-sized product. Failure sequences are also alike in that they are now phosphorylated at their 3'-ends, rendering them unreactive to further enzymatic extension. The full-length sequences may then undergo extension to append any element which will enable selective capture, isolation, or enrichment. Such elements may either be additional homopolymer tracts, such as further poly-U tracts, which can be isolated by hybridization-based approaches and subsequently digested, or biotinylated elements for non-covalent capture. This approach compensates for the lack of suitable chromatographic techniques suitable for long (150 nt+ oligonucleotides), low sample quantities, or complex mixtures of sequences of varied lengths.

Figure 27:
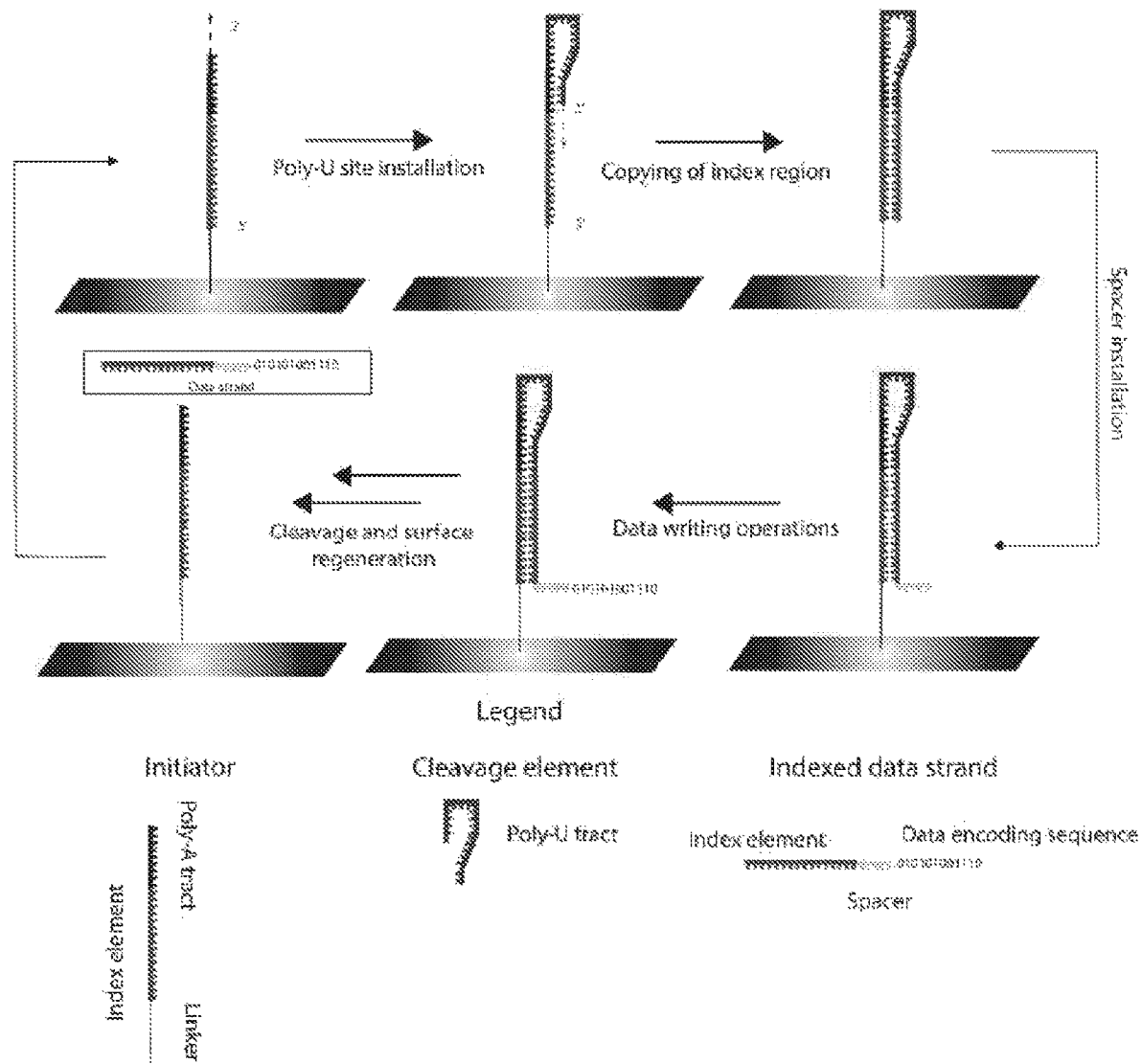
FIG. 27 shows an exemplary index strand regeneration process.

Further embodiments may employ cleavage site installations to assist in the recycling of highly-indexed DNA-based data recording media. An example is shown in FIG. 27. In such cases, 5'-surface-immobilized sequences are terminated with a short poly-A tract. Extension to produce a terminal 3'-poly-U site of sufficient length will allow a hairpin to fold under appropriate conditions, so that the elements of the initiator preceding the poly-A stretch can be replicated using a template-dependent polymerase. The sequence can then be extended with a new homopolymer tract to leave a free 3'-terminus which can be used in subsequent data-writing operations. Upon completion of the write steps, the hairpin linker can then be digested with the USER enzyme to release the data strand, while leaving the template initiator to be regenerated with a 3'-dephosphorylation step, poly-U addition, and recopying of the template strand. The use of homopolymer tracts in DNA-based data recording is described in co-owned U.S. patent application Ser. No. 15/994,335, incorporated herein by reference.

Synthesizers

To capitalize on the efficiency of the disclosed methods, an aqueous phase DNA synthesizer can be constructed to produce desired polynucleotides in substantial quantities. In one embodiment, a synthesizer will include four wells of the described NTP analog reagents, i.e., dCTP, dATP, dGTP, and dTTP, as well as TdT at concentrations sufficient to effect polynucleotide growth. A plurality of initiating sequences can be attached to a solid support that is designed to be repeatedly dipped into each of the four wells, e.g., using a laboratory robot. The robot could be additionally programmed to rinse the solid support in wash buffer between nucleotide additions, cleave the linking group by exposing the support to a deblocking agent, and wash the solid support a second time prior to moving the solid support to the well of the next desired nucleotide. With simple programming, it is possible to create useful amounts of desired nucleotide sequences in a matter of hours, and with substantial reductions hazardous waste. Ongoing synthesis under carefully controlled conditions will allow the synthesis of polynucleotides with lengths in the thousands of base pairs. Upon completion, the extension products are released from the solid support, whereupon they can be used as finished nucleotide sequences.

A highly parallel embodiment could consist of a series of initiator-solid supports on pegs in either 96 or 384 well formats that could be individually retracted or lowered so that the pegs can be indexed to contact the liquids in the wells in a controlled fashion. The synthesizer could thus consist of the randomly addressable peg device, four enzyme-dNTP analog reservoirs in the same format as the peg device (96 or 384 spacing), additional reagent reservoirs (washing, deblocking, etc.) in the same format as the peg device (96 or 384 spacing), and a transport mechanism (e.g., a laboratory robot) for moving the peg device from one reservoir to another in a user programmable controlled but random access fashion. Care must be taken to avoid contaminating each of the four enzyme-dNTP reservoirs since the contents are reused throughout the entire synthesis process to reduce the cost of each polynucleotide synthesis.

In alternative embodiments, the reagents (e.g., nucleotide analogs, enzymes, buffers) will be moved between solid supports, allowing the reagents to be recycled. For example a system of reservoirs and pumps can move four different nucleotide analog solutions, wash buffers, and/or reducing agent solutions between one or more reactors in which the oligonucleotides will be formed. The reactors and pumps can be conventional, or the devices may be constructed using microfluidics. Because of the non-anhydrous (aqueous) nature of the process, no special care needs to be taken in the design of the hardware used to eliminate exposure to water. The synthesis process can take place with only precautions to control evaporative loss. A highly parallel embodiment could consist of a monolithic series of initiator-solid supports on pegs in either 96 or 384 well format that can be interfaced to a series of wells in the same matching format. Each well would actually be a reaction chamber that is fed by four enzyme-dNTP analog reservoirs and additional reagent reservoirs (washing, deblocking, etc.) with appropriate valves. Provisions would be made in the fluidics logic to recover the enzyme-dNTP reactants in a pristine fashion after each extension reaction since they are reused throughout the entire synthesis process to reduce the cost of each polynucleotide synthesis. In other embodiments, a system of pipetting tips could be used to add and remove reagents.

Figure 17:
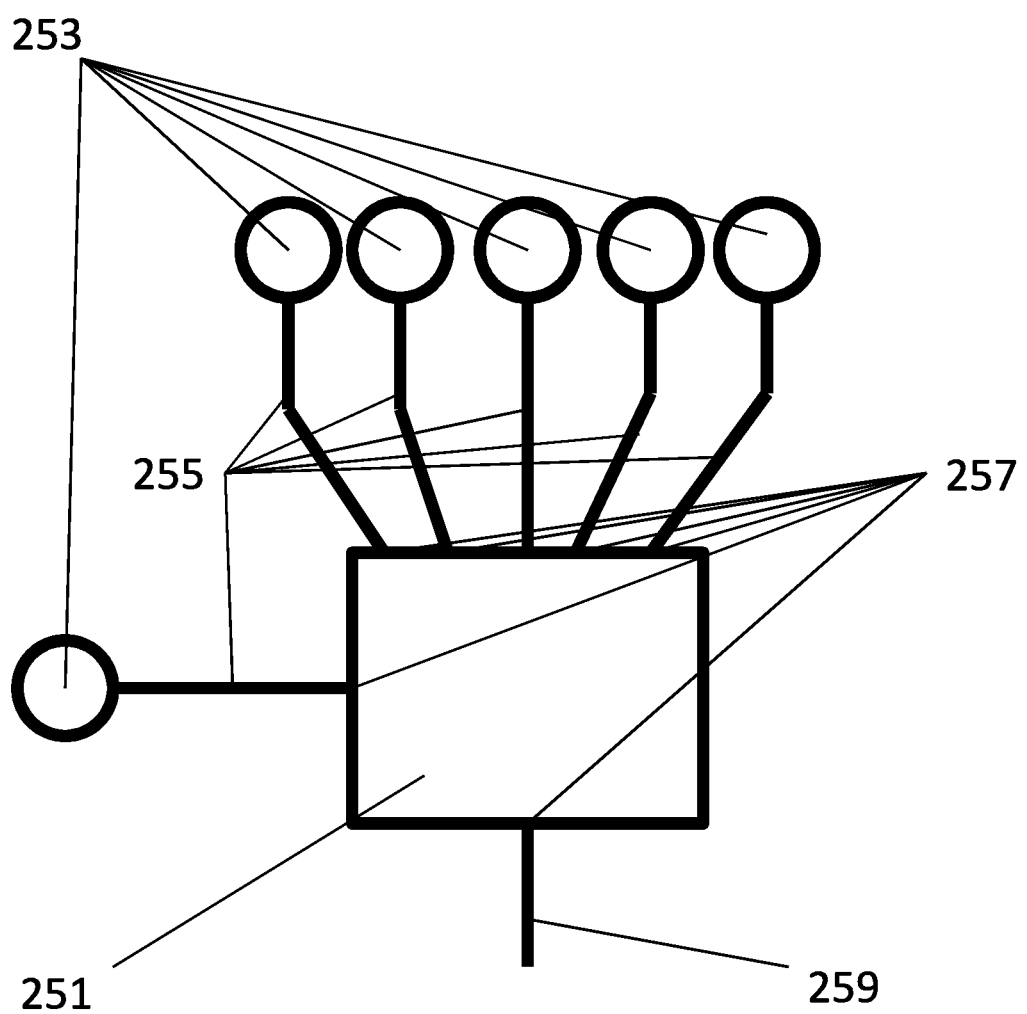
FIG. 17 shows an exemplary microfluidic polynucleotide synthesis device.

In certain aspects, polynucleotides may be synthesized using microfluidic devices and/or inkjet printing technology. An exemplary microfluidic polynucleotide synthesis device is shown in FIG. 17 for illustrative purposes and not to scale. Microfluidic channels 255, including regulators 257, couple reservoirs 253 to a reaction chamber 251 and an outlet channel 259, including a regulator 257 can evacuate waste from the reaction chamber 251. Microfluidic devices for polynucleotide synthesis may include, for example, channels 255, reservoirs 253, and/or regulators 257. Polynucleotide synthesis may occur in a microfluidic reaction chamber 251 which may include a number of anchored synthesized nucleotide initiators which may include beads or other substrates anchored or bound to an interior surface of the reaction chamber and capable of releasably bonding a NTP analog or polynucleotide initiator. The reaction chamber 251 may include at least one intake and one outlet channel 259 so that reagents may be added and removed to the reaction chamber 251. The microfluidic device may include a reservoir 253 for each respective NTP analog. Each of these NTP analog reservoirs 253 may also include an appropriate amount of TdT or any other enzyme which elongates DNA or RNA strands without template direction. Additional reservoirs 253 may contain reagents for linker/inhibitor cleavage and washing. These reservoirs 253 can be coupled to the reaction chamber 251 via separate channels 255 and reagent flow through each channel 255 into the reaction chamber 251 may be individually regulated through the use of gates, valves, pressure regulators, or other means. Flow out of the reaction chamber 251, through the outlet channel 259, may be similarly regulated.

In certain instances, reagents may be recycled, particularly the NTP analog-enzyme reagents. Reagents may be drawn back into their respective reservoirs 253 from the reaction chamber 251 via the same channels 255 through which they entered by inducing reverse flow using gates, valves, pressure regulators or other means. Alternatively, reagents may be returned from the reaction chamber 251 to their respective reservoirs 253 via independent return channels. The microfluidic device may include a controller capable of operating the gates, valves, pressure, or other regulators 257 described above.

An exemplary microfluidic polynucleotide synthesis reaction may include flowing a desired enzyme-NTP analog reagent into the reaction chamber 251; after a set amount of time, removing the enzyme-NTP analog reagent from the reaction chamber 251 via an outlet channel 259 or a return channel; flowing a wash reagent into the reaction chamber 251; removing the wash reagent from the reaction chamber 251 through an outlet channel 259; flowing a de-blocking or cleavage reagent into the reaction chamber 251; removing the de-blocking or cleavage reagent from the reaction chamber 251 via an outlet channel 259 or a return channel; flowing a wash reagent into the reaction chamber 251; removing the wash reagent from the reaction chamber 251 through an outlet channel 259; flowing the enzyme-NTP analog reagent including the next NTP in the desired sequence to be synthesized into the reaction chamber 251; and repeating until the desired polynucleotide has been synthesized. After the desired polynucleotide has been synthesized, it may be released from the reaction chamber anchor or substrate and collected via an outlet channel 259 or other means.

In certain aspects, reagents and compounds, including NTP analogs, TdT and/or other enzymes, and reagents for linker/inhibitor cleavage and/or washing may be deposited into a reaction chamber using inkjet printing technology or piezoelectric drop-on-demand (DOD) inkjet printing technology. Inkjet printing technology can be used to form droplets, which can be deposited, through the air, into a reaction chamber. Reagent droplets may have volumes in the picoliter to nanoliter scale. Droplets may be introduced using inkjet printing technology at a variety of frequencies including 1 Hz, 10, Hz, 100 Hz, 1 kHz, 2 kHz, and 2.5 kHz. Various reagents may be stored in separate reservoirs within the inkjet printing device and the inkjet printing device may deliver droplets of various reagents to various discrete locations including, for example, different reaction chambers or wells within a chip. In certain embodiments, inkjet and microfluidic technologies may be combined wherein certain reagents and compounds are delivered to the reaction chamber via inkjet printing technology while others are delivered via microfluidic channels or tubes. An inkjet printing device may be controlled by a computing device comprising at least a non-transitory, tangible memory coupled to a processor. The computing device may be operable to receive input from an input device including, for example, a touch screen, mouse, or keyboard and to control when and where the inkjet printing device deposits a droplet of reagent, the reagent it deposits, and/or the amount of reagent deposited.

In certain instances, a desired polynucleotide sequence may be entered into the computing device through an input device wherein the computing device is operable to perform the necessary reactions to produce the desired polynucleotide sequence by sequentially depositing the appropriate NTP analog, enzyme, cleavage reagent, and washing reagent, in the appropriate order as described above.

After synthesis, the released extension products can to be analyzed by high resolution PAGE to determine if the initiators have been extended by the anticipated number of bases compared to controls. A portion of the recovered synthetic DNA may also be sequenced to determine if the synthesized polynucleotides are of the anticipated sequence.

Because the synthesizers are relatively simple and do not require the toxic components needed for phosphoramidite synthesis, synthesizers of the invention will be widely accessible for research institutions, biotechnology companies, and hospitals. Additionally, the ability to reuse/recycle reagents will reduce the waste produced and help reduce the costs of consumables. The inventors anticipate that the methods and systems will be useful in a number of applications, such as DNA sequencing, PCR, and synthetic biology.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

---

The invention claimed is:

1. A method for synthesizing an oligonucleotide, the method comprising:
 exposing an oligonucleotide attached to a solid support to a nucleotide analog in the presence of a nucleotidyl transferase enzyme and in the absence of a nucleic acid template under conditions sufficient for incorporation of said analog into said oligonucleotide, wherein the nucleotide analog comprises a terminating group linked to a nucleobase that prevents the nucleotidyl transferase from catalyzing addition of either a natural nucleotide or a nucleotide analog into said oligonucleotide until said terminating group is removed; and
 prior to removal of the terminating group, exposing the oligonucleotide to an enzyme having 3'-5' exonuclease activity.

2. The method of claim 1, wherein the terminating group is selected from the group consisting of H, an amide, a carbamate, and a urea, in each case optionally linked to a member selected from the group consisting of a methyl, ethyl, propyl, isopropyl, isobutyl, pivaloyl, cyclohexyl, cyclopropyl, phenyl, naphthyl, anthracenyl, phenanthrenyl, pyrenyl, chrysenyl, pyridinyl, pyrimidinyl, pyrazinyl, indolyl, quinolinyl, isoquinolinyl, furanyl, thiophenyl, morpholinyl, piperidinyl, dioxanyl, tetrahydrofuranyl, and biotin.

3. The method of claim 1, wherein the terminating group linked to the nucleobase forms Nucleobase-R, and Nucleobase-R is selected from the group consisting of deoxyadenosine, deoxycytidine, deoxythymidine, deoxyguanosine, an N6-modified deoxyadenosine, an N4-modified deoxycytidine, an N1-modified deoxythymidine, an 06-modified deoxyguanosine, an N1-modified deoxyguanosine, and an N2-modified deoxyguanosine.

4. The method of claim 1, wherein the enzyme having 3'-5' exonuclease activity is selected from the group consisting of ExoI, Thermolabile ExoI, ExoT, Exo I, Exo T, Thermolabile Exo I, Exo II, Exo III, Exo IV, Exo V, ExoVII, Exo IX, Exo IX, TREX1, TREX2 RNase T, Pol d, Pol e, Pol g, POL3, POL2, MIP1, WRN, p53, MRE11, hRAD1, RAD1, hRAD9, and Rad9.

5. The method of claim 3, wherein Nucleobase-R is selected from the group consisting of N4-modified deoxycytidine, an 06-modified deoxyguanosine, an N1-modified deoxyguanosine, and an N2-modified deoxyguanosine.

6. The method of claim 3, wherein Nucleobase-R is selected from the group consisting of an N4-modified deoxycytidine and an N1-modified deoxythymidine.

7. The method of claim 3, wherein Nucleobase-R is selected from the group consisting of an N4-modified deoxycytidine and an N6-modified deoxyadenosine.

8. The method of claim 3, wherein Nucleobase-R is selected from the group consisting of an 06-modified deoxyguanosine, an N1-modified deoxyguanosine, an N2-modified deoxyguanosine, an N6-modified deoxyadenosine, and an N1-modified deoxythymidine.

9. A method for synthesizing an oligonucleotide, the method comprising:
 a) exposing an oligonucleotide attached to a solid support to a nucleotide analog in the presence of a nucleotidyl transferase enzyme and in the absence of a nucleic acid template under conditions sufficient for incorporation of said analog into said oligonucleotide wherein the nucleotide analog comprises a terminating group linked to a nucleobase that prevents the nucleotidyl transferase from catalyzing addition of either a natural nucleotide or a nucleotide analog into said oligonucleotide until said terminating group is removed;
 b) exposing the oligonucleotide to a second nucleotide analog that does not confer resistance to exonuclease activity prior to removal of the terminating group linked to the nucleobase; and
 c) exposing the oligonucleotide to an enzyme having 3'-5' exonuclease activity prior to removal of the terminating group linked to the nucleobase.

10. The method of claim 9, wherein the second nucleotide analog is selected from the group consisting of a 2',3'-dideoxy nucleotide and a 2',3'-dehydro nucleotide.

11. The method of claim 9, wherein an addition cycle comprises steps a), b), and c), and further comprises removal of the terminating group linked to the nucleobase, the method further comprising repeating the addition cycle 2 or more times.

12. The method of claim 9, wherein an addition cycle comprises steps a) and b) followed by removal of the terminating group linked to the nucleobase, the method further comprising:
 repeating the addition cycle 2 or more times; and
 after a last repetition of the addition cycle, performing a final cycle comprising steps a), b), and c).

13. The method of claim 11, further comprising after a last repetition of the addition cycle, exposing the oligonucleotide to a third nucleotide analog comprising the terminating group linked to the nucleobase and a biotin modification.

14. The method of claim 9, wherein the terminating group is selected from the group consisting of H, an amide, a carbamate, and a urea, in each case optionally linked to a member selected from the group consisting of a methyl, ethyl, propyl, isopropyl, isobutyl, pivaloyl, cyclohexyl, cyclopropyl, phenyl, naphthyl, anthracenyl, phenanthrenyl, pyrenyl, chrysenyl, pyridinyl, pyrimidinyl, pyrazinyl, indolyl, quinolinyl, isoquinolinyl, furanyl, thiophenyl, morpholinyl, piperidinyl, dioxanyl, tetrahydrofuranyl, and biotin.

15. The method of claim 9, wherein the terminating group linked to the nucleobase forms Nucleobase-R, and Nucleobase-R is selected from the group consisting of deoxyadenosine, deoxycytidine, deoxythymidine, deoxyguanosine, an N6-modified deoxyadenosine, an N4-modified deoxycytidine, an N1-modified deoxythymidine, an 06-modified deoxyguanosine, an N1-modified deoxyguanosine, and an N2-modified deoxyguanosine.

16. The method of claim 9, wherein the enzyme having 3'-5' exonuclease activity is selected from the group consisting of ExoI, Thermolabile ExoI, and ExoT, Exo I, Exo T, Thermolabile Exo I, Exo II, Exo III, Exo IV, Exo V, ExoVII, Exo IX, Exo IX, TREX1, TREX2 RNase T, Pol d, Pol e, Pol g, POL3, POL2, MIP1, WRN, p53, MRE11, hRAD1, RAD1, hRAD9, and Rad9.

17. The method of claim 15, wherein Nucleobase-R is selected from the group consisting of N4-modified deoxycytidine, an O6-modified deoxyguanosine, an N1-modified deoxyguanosine, and an N2-modified deoxyguanosine.

18. The method of claim 15, wherein Nucleobase-R is selected from the group consisting of an N4-modified deoxycytidine and an N1-modified deoxythymidine.

19. The method of claim 15, wherein Nucleobase-R is selected from the group consisting of an N4-modified deoxycytidine and an N6-modified deoxyadenosine.

20. The method of claim 15, wherein Nucleobase-R is selected from the group consisting of an O6-modified deoxyguanosine, an N1-modified deoxyguanosine, an N2-modified deoxyguanosine, an N6-modified deoxyadenosine, and an N1-modified deoxythymidine.

* * * * *

SEQUENCE LISTING

```
Sequence total quantity: 10
SEQ ID NO: 1            moltype = AA  length = 520
FEATURE                 Location/Qualifiers
source                  1..520
                        mol_type = protein
                        organism = Bos taurus
SEQUENCE: 1
MAQQRQHQRL PMDPLCTASS GPRKKRPRQV GASMASPPHD IKFQNLVLFI LEKKMGTTRR  60
NFLMELARRK GFRVENELSD SVTHIVAENN SGSEVLEWLQ VQNIRASSQL ELLDVSWLIE 120
SMGAGKPVEI TGKHQLVVRT DYSATPNPGF QKTPPLAVKK ISQYACQRKT TLNNYNHIFT 180
DAFEILAENS EFKENEVSYV TFMRAASVLK SLPFTIISMK DTEGIPCLGD KVKCIIEEII 240
EDGESSEVKA VLNDERYQSF KLFTSVFGVG LKTSEKWFRM GFRSLSKIMS DKTLKFTKMQ 300
KAGFLYYEDL VSCVTRAEAE AVGVLVKEAV WAFLPDAFVT MTGGFRRGKK IGHDVDFLIT 360
SPGSAEDEEQ LLPKVINLWE KKGLLLYYDL VESTFEKFKL PSRQVDTLDH FQKCFLILKL 420
HHQRVDSSKS NQQEGKTWKA IRVDLVMCPY ENRAFALLGW TGSRQFERDI RRYATHERKM 480
MLDNHALYDK TKRVFLKAES EEEIFAHLGL DYIEPWERNA                      520

SEQ ID NO: 2            moltype = DNA  length = 1923
FEATURE                 Location/Qualifiers
source                  1..1923
                        mol_type = genomic DNA
```

```
                     organism = Bos taurus
SEQUENCE: 2
ctcttctgga gataccactt gatggcacag cagaggcagc atcagcgtct tcccatggat    60
ccgctgtgca cagcctcctc aggccctcgg aagaagagac ccaggcaggt gggtgcctca   120
atggcctccc ctcctcatga catcaagttt caaaatttgg tcctcttcat tttggagaag   180
aaaatgggaa ccacccgcag aaacttcctc atggagctgg ctcgaaggaa aggtttcagg   240
gttgaaaatg agctcagtga ttctgtcacc cacattgtag cagaaaacaa ctctggttca   300
gaggttctcg agtggcttca ggtacagaac ataagagcca gctcgcagct agaactcctt   360
gatgtctcct ggctgatcga aagtatggga gcaggaaaac cagtggagat tacaggaaaa   420
caccagcttg ttgtgagaac agactattca gctaccccaa acccaggctt ccagaagact   480
ccaccacttg ctgtaaaaaa gatctcccag tacgcgtgtc aaagaaaaac cactttgaac   540
aactataacc acatattcac ggatgccttt gagatactgg ctgaaaattc tgagtttaaa   600
gaaaatgaag tctcttatgt gacatttatg agagcagctt ctgtacttaa atctctgcca   660
ttcacaatca tcagtatgaa ggatacagaa ggaattccct gcctgggggga caaggtgaag   720
tgtatcatag aggaaattat tgaagatgga gaagttctg aagttaaagc tgtgttaaat   780
gatgaacgat atcagtcctt caaactcttt acttctgttt ttggagtggg actgaagaca   840
tctgagaaat ggttcaggat ggggttcaga tctctgagta aaataatgtc agacaaaacc   900
ctgaaattca caaaaatgca gaaagcagga ttttctctatt atgaagacct tgtcagctgc   960
gtgaccaggg ccgaagcaga ggcggttggc gtgctggtta aagaggctgt gtgggcattt  1020
ctgccggatg cctttgtcac catgacagga ggattccgca ggggtaagaa gattgggcat  1080
gatgtagatt ttttaattac cagcccagga tcagcagagg atgaagagca acttttgcct  1140
aaagtgataa acttatggga aaaaaaggga ttactttat attatgacct tgtggagtca  1200
acatttgaaa agttcaagtt gccaagcagg caggtggata ctttagatca ttttcaaaaa  1260
tgctttctga tttaaaaatt gcaccatcag agagtagaca gtagcaagtc caaccagcag  1320
gaaggaaaga cctggaaggc catccgtgtg gacctggtta tgtgccccta cgagaaccgt  1380
gcctttgccc tgctaggctg gactggctcc cggcagtttg agagagacat ccggcgctat  1440
gccacacacg agcggaagat gatgctggat aaccacgctt tatatgacaa gaccaagagg  1500
gtatttctca aagcggaaag tgaagaagaa atctttgcac atctgggatt ggactacatt  1560
gaaccatggg aaagaaatgc ttaggagaaa gctgtcaact ttttctttt ctgttctttt  1620
tttcaggtta gacaaattat gcttcatatt ataatgaaag atgccttagt caagtttggg  1680
attctttaca ttttaccaag atgtagaatt cttctagaaa taagtagttt tggaaacgtg  1740
atcaggcacc ccctgggtta tgtctggcaa agccatttgc aggactgatg tgtagaactc  1800
gcaatgcatt ttccatagaa acagtgttgg aattggtggc tcatttccag ggaagttcat  1860
caaagcccac tttgcccaca gtgtagctga aatactgtat acttgccaat aaaaatagga  1920
aac                                                                1923

SEQ ID NO: 3           moltype = AA  length = 465
FEATURE                Location/Qualifiers
source                 1..465
                       mol_type = protein
                       organism = Escherichia coli
SEQUENCE: 3
MFTRVANFCR KVLSREESEA EQAVARPQVT VIPREQHAIS RKDISENALK VMYRLNKAGY    60
EAWLVGGGVR DLLLGKKPKD FDVTTNATPE QVRKLFRNCR LVGRRFRLAH VMFGPEIIEV   120
ATFRGHHEGN VSDRTTSQRG QNGMLLRDNI FGSIEEDAQR RDFTINSLYY SVADFTVRDY   180
VGGMKDLKDG VIRLIGNPET RYREDPVRML RAVRFAAKLG MRISPETAEP IPRLATLLND   240
IPPARLFEES LKLLQAGYGY ETYKLLCEYH LFQPLFPTIT RYFTENGDSP MERIIEQVLK   300
NTDTRIHNDM RVNPAFLFAA MFWYPLLETA QKIAQESGLT YHDAFALAMN DVLDEACRSL   360
AIPKRLTTLT RDIWQLQLRM SRRQGKRAWK LLEHPKFRAA YDLLALRAEV ERNAELQRLV   420
KWWGEFQVSA PPDQKGMLNE LDEEPSPRRR TRRPRKRAPR REGTA                   465

SEQ ID NO: 4           moltype = DNA  length = 1398
FEATURE                Location/Qualifiers
source                 1..1398
                       mol_type = unassigned DNA
                       organism = Escherichia coli
SEQUENCE: 4
attttacccc gagtcgctaa ttttttgccgc aaggtgctaa gccgcgagga aagcgaggct    60
gaacaggcag tcgcccgtcc acaggtgacg gtgatcccgc gtgagcagca tgctatttcc   120
cgcaaagata tcagtgacaa tgccctgaag gtaatgtaca ggctcaataa agcgggatac   180
gaagcctggc tggttggcgg cggcgtgcgc gacctgttac ttggcaaaaa gccgaaagat   240
tttgacgtaa ccactaacgc cacgcctgag caggtgcgca aactgttccg taactgccgc   300
ctggtgggtc gccgtttccg tctggctcat gtaatgtttg gcccggagat tatcgaagtt   360
gcgaccttcc gtggacacca cgaaggtaac gtcagcgacc gtaccacgag ccaaacgcgg   420
caaaacggca tgttgctgcg cgacaacatt tccggctcca tcgaagaaga cgcccagcgc   480
cgcgatttca ctatcaacag cctgtattac agcgtagcgg attttaccgt ccgtgattac   540
gttggcggca tgaaggatct gaaggacggc gttatccgtc tgattggtaa cccggaaacg   600
cgctaccgtg aagatccggt acgtatgctg cgcgcggtac gttttgccgc caaattgggt   660
atgcgcatca gcccggaaac cgcagaaccg atccctcgtc tgctacccct gctgaacgat   720
atcccaccgg cacgcctgtt tgaagaatcg cttaaactgc tacaagcggg ctacggttac   780
gaaacctata gctgttgtg tgaatatcat ctgttccagc cgctgttccc gaccattacc   840
cgctacttca cggaaaatgg cgacagcccg atggagcgga tcattgaaca ggtgctgaag   900
aataccgata cgcgtatcca taacgatatg cgcgtgaacc cggcgttcct gtttgccgcc   960
atgttctggt accccactgct ggagacggca cagaagatgc acgaagcctg ccgttcactg  1020
tatcacgacg ctttcgcgct ggcgatgaac gacgtgctgg acgaagcctg ccgttcactg  1080
gcaatcccga aacgtctgac gacattaacc cgcgatatct ggcagttgca gttgcgtatg  1140
tcccgtcgtc agggtaaacg cgcatggaaa ctgctggagc atcctaagtt ccgtgcggct  1200
tatgacctgt tggccttgcg agctgaagtt gagcgtaacg ctgaactgca gcgtctggtg  1260
aaatggtggg gtgagttcca ggtttccgcg ccaccagacc aaaaagggat gctcaacgag  1320
```

```
ctggatgaag aaccgtcacc gcgtcgtcgt actcgtcgtc cacgcaaacg cgcaccacgt    1380
cgtgagggta ccgcatga                                                  1398

SEQ ID NO: 5            moltype = AA  length = 349
FEATURE                 Location/Qualifiers
source                  1..349
                        mol_type = protein
                        organism = Escherichia coli
SEQUENCE: 5
GSHMSYQKVP NSHKEFTKFC YEVYNEIKIS DKEFKEKRAA LDTLRLCLKR ISPDAELVAF     60
GSLESGLALK NSDMDLCVLM DSRVQSDTIA LQFYEELIAE GFEGKFLQRA RIPIIKLTSD    120
TKNGFGASFQ CDIGFNNRLA IHNTLLLSSY TKLDARLKPM VLLVKHWAKR KQINSPYFGT    180
LSSYGYVLMV LYYLIHVIKP PVFPNLLLSP LKQEKIVDGF DVGFDDKLED IPPSQNYSSL    240
GSLLHGFFRF YAYKFEPREK VVTFRRPDGY LTKQEKGWTS ATEHTGSADQ IIKDRYILAI    300
EDPFEISHNV GRTVSSSGLY RIRGEFMAAS RLLNSRSYPI PYDSLFEEA                349

SEQ ID NO: 6            moltype = DNA  length = 1047
FEATURE                 Location/Qualifiers
source                  1..1047
                        mol_type = unassigned DNA
                        organism = Escherichia coli
SEQUENCE: 6
ggcagccata tgagctatca gaaagtgccg aacagccata agaatttac caaattttgc      60
tatgaagtgt ataacgaaat taaaattagc gataaagaat ttaaagaaaa acgcgcggcg    120
ctggatacc tgcgcctgtg cctgaaacgc attagcccgg atgcggaact ggtggcgttt    180
ggcagcctga aaagcggcct ggcgctgaaa aacagcgata tggatctgtg cgtgctgatg    240
gatgccgcg tgcagagcga taccattgcg ctgcagtttt atgaagaact gattgcggat    300
ggctttgaag caaatttct ccagcgcgcg cgcattccga ttattaaact gaccagcgat    360
accaaaaacg gctttggcgc gagctttcag tgcgatattg ctttaacaa ccgcctggcg    420
attcataaca ccctgctgct gagcagctat accaaactgg atgcgcgcct gaaaccgatg    480
gtgctgctgg tgaaacattg ggcgaaacgc aaacagatta cagcccgta tttttggcacc    540
ctgagcagct atggctatgt gctgatggtg ctgtattatc tgattcatgt gattaaaccg    600
ccggtgtttc cgaacctgct gctgagcccg ctgaaacagg aaaaaattgt ggatggcttt    660
gatgtgggct ttgatgataa actggaagat attccgccga gccagaacta tagcagcctg    720
ggcagcctgc tgcatggctt tttcgctttt atgcgtata aatttgaacc gcgcgaaaaa    780
gtggtgacct tcgccgcc ggatggctat ctgaccaaac aggaaaaagg ctggaccagc    840
gcgaccgaac ataccggcag cgcggatcag attattaaag atcgctatat tctggcgatt    900
gaagatccgt ttgaaattag ccataacgtg ggccgcaccg tgagcagcag cggcctgtat    960
cgcattcgcg gcgaatttat ggcggcgagc cgcctgctga acagccgcag ctatccgatt   1020
ccgtatgata gcctgtttga agaagcg                                       1047

SEQ ID NO: 7            moltype = DNA  length = 30
FEATURE                 Location/Qualifiers
misc_feature            1..30
                        note = synthesized
source                  1..30
                        mol_type = other DNA
                        organism = synthetic construct
SEQUENCE: 7
ttattattat tattaaaaaa ggccaaaaaa                                       30

SEQ ID NO: 8            moltype = DNA  length = 34
FEATURE                 Location/Qualifiers
misc_feature            1..34
                        note = synthesized
source                  1..34
                        mol_type = other DNA
                        organism = synthetic construct
SEQUENCE: 8
ttaattaatt tttgtgagct taatgtcctt atgt                                  34

SEQ ID NO: 9            moltype = DNA  length = 21
FEATURE                 Location/Qualifiers
misc_feature            1..21
                        note = synthesized
source                  1..21
                        mol_type = other DNA
                        organism = synthetic construct
SEQUENCE: 9
gtgagcttaa tgtccttatg t                                                21

SEQ ID NO: 10           moltype = DNA  length = 21
FEATURE                 Location/Qualifiers
misc_feature            1..21
                        note = synthesized
```

```
source          1..21
                mol_type = other DNA
                organism = synthetic construct
SEQUENCE: 10
gtgagcttaa tgtccttatg t                                        21
```